(12) United States Patent
Sun et al.

(10) Patent No.: US 10,888,832 B2
(45) Date of Patent: Jan. 12, 2021

(54) METHODS AND COMPOSITIONS FOR SINGLE MOLECULE COMPOSITION LOADING

(71) Applicant: Pacific Biosciences of California, Inc., Menlo Park, CA (US)

(72) Inventors: Lei Sun, San Jose, CA (US); Natasha Popovich, Belmont, CA (US); Gene Shen, Santa Clara, CA (US); Thang Pham, Mountain View, CA (US); Stephen Turner, Eugene, OR (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 16/690,456

(22) Filed: Nov. 21, 2019

(65) Prior Publication Data

US 2020/0164335 A1 May 28, 2020

Related U.S. Application Data

(63) Continuation of application No. 16/374,254, filed on Apr. 3, 2019, now Pat. No. 10,525,438, which is a (Continued)

(51) Int. Cl.
*B01J 19/00* (2006.01)
*C12Q 1/6806* (2018.01)
(Continued)

(52) U.S. Cl.
CPC ........ *B01J 19/0046* (2013.01); *C12Q 1/6804* (2013.01); *C12Q 1/6806* (2013.01); (Continued)

(58) Field of Classification Search
CPC .......... B01J 19/0046; B01J 2219/00596; B01J 2219/0061; B01J 2219/00619; (Continued)

(56) References Cited

U.S. PATENT DOCUMENTS

| 4,711,955 A | 12/1987 | Ward et al. |
| 5,001,050 A | 3/1991 | Blanco et al. |

(Continued)

FOREIGN PATENT DOCUMENTS

| WO | 2007075987 A2 | 7/2007 |
| WO | 2007076057 A2 | 7/2007 |

(Continued)

OTHER PUBLICATIONS

Andersen et al., (2008) "Assembly and structural analysis of a covalently closed nano-scale DNA cage" Nucleic Acids Research 36(4): 1113-1119

(Continued)

*Primary Examiner* — Jeremy C Flinders
(74) *Attorney, Agent, or Firm* — Monicia Elrod-Erickson

(57) ABSTRACT

The present invention provides methods, compositions, and systems for distributing single polymerase molecules into array regions. In particular, the methods, compositions, and systems of the present invention result in a distribution of single polymerase molecules into array regions at a percentage that is larger than the percentage expected to be occupied under a Poisson distribution.

18 Claims, 35 Drawing Sheets

Related U.S. Application Data continuation of application No. 15/078,915, filed on Mar. 23, 2016, now Pat. No. 10,300,452.

(60) Provisional application No. 62/137,689, filed on Mar. 24, 2015.

(51) Int. Cl.
  *C12Q 1/6834* (2018.01)
  *C12Q 1/6804* (2018.01)
  *C12Q 1/6874* (2018.01)

(52) U.S. Cl.
  CPC ......... *C12Q 1/6834* (2013.01); *C12Q 1/6874* (2013.01); *B01J 2219/0061* (2013.01); *B01J 2219/0074* (2013.01); *B01J 2219/00596* (2013.01); *B01J 2219/00619* (2013.01); *B01J 2219/00626* (2013.01); *B01J 2219/00648* (2013.01); *B01J 2219/00722* (2013.01)

(58) Field of Classification Search
  CPC .... B01J 2219/00626; B01J 2219/00648; B01J 2219/00722; B01J 2219/0074; C12Q 1/6804; C12Q 1/6806; C12Q 1/6834; C12Q 1/6874
  See application file for complete search history.

(56) References Cited

U.S. PATENT DOCUMENTS

| | | |
|---|---|---|
| 5,034,506 A | 7/1991 | Summerton et al. |
| 5,198,543 A | 3/1993 | Blanco et al. |
| 5,235,033 A | 8/1993 | Summerton et al. |
| 5,476,928 A | 12/1995 | Ward et al. |
| 5,576,204 A | 11/1996 | Blanco et al. |
| 6,917,726 B2 | 7/2005 | Levene et al. |
| 7,057,026 B2 | 6/2006 | Barnes et al. |
| 7,315,019 B2 | 1/2008 | Turner et al. |
| 7,692,783 B2 | 4/2010 | Lundquist |
| 7,715,001 B2 | 5/2010 | Lundquist |
| 7,901,889 B2 | 3/2011 | Christians et al. |
| 7,968,702 B2 | 6/2011 | Wegener et al. |
| 7,981,632 B2 | 7/2011 | Schmidt |
| 7,995,202 B2 | 8/2011 | Lundquist |
| 8,530,167 B2 | 9/2013 | Patel et al. |
| 8,802,600 B2 | 8/2014 | Rank et al. |
| 8,877,438 B2 | 11/2014 | Yin |
| 9,127,259 B2 | 9/2015 | Bjornson et al. |
| 2003/0044781 A1 | 3/2003 | Korlach et al. |
| 2004/0241716 A1 | 12/2004 | Kumar et al. |
| 2007/0036511 A1 | 2/2007 | Lundquist |
| 2007/0238679 A1 | 10/2007 | Rank et al. |
| 2008/0108082 A1 | 5/2008 | Rank et al. |
| 2009/0298075 A1 | 12/2009 | Travers et al. |
| 2010/0009872 A1 | 1/2010 | Eid et al. |
| 2010/0093555 A1 | 4/2010 | Bjornson et al. |
| 2010/0112645 A1 | 5/2010 | Clark et al. |
| 2011/0059505 A1 | 3/2011 | Hanzel et al. |
| 2011/0189659 A1 | 8/2011 | Clark et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0034602 A1 | 2/2012 | Emig et al. |
| 2012/0085894 A1 | 4/2012 | Zhong et al. |
| 2013/0116153 A1 | 5/2013 | Bowen et al. |
| 2013/0327644 A1 | 12/2013 | Turner et al. |
| 2013/0338010 A1 | 12/2013 | Turner et al. |
| 2014/0038178 A1 | 2/2014 | Otto et al. |
| 2014/0051068 A1 | 2/2014 | Cherf et al. |
| 2015/0011433 A1 | 1/2015 | Miller et al. |
| 2015/0050659 A1 | 2/2015 | Sebo et al. |

FOREIGN PATENT DOCUMENTS

| | | |
|---|---|---|
| WO | 2007123763 A2 | 11/2007 |
| WO | 2008051530 A2 | 5/2008 |
| WO | 2009145818 A1 | 12/2009 |

OTHER PUBLICATIONS

Dietz, H. et al., "Folding DNA into Twisted and Curved Nanoscale Shapes", Science 325(5941): 725-730 (2009).
Douglas S. M. et al., "Self-Assembly of DNA into Nanoscale Three-Dimensional Shapes", Nature 459:414-418 (2009).
Driscoll, R. J., et al., "Atomic-Scale Imaging of DNA Using Scanning Tunneling Microscopy"Nature, 346(6281): (1990) 294-296.
Eid, J. et al., "Real-Time DNA Sequencing from Single Polymerase Molecules", Science, 323(5910), 133-138 (2009).
Foquet et al., "Improved fabrication of zero-mode waveguides for single-molecule detection" Journal of Applied Physics 103, 034301 (2008).
Glatthar, R. et al., "A New Photocleavable Linker in Solid-Phase Chemistry for Ether Cleavage", Org. Lett., 2(15), (2000) 2315-2317, (2000).
Goodwin, P. M., et al., Application of Single Molecule Detection to DNA Sequencing. Nucleosides & Nucleotides, 16 (5-6): 543-550 (1997).
Howorka, S., et al., Sequence-Specific Detection of Individual DNA Strands using Engineered Nanopores, Nature Biotechnology, 19(7): 636-639 (2001).
Korlach et al., "Selective aluminum passivation for targeted immobilization of single DNA polymerase molecules in zero-mode waveguide nanostructures", Proceedings of the National Academy of Sciences U.S.A. 105(4): 1176-1181 (2008).
Levene et al., "Zero-Mode Waveguides for Single-Molecule Analysis at High Concentrations", Science, 299:682-686.
Lundquist et al., "Parallel Confocal Detection of Single Molecules in Real Time", Optics Letters, 33(9):1026-1028 (2008).
Meller, A., et al., Rapid Nanopore Discrimination Between Single Polynucleotide Molecules, Proceedings of the National Academy of Sciences of the United States of America, 97(3): 1079-1084 (2000).
Park et al. (2006) "Finite-Size, Fully Addressable DNA Tile Lattices Formed by Hierarchical Assembly Procedures" Angew. Chem. Int. Ed. 45:735-739.
Rigler, et al., "DNA-Sequencing at the Single Molecule Level", Journal of Biotechnology, 86(3): 161 (2001).
Rodebaugh, R.; et al., "A New o-Nitrobenzyl Photocleavable Linker for Solid Phase Sunthesis", Tetrahedron Lett., 38, 7653-7656 (1997).
Rothemund et al. (2004) "Algorithmic Self-Assembly of DNA Sierpinski Triangles", PLoS Biol 2(12): e424.
Rothemund,P., "Folding DNA to Creat Nanoscale Shapes and Patterns", Nature 440: 297-302 (2006).
Villalonga et al. 2007) "Supramolecular Chemistry of Cyclodextrins in Enzyme Technology," Chem. Rev. 107:3088-3116.
Weisbrod et al. (2007) "A Nucleoside Triphosphate for Site-Specific Labelling of DNA by the Staudinger Ligation," Chem Comm 18:1828-1830.
Weizmann et al. (2008) "A polycatenated DNA scaffold for the one-step assembly of hierarchical nanostructures" PNAS 105(14) 5289-5294.
Zhang et al. (2006) "Periodic Square-Like Gold Nanoparticle Arrays Templated by Self-Assembled 2D DNA Nanogrids on a Surface" Nano Lett. 6(2): 248-251.
Zhang et al. (2008) Conformational flexibility facilitates self-assembly of complex DNA nanostructures PNAS 105 (31):10665-10669.
Zheng et al. (2013) "Single-Stranded DNA as a Cleavable Linker for Bioorthogonal Click Chemistry-Based Proteomics," Bioconjug Chem. 24(6):859-864.
Zimmermann et al. (2007) "Self-Assembly of a DNA Dodecahedron from 20 Trisoligonucleotides with C3h Linkers" Angewandte Chemie International Edition, doi: 10.1002/anie.200702682.
EP Search Report dated Oct. 2, 2018 for related case EP16769633.5.

(56) References Cited

OTHER PUBLICATIONS

International Search Report and Written Opinion dated Jun. 27, 2016 for related PCT/US2016/023824.
International Preliminary Report on Patentability dated Oct. 5, 2017 for related PCT/US2016/023824.

FIG. 8A
PEG250
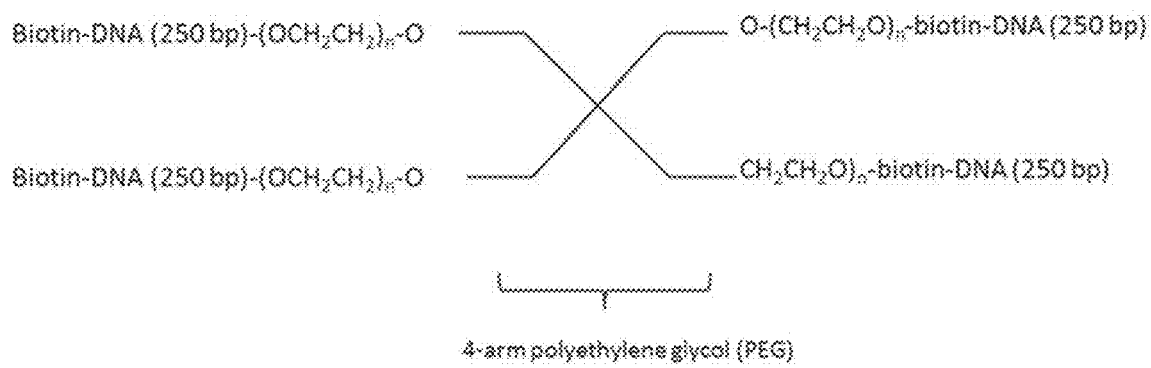
PEG500
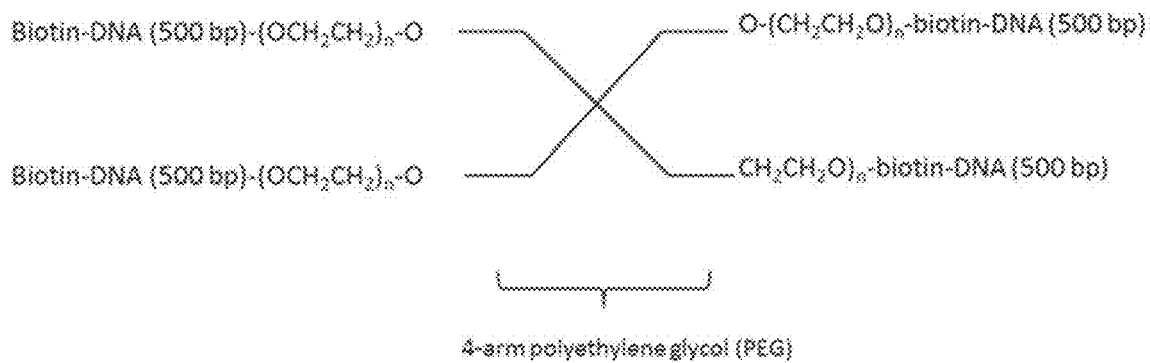

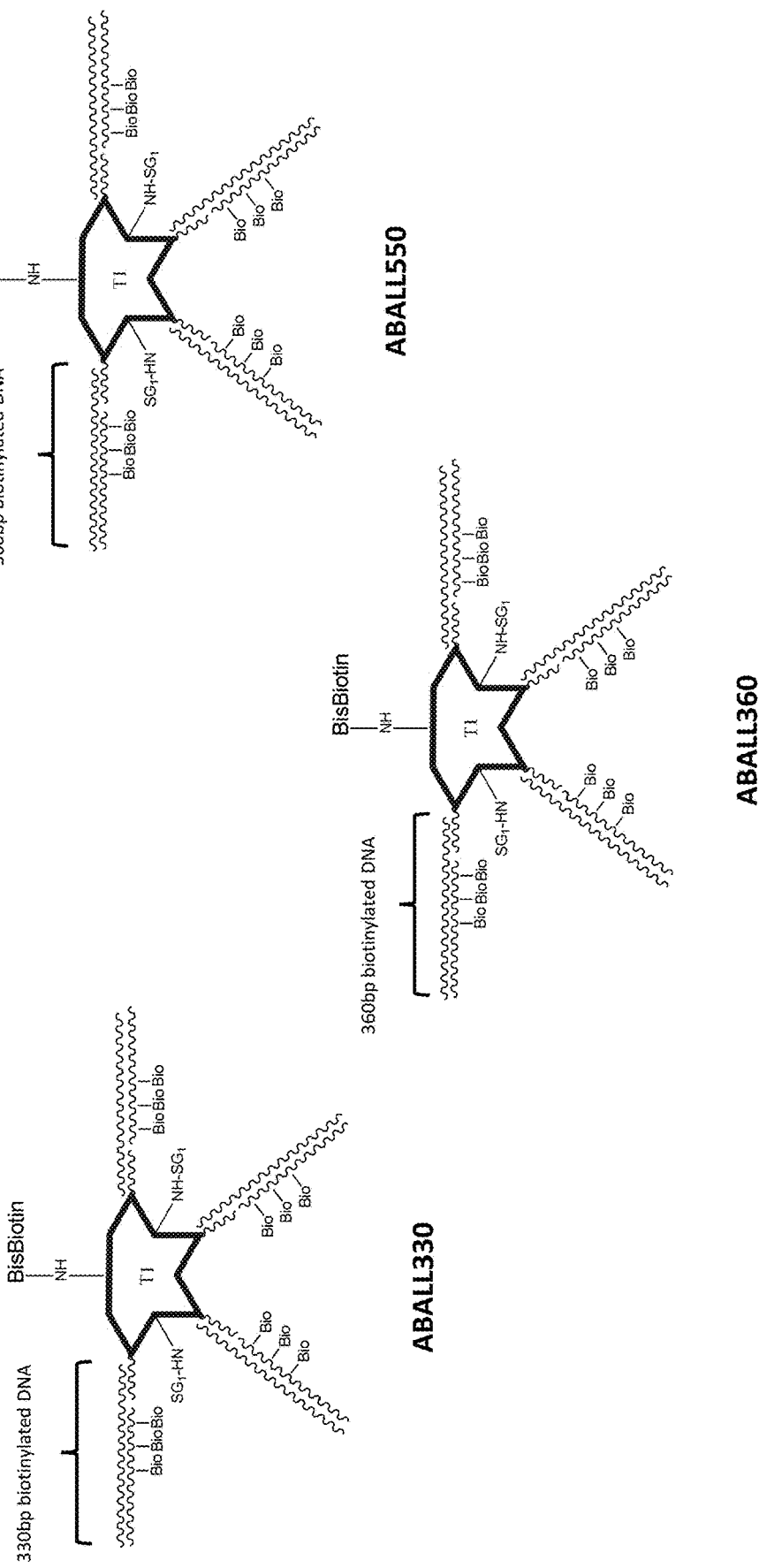

Fig. 12
Spacer:
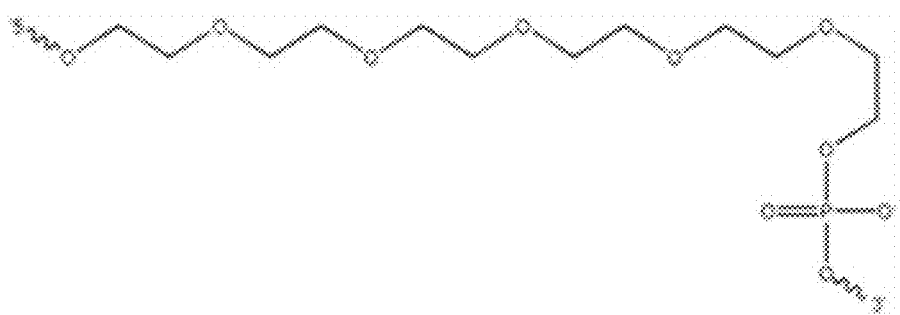
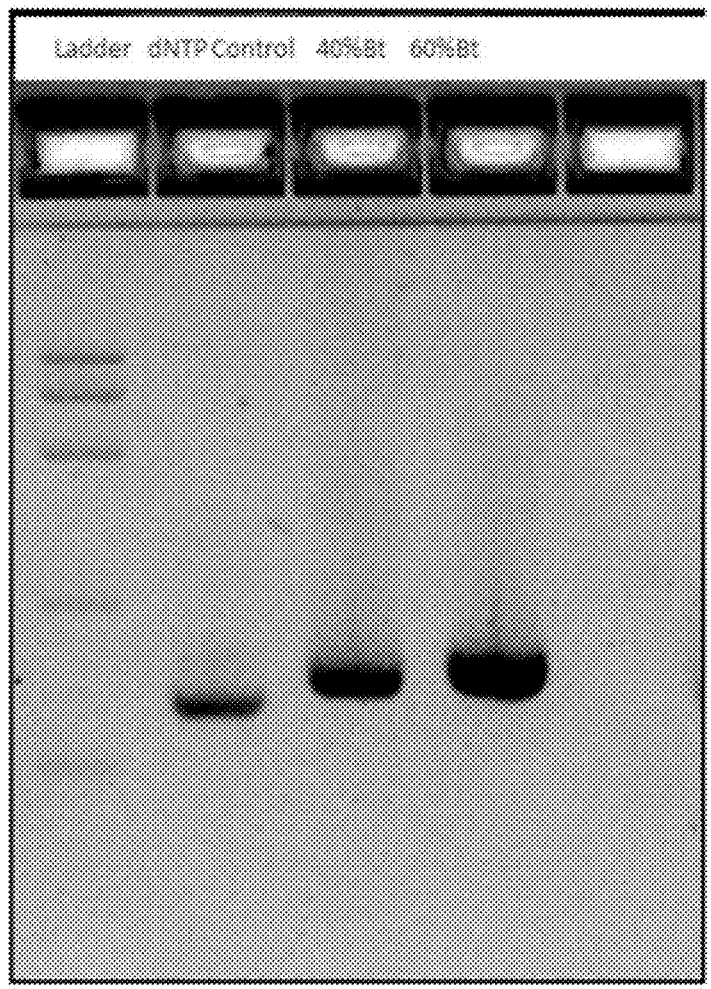

6-Arm-Primer [(SG1)3-CS2 core scaffold]

FIG. 20
4-Arm A-Ball SC2 Scaffold
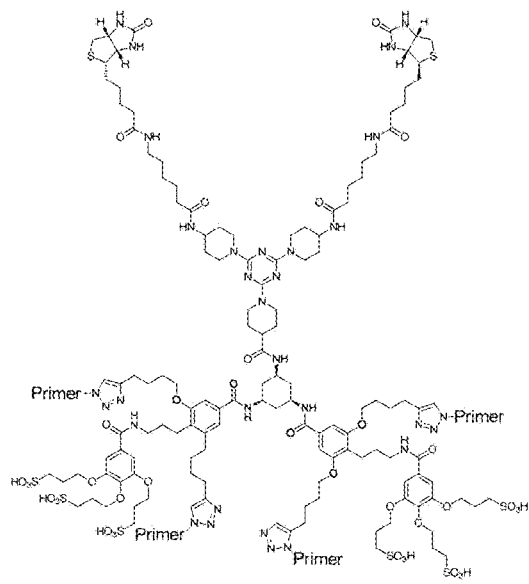
4-Arm A-Ball T1 Scaffold
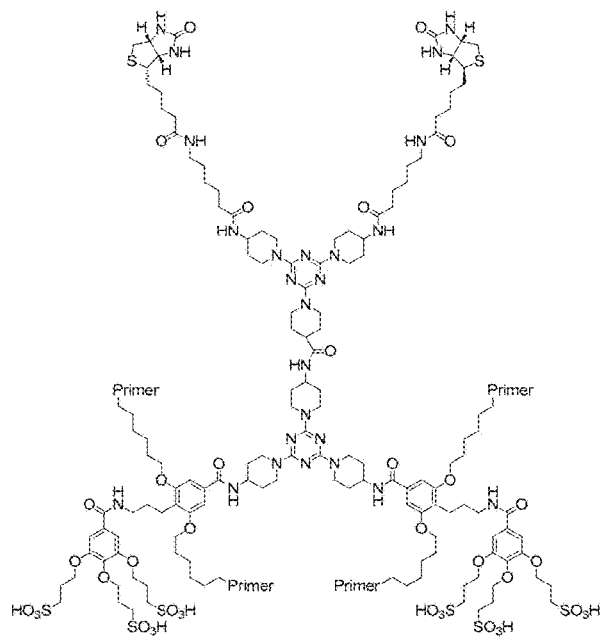
6-Arm A-Ball SC2 Scaffold
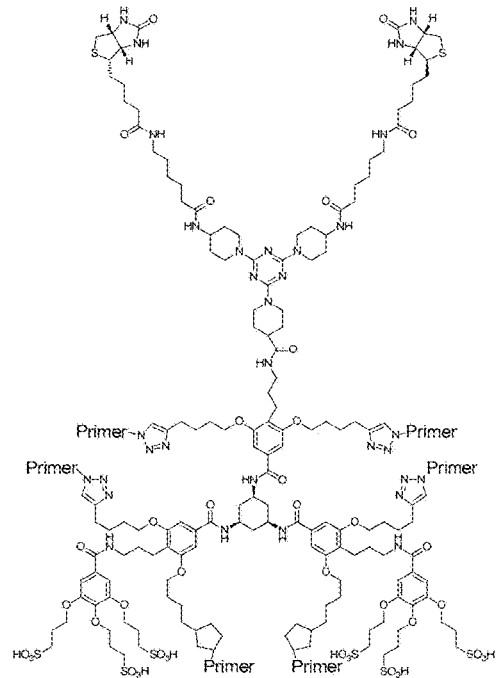

METHODS AND COMPOSITIONS FOR SINGLE MOLECULE COMPOSITION LOADING

CROSS-REFERENCE TO RELATED APPLICATIONS

This application is a continuation application of U.S. patent application Ser. No. 16/374,254 filed on Apr. 3, 2019, which is a continuation application of U.S. patent application Ser. No. 15/078,915 filed on Mar. 23, 2016, now U.S. Pat. No. 10,300,452, which claims priority to U.S. Provisional Application No. 62/137,689 filed on Mar. 24, 2015 the disclosures of which are incorporated herein by reference in their entirety for all purposes.

BACKGROUND OF THE INVENTION

Techniques in molecular biology and molecular medicine often rely on analysis of single biological molecules. Such techniques include DNA and RNA sequencing, polymorphism detection, the detection of proteins of interest, the detection of protein-nucleic acid complexes, and many others. The high sensitivity, high throughput and low reagent costs involved in single molecule analysis make this type of analysis an increasingly attractive approach for a variety of detection and analysis problems in molecular medicine, from low cost genomics to high sensitivity marker analysis.

For example, single molecule DNA sequencing is useful for the analysis of large sets of related DNAs, such as those that occur in a genome. In some sequencing methods, a polymerase reaction is isolated within an array of extremely small (typically optically confined) observation volumes that permit observation of the enzymatic action of individual polymerases in each reaction/observation volume of the array, while the polymerase copies a template nucleic acid. Nucleotide incorporation events are individually detected, ultimately providing the sequence of the template molecule. This approach dramatically increases throughput of sequencing systems while also dramatically reducing reagent consumption costs, making where personalized genomics increasingly feasible.

The small observation volumes often used for single molecule nucleic acid sequencing and other analysis methods are typically provided by immobilizing or otherwise localizing the polymerase (or other) enzyme within an optical confinement reaction/observation region, such as an array of extremely smalls wells as in an array of Zero Mode Waveguides (ZMWs), and delivering a template, primers, etc., to the reaction region. One difficulty in performing single molecule analyses occurs in loading the reaction/observation region of single molecule analysis devices with the molecules of interest (e.g., template or other analyte and/or enzyme). Loading two or more molecules of interest into a reaction region tends to complicate any analysis of signals observed from double (or more than double)-loaded region. This is because two (or more) sets of signals may simultaneously be observed from the reaction region, meaning that the signals from reach reaction region would have to be deconvoluted before data from the observation region could be used. More typically, data from double(+) loaded reaction regions is recognized by various data analysis methods, and that data is then simply discarded.

To reduce the incidence of multiple molecule loading events in the relevant reaction/observation volume(s) of the array, it is typical in the art to substantially "under-load" the array with the analyte molecules of interest. Random distribution of molecules into the array results in one or fewer molecules being loaded into most reaction/observation volumes when fewer than 37% of all observation volumes are loaded. This type of loading is referred to as "Poisson-limited" analyte loading, meaning that few enough molecules are added to the array so that a Poisson-style random statistical distribution of the analytes into the array results in one or fewer analytes per observation volume in most cases. In the ZMW context, state of the art yields for single-molecule occupancies of approximately 30% have been obtained for a range of ZMW diameters (e.g., 70-100 nm). For this degree of loading, about 60% of the ZMWs in a typical ZMW array are not loaded (e.g., have no analyte molecules).

While random distribution methods are effective in ensuring that, in most cases, not more than a single template or enzyme (or other analyte) molecule is loaded in each observation/reaction volume in an array such as a ZMW array, it would be desirable to develop methods and compositions for increasing the template and enzyme loading density of such arrays. Higher single-molecule loading densities would permit the analysis of more analyte molecules in the array, increasing the throughput of such systems, while simultaneously decreasing analysis costs. The present invention provides these and other features that will be apparent upon complete review of the following.

SUMMARY OF THE INVENTION

Accordingly, the present invention provides methods, compositions, and systems for distributing single polymerase molecules into array regions. In particular, the methods, compositions, and systems of the present invention result in a distribution of single polymerase molecules into array regions at a percentage that is larger than the percentage occupied under a Poisson distribution.

In one aspect, the present invention provides a method of distributing single polymerase molecules into a plurality of array regions, the method comprising steps including (a) providing a surface comprising a plurality of array regions, wherein each array region comprises several binding elements; (b) exposing the surface to a solution comprising polymerase enzyme compositions, wherein each polymerase enzyme composition comprises a polymerase bound to a scaffold, wherein the scaffold comprises a core comprising conjugation adaptors and multiple arms comprising biotin moieties attached to DNA molecules, wherein the exposing is conducted under conditions such that the biotin moieties of the DNA scaffold react with the binding elements of the array regions, wherein in at least some of the array regions, the multiple biotin moieties react with available binding sites in a given array region to thereby prevent other polymerase enzyme compositions from loading in that given array region, thereby distributing single polymerase molecules into a plurality of array regions.

In one embodiment and in accordance with the methods described herein, the single nucleic acid template used in methods of the invention comprises: (i) a double stranded nucleic acid segment having a first and second end; (ii) a first hairpin oligonucleotide connecting each strand of the single template nucleic acid at the first end; (iii) a second hairpin oligonucleotide connecting each strand of the single template nucleic acid at the second end.

In a further aspect, the present invention provides a method of distributing single polymerase molecules into a plurality of array regions, the method comprising: (a) providing a surface comprising a plurality of array regions, wherein each array region comprises several binding elements; (b) exposing the surface to a solution comprising polymerase enzyme compositions, wherein each polymerase enzyme compositions comprise a polymerase attached to a scaffold, wherein the scaffold comprises: a core comprising conjugation adaptors and multiple arms comprising avidin moieties attached to DNA molecules, wherein the exposing is conducted under conditions such that the biotin moieties of the scaffold react with the binding elements of the array regions, wherein in at least some of the array regions, the multiple avidin moieties react with available binding sites in a given array region to thereby prevent other polymerase enzyme compositions from loading in that given array region, thereby distributing single polymerase molecules into a plurality of array regions.

In a still further aspect, the present invention provides a method of distributing single polymerase molecules into array regions, the method comprising: (a) providing a surface comprising a plurality of array regions, wherein each array region comprises several binding elements; (b) exposing the surface to a solution comprising polymerase enzyme compositions, wherein each polymerase enzyme composition comprises a polymerase bound to a linear DNA structure comprising multiple functional moieties, wherein: (i) the multiple functional moieties comprise a member selected from the group consisting of biotin and avidin, (ii) the exposing is conducted under conditions such that the multiple functional moieties of the linear DNA structure react with available binding elements in a given array region and prevent other polymerase enzyme compositions from loading in that given array region, thereby distributing single polymerase molecules into array regions. In some embodiments, the multiple functional moieties are incorporated into the linear DNA structure through attachment to a nucleobase. In further embodiments, the multiple functional moieties are attached to the linear DNA structure through flexible linkers, which can in still further embodiments comprise a polymeric structure.

In yet further aspects, the present invention provides a method of distributing single polymerase molecules into array regions, the method comprising; (a) providing a surface comprising a plurality of array regions, wherein each array region comprises several binding elements; (b) exposing the surface to a solution comprising polymerase enzyme compositions, wherein each polymerase enzyme composition comprises a polymerase bound to a DNA origami structure comprising multiple functional moieties, wherein the exposing is conducted under conditions such that the functional moieties of the DNA origami structure react with the binding elements of the array regions, wherein in at least some of the array regions, the multiple functional moieties react with available binding sites in a given array region and prevent other polymerase enzyme compositions from loading in that given array region, thereby distributing single polymerase molecules into array regions. In some exemplary embodiments, the DNA origami structure is a triangle-shaped DNA origami. In further embodiments, the multiple functional moieties are biotin or avidin moieties.

In some aspects, the present invention provides a polymerase enzyme composition that comprises: (a) a single template nucleic acid that in turn comprises: (i) a double stranded nucleic acid segment having a first and second end; (ii) a first hairpin oligonucleotide connecting each strand of the single template nucleic acid at the first end, wherein the first hairpin oligonucleotide comprises a primer binding site; (iii) a second hairpin oligonucleotide connecting each strand of the single template nucleic acid at the second end, wherein the second hairpin oligonucleotide comprises a capture adapter; (b) a polymerase enzyme attached to a scaffold, wherein the scaffold comprises multiple functional moieties; wherein the polymerase enzyme is complexed with the single template nucleic acid by association with a primer bound to the primer binding site of the single template nucleic acid.

In further aspects, the present invention provides a method of distributing single polymerase molecules into a plurality of array regions, the method comprising; (a) forming a plurality of complexes comprising a template nucleic acid molecule, a single polymerase molecule, and a scaffold comprising multiple functional moieties, wherein the template nucleic acid molecule comprises: (i) a double stranded nucleic acid segment having a first and second end; (ii) a first hairpin oligonucleotide connecting each strand of the single template nucleic acid at the first end, wherein the first hairpin oligonucleotide comprises a primer binding site; (iii) a second hairpin oligonucleotide connecting each strand of the single template nucleic acid at the second end, wherein the second hairpin oligonucleotide comprises a capture adapter; (b) providing a surface comprising a plurality of array regions, wherein each array region comprises several binding elements; (c) disposing the plurality of complexes to the surface, wherein the disposing is conducted under conditions such that the functional moieties of the scaffold react with the binding elements of the array regions, wherein in at least some of the array regions, the multiple functional moieties react with available binding sites in a given array region and prevent other complexes from loading in that given array region, thereby distributing single polymerase molecules into array regions.

In yet further aspects, the present invention provides a method of distributing single polymerase molecules into a plurality of array regions, the method comprising; (a) providing a surface comprising a plurality of array regions, wherein each array region comprises several binding elements; (b) exposing the surface to a solution comprising polymerase enzyme compositions, wherein each polymerase enzyme composition comprises a polymerase bound to a scaffold, wherein the scaffold comprises: (i) a core comprising conjugation adaptors, and (ii) multiple arms comprising functional moieties attached to DNA molecules, wherein the exposing is conducted under conditions such that the functional moieties of the DNA scaffold react with the binding elements of the array regions, wherein in at least some of the array regions, the multiple biotin moieties react with available binding sites in a given array region to thereby prevent other polymerase enzyme compositions from loading in that given array region, thereby distributing single polymerase molecules into a plurality of array regions.

In certain exemplary embodiments and in accordance with any of the above, the polymerase enzyme compositions are about 100 to about 200 nm in diameter at the widest point. In further embodiments, the scaffold is at least 150 nm in length at its widest point. In yet further embodiments, the scaffold is large enough to cover at least 90% of the array region.

In certain embodiments and in accordance with any of the above, the core of the scaffold is not a dendrimer.

In further embodiments and in accordance with any of the above, the multiple arms of the scaffold each comprise around 20-30 functional moieties.

In yet further embodiments and in accordance with any of the above the scaffold comprises about 3-5 arms. In still further embodiments, the scaffold comprises about 2, 3, 4, 5, 6, 7, 8, 9 or 10 arms.

BRIEF DESCRIPTION OF THE DRAWINGS

FIG. 8A-FIG. 8C illustrates exemplary scaffolds.

FIG. 12 shows gel electrophoresis data for biotin arms made with 0, 40%, and 60% biotin-UTP.

FIG. 20 illustrates exemplary embodiments of scaffolds of the invention.

DETAILED DESCRIPTION OF THE INVENTION

Figure 1:
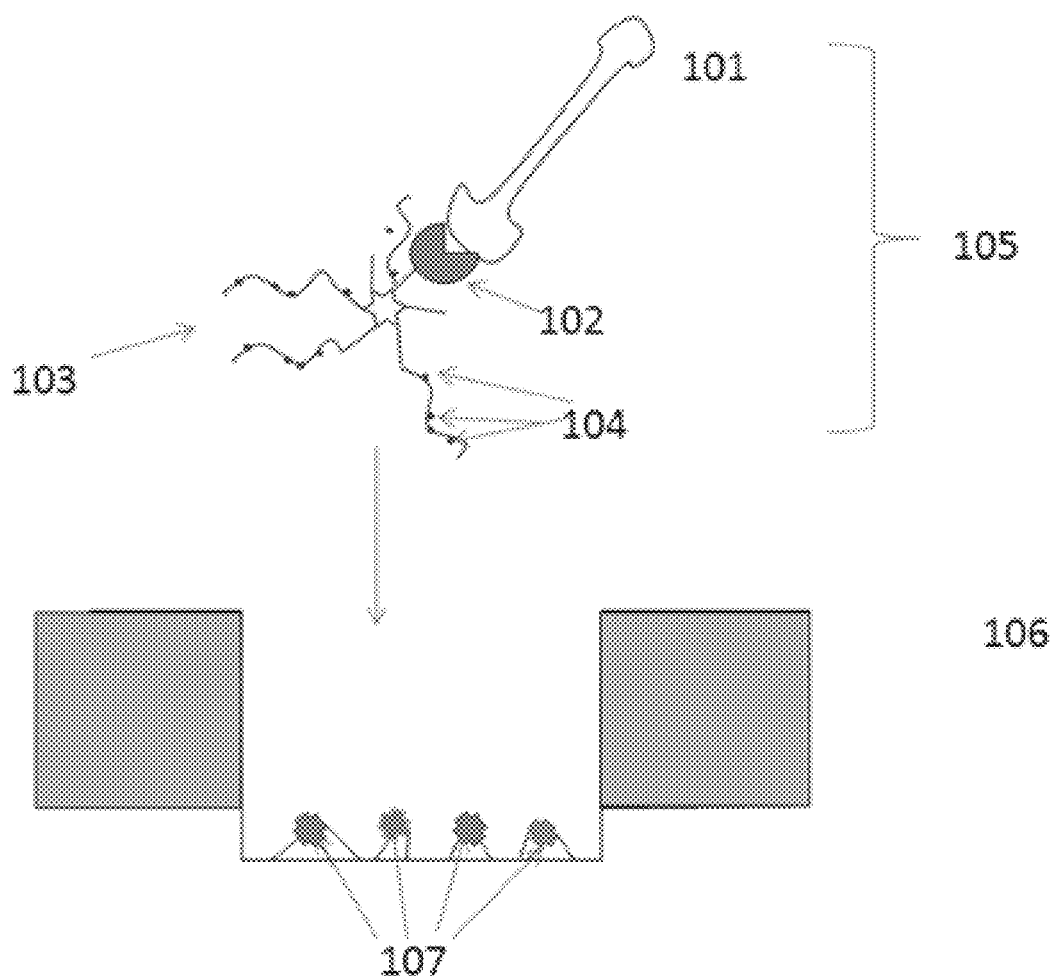
FIG. 1 is a schematic illustration of an embodiment of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*"1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry,* $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

As used herein, a "substantially identical" nucleic acid is one that has at least 80%, 85%, 90%, 95%, 96%, 97%, 98% or 99% sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

I. Overview

The present invention is directed to methods, devices, compositions and systems for distributing single enzyme molecules into a plurality of array regions. In general, the methods, devices, compositions and systems of the present invention result in a distribution of enzyme molecules into array regions such that the number of array regions containing only a single enzyme is greater than the number that would be expected from the Poisson distribution resulting from simple application of a dilute solution of enzyme molecules (also referred to herein as "super-Poisson loading").

Note that although for ease of discussion, the majority of the discussion herein is in terms of polymerase enzymes, it will be appreciated that any other enzyme can be used in the methods, devices, compositions, and systems of the invention. In particular, the scaffolds described herein can be used in compositions that further include without limitation a polymerase, a helicase, and an exonuclease.

In some examples, the present invention includes the use of compositions containing polymerase enzymes attached to a scaffold. The scaffold in such examples includes one or more functional elements, and the array regions contain one or more binding elements. In such examples, when the polymerase enzymes attached to the scaffolds are disposed onto a surface containing a plurality of array regions, the functional elements on the scaffold react with one or more binding elements within the array regions. In further examples, the functional elements on the scaffold react with enough of the binding elements within the array regions to thereby prevent other polymerase enzymes attached to scaffolds from occupying the same reaction region. In this way, the plurality of array regions is loaded with single polymerase molecules, generally to a larger percentage than would be expected from a simple Poisson distribution of a dilute solution of polymerase molecules disposed on the surface.

In further examples the present invention includes the use of compositions in accordance with any of the above, in which the scaffold is a star-shaped scaffold. Generally, the core of the scaffold is an organic molecule, although any other type of molecule or composition capable of attachment to multiple functional moieties may be used as the core. In certain non-limiting examples, the core of the scaffold is a multi-arm polyethylene glycol molecule. In still further examples, the core of the scaffold is attached to multiple arms containing biotin moieties attached to DNA molecules. In such examples reaction regions on a surface contain binding elements comprising avidin moieties that are able to react with the biotin moieties on the scaffold attached to the polymerase enzymes to load the polymerase molecules into the reaction regions. In other examples, the multiple arms contain avidin moieties attached to DNA molecules, and the binding elements on the surface then contain biotin moieties that are able to react with the avidin moieties on the scaffold to load the attached polymerase molecules into the reaction regions.

In further examples, the scaffolds of the present invention comprise linear DNA molecules. In some examples, the linear DNA molecules contain multiple functional moieties that are incorporated into the linear DNA molecule through attachment to a nucleobase or through attachment to a flexible linker.

In still further examples, the scaffolds of the present invention may comprise any other materials or shapes in accordance with the present invention. In some non-limiting examples, the scaffolds comprise DNA origami structures, star-shaped structures comprising nucleic acids and/or organic molecules, linear structures, including linear polymeric and/or nucleotide structures, branched structures, and any combination thereof.

In yet further examples, compositions of the present invention include polymerase molecules attached to a scaffold, and these polymerase molecules are also complexed to a single template nucleic acid molecule. In such examples, the polymerase molecule is generally also complexed to the single template nucleic acid molecule. The single template nucleic acid molecule can comprise DNA, RNA, non-natural nucleotides, or a combination thereof. The template nucleic acid may be single stranded or double stranded. In some examples, the template nucleic acid is double stranded with a first end and a second end. In further examples, a first hairpin oligonucleotide connects each strand of the template nucleic acid at the first end, and a second hairpin oligonucleotide connects each strand of the template nucleic acid at the second end. In some examples, the first and second hairpin oligonucleotides are identical (also described herein as symmetrical templates), and in other examples the first and second hairpin oligonucleotides are not the same (also described herein as asymmetrical templates).

As discussed above and in further detail herein, in general, the methods, devices, compositions and systems disclosed herein result in a distribution of polymerase molecules into array regions such that the number of array regions containing only a single polymerase is greater than the number that would be expected from the Poisson distribution resulting from simple application of a dilute solution of polymerase molecules. In certain non-limiting embodiments, about 40-90%, 45-80%, 50-75% or 55-70% of the array regions are occupied by only a single polymerase molecule. In further embodiments, more than 37%, 40%, 45%, 50%, 55%, 60%, 65%, 70%, 75%, 80%, 85%, 90%, 91%, 92%, 93%, 94%, 95%, 96%, 97%, 98%, or 99% of the array regions are occupied by only a single polymerase molecule.

An exemplary non-limiting embodiment of the present invention is schematically depicted in FIG. 1. In FIG. 1, a template nucleic acid 101 is attached to a polymerase 102 which is in turn attached to a scaffold molecule 103. The scaffold molecule comprises functional elements 104, which, as is described in further detail herein, may comprise moieties such as biotin or avidin moieties. The total complex 105 is distributed to a surface comprising array regions—array region 106 is pictured in FIG. 1, but as will be appreciated, a surface may contain several hundreds to thousands of such array regions. The functional elements 104 react with the binding elements 107 within array region 106. The scaffold 103 contains enough functional elements 104 to occupy multiple binding elements within the array region, thus preventing other complexes from entering the same array region. As is discussed in further detail herein, the functional elements and binding elements may comprise any moieties capable of reacting with each other, including biotin-avidin and antibody-antigen pairs.

Figure 19:
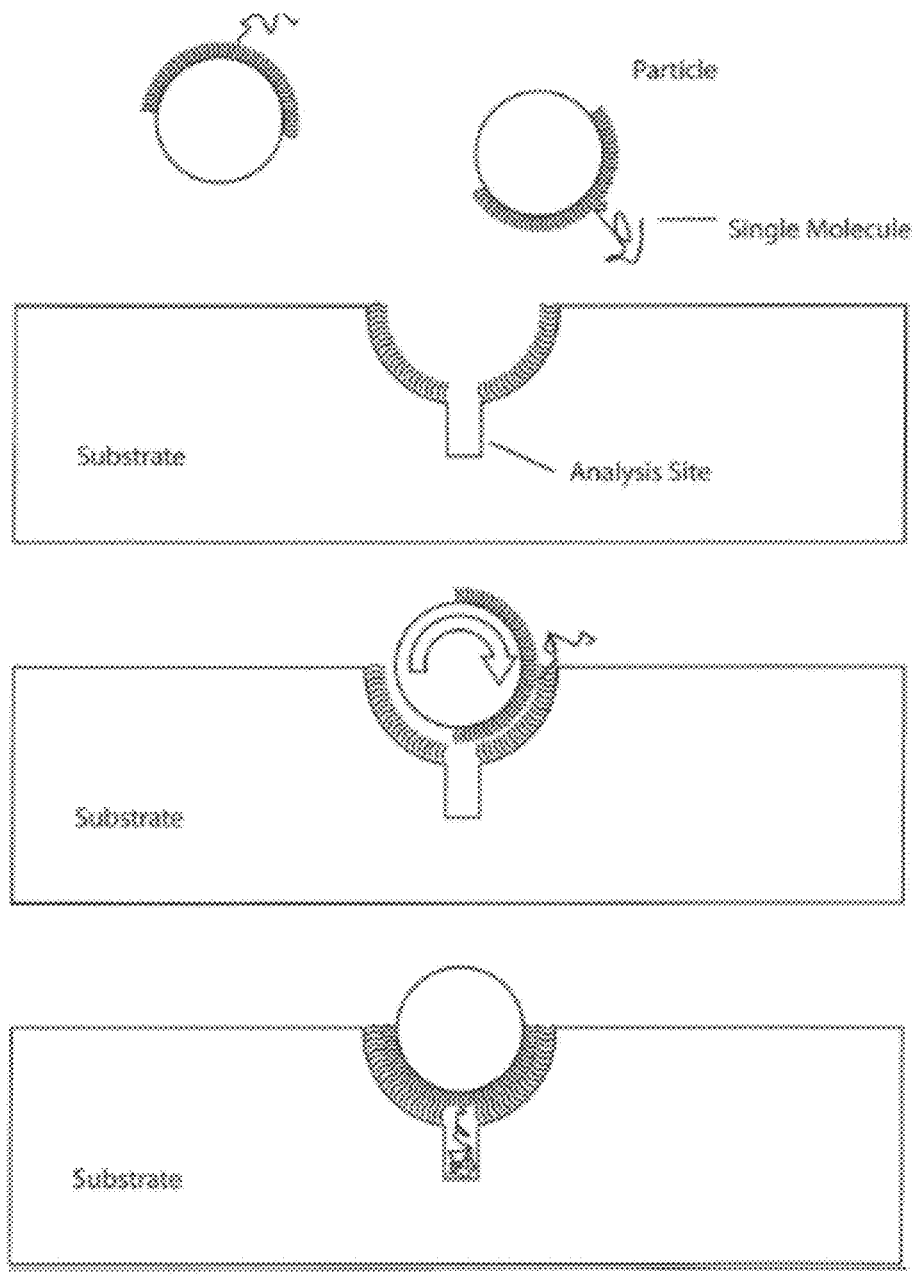
FIG. 19 is a schematic illustration of an embodiment of the invention.
Figure 21:
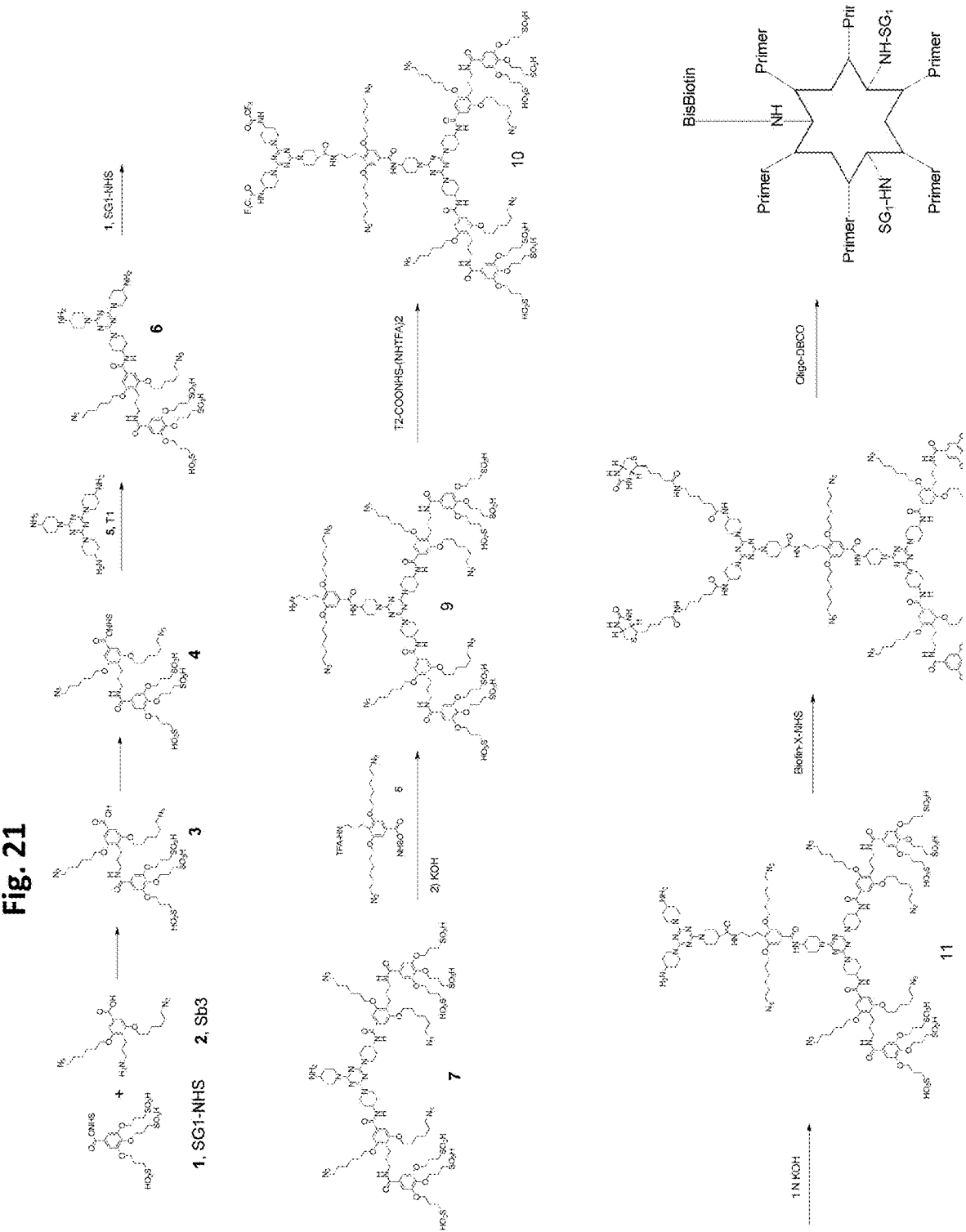
FIG. 21 shows an embodiment of an exemplary preparation scheme of a scaffold of the invention.

In some aspects, methods of super-Poisson loading in accordance with the present invention are particle-based methods utilizing a particle that has two regions: a more hydrophobic region and a less hydrophobic region. These regions are oriented such that when the particle comes into contact with a reaction region, the mutual attraction between the hydrophobic region of the particle and a hydrophobic region in the reaction region minimizes the free energy rotation of the particle, thus maximizing the overlap of contact between the particle and the reaction region. FIG. 19 provides a schematic illustration of an exemplary embodiment of this aspect of the invention.

The above aspects and further exemplary embodiments are described in further detail in the following discussion.

II. Compositions

As discussed in further detail herein, the present invention provides for the loading of reaction regions (which can include without limitation an array of ZMWs) with single polymerase molecules, wherein the number of reaction regions containing a single polymerase molecule is higher than would be expected from a Poisson distribution of a dilute composition.

In certain aspects, the present invention provides compositions comprising polymerase molecules that are attached to scaffolds containing reaction moieties. By "attached to" as referred to herein means covalent attachment, electrostatic interaction, attachment through a linker or some other intervening molecule, or any other method by which the polymerase molecule is connected to the scaffold such that disposing the scaffold in a reaction region also results in depositing the polymerase molecule in that same region. When polymerase molecules attached to scaffolds are distributed into reaction regions, the reaction moieties on the attached scaffolds react with binding sites within the reaction regions. In certain embodiments, the reaction moieties react with enough of the binding sites within the reaction regions to prevent other polymerase molecules from occupying that same reaction region, resulting in single polymerase loading of that reaction region. In other words, the reaction moieties "deplete" the number of available binding sites within a particular reaction region, such that additional scaffolds (and their attached polymerases) are unable to bind in the same reaction region.

In certain embodiments, the compositions of the invention may include a scaffold molecule attached to multiple enzymes attached to a single nucleic acid template. In such embodiments, the scaffold will still prevent other scaffolds from entering the same reaction region by depleting the available binding sites within that region, but the reaction region will contain multiple polymerase molecules attached to the same nucleic acid template. In still further embodiments, scaffolds of the invention may further be attached to nucleic acid templates that comprise single stranded nucleic acid molecules hybridized to one or more primers.

As will be appreciated, a variety of scaffolds can be utilized that contain reaction moieties that react with binding elements in reaction regions. The following sections describe exemplary embodiments of such scaffolds. In addition, the compositions comprising scaffolds attached to the polymerase molecules in accordance with the invention may further include other molecules, including template nucleic acid molecules and/or primers. In some embodiments, the compositions of the invention comprise polymerase molecules attached to scaffolds and further complexed to a single template nucleic acid molecule, generally through attachment to an oligonucleotide (such as a primer oligonucleotide) hybridized to the template nucleic acid molecule.

In general, scaffolds of the invention are of sufficient size to fit within a reaction region and occupy at least a portion of the binding sites within a particular reaction region. As will be appreciated, the scaffolds can thus be designed for the types of reaction regions being used. In exemplary embodiments, the scaffolds are generally of sufficient width to cover at least 90% of the area of the reaction region. In further embodiments, the scaffolds are of sufficient width to cover 50-99%, 55-95%, 60-90%, 65-85%, or 70-80% of the reaction region. In further embodiments in which the reaction regions include arrays of ZMWs, the scaffolds are about 50-200, 75-180, 100-170, 125-160 nm across their widest point—for example, for star shaped scaffolds containing multiple arms described in further detail herein, the widest point will generally be from the end of one arm to the end of another arm located across the core from the first arm. In further embodiments, the scaffolds are generally at least 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 210, 220, 230, 240, 250, 260, 270, 280, 290, or 300 nm across at their widest point.

It should be generally understood that any coupling chemistry, including click chemistry, can be used to assemble compositions in accordance with the descriptions herein. Exemplary methods of producing such compositions, particularly the scaffold components of those compositions, are provided in the Examples herein. Other coupling chemistries may also prove suitable in the compounds of the instant invention, and the element structures should not, therefore, be limited to those illustrated in the exemplified compounds. Accordingly, reactions other than those exemplified in the synthetic schemes described herein, may be suitable for generating the protected reagent compounds of the instant invention. For example, alkylations, e.g., through the reaction of alkyl halides, acylations, and other suitable reactions may be utilized in synthesizing the instant compounds.

Figure 3:
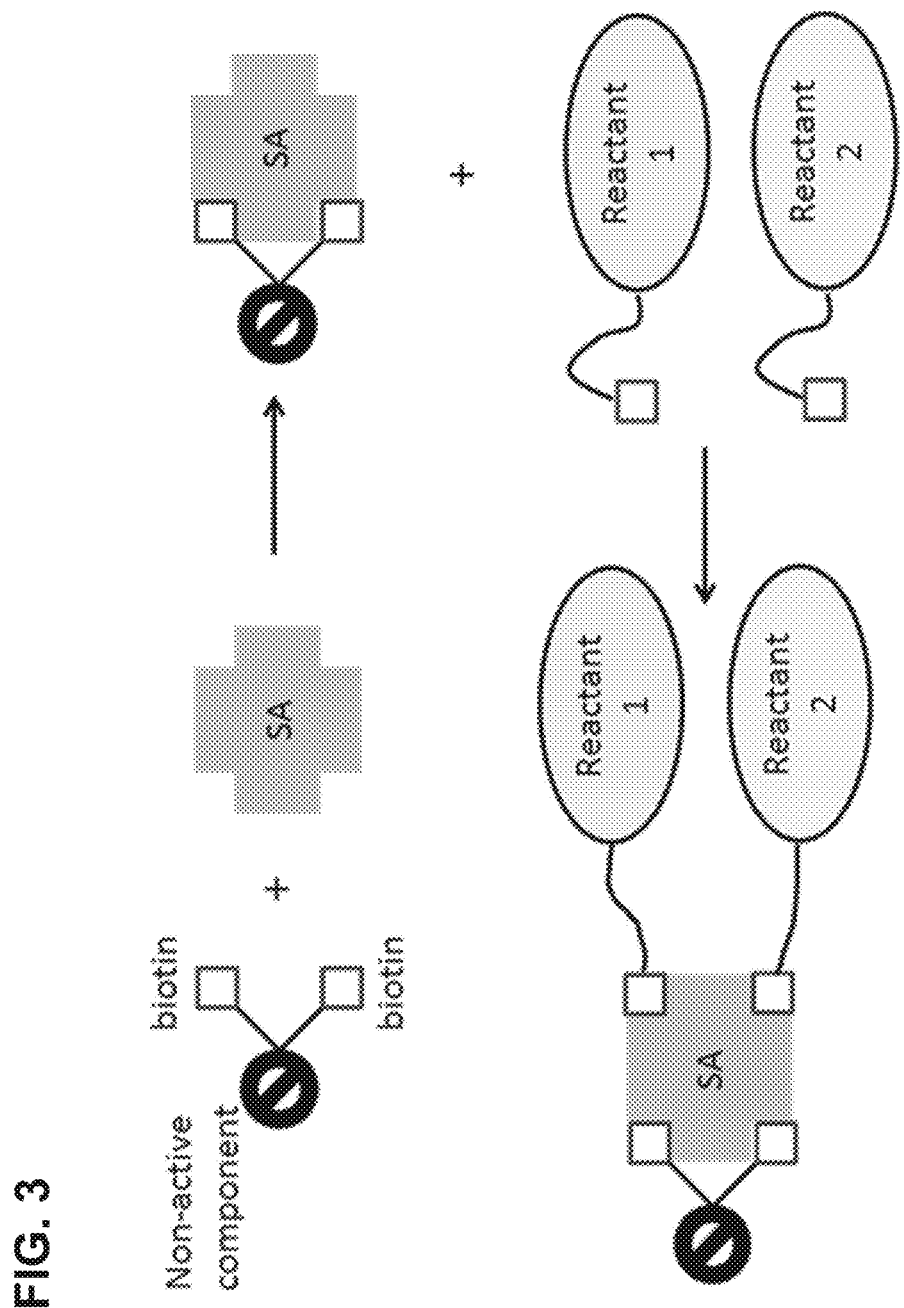
FIG. 3 is a schematic illustration of a tetrameric complex comprising two binding sites blocked by a bis-biotinylated reactant and two binding sites available for further binding.

In some embodiments, compounds of the invention are assembled using biotin tags. Strategies for assembling multiple components of a complex composition that are of use for the scaffolds described herein are described for example in: U.S. patent application Ser. No. 14/452,497 filed Aug. 5, 2014 and U.S. patent application Ser. No. 14/303,296 filed Jun. 12, 2014, the contents of which are incorporated by reference herein in their entirety for all purposes. For example, a bis-biotinylated reactant that is a non-reactive component can serve to block two of the sites on a tetrameric complex. This results in a tetrameric complex having only two binding sites available for further binding as illustrated in FIG. 3. The tetrameric complex bound to the bis-biotinylated reactant can be subsequently used as a divalent binding partner to link together two mono-biotinylated reactants in a 1:1 stoichiometry, which can be the same reactant to produce a homodimer, or different reactants to produce a heterodimer. In the latter case, mixtures of products can be obtained (e.g., comprising both homo- and hetero-dimers) and subsequent purification steps are performed to isolate the desired combination. FIG. 3 illustrates a branched, bis-biotin moiety linked to a non-reactive component, which is exposed to a tetrameric avidin to produce a complex having only two open biotin-binding sites. Two mono-biotinylated reactants (Reactant 1 and Reactant 2) are introduced, either simultaneously or serially, and each binds to one of the open biotin-binding sites. Reactant 1 and 2 can be different reactants, or can be identical reactants, as noted above. This method is especially beneficial when it is desirable to colocalize Reactant 1 and Reactant 2, e.g., to increase the kinetics of a reaction between them. For example, colocalization of two components of a biochemical reaction will promote the reaction by increasing the likelihood the two components will interact with one another, e.g., an enzyme is likely to react more quickly with a colocalized enzyme substrate that an enzyme substrate free in solution. Similarly, where it is desirable to link two reactants together, colocalizing them will facilitate the linkage by increasing their local concentration with respect to each other. Yet further, colocalizing reactants that act in concert, e.g., in a metabolic pathway or as a cofactor/enzyme pair, is beneficial since the colocalization increases the efficiency of their cooperative functions. (These benefits of colocalization apply equally well to other specific embodiments described herein, such as those in which two bis-biotinylated reactants are bound to the same avidin molecule, as further described below.) As noted elsewhere herein, other binding partners can also be used in the compositions and methods described herein. For example, the bis-biotin moiety in FIG. 3 could be replaced with two strep-tag peptides and the avidin could be replaced with a streptactin molecule, e.g., as described in U.S. Pat. No. 7,981,632. Similar strategies further outlined U.S. patent application Ser. No. 14/303,296 filed Jun. 12, 2014 may also be used to produce the compositions described herein.

In certain embodiments, scaffolds of the invention utilize avidin proteins as functional moieties on the arms of the scaffolds or as binding moieties in the reaction regions. These avidin proteins can comprise any avidin proteins known in the art, including without limitation: avidin, streptavidin, tamavidin, traptavidin, xenavidin, bradavidin, AVR2, AVR4, and homologs thereof. In some cases the monomeric, dimeric, or tetrameric forms can be used. In particular, the tetrameric form of the avidin protein in combination with bis-biotin linked components are useful in scaffolds of the present invention. In some cases, glycosylation variants of the avidin proteins are used. In certain embodiments, strategies provided herein use multiple biotin tags for linking a single reactant to a single avidin protein (also referred to herein as "avidin molecule"). Streptavidin is an exemplary avidin protein that has been cloned and studied extensively. See, for example, Argaraña, et al. (1986) Nucleic Acids Res. 14(4): 1871-1882; Aslan, et al. (2007) Journal of Biotechnology 128:213-225; Aslan, et al. (2005) J. Proc. Natl. Acad. Sci. USA 102(24):8507-8512; Baugh, et al. (2010) Biochemistry 49:4568-4570; Gitlin, et al. (1988) Biochem. J. 256:279-282; Hendrickson, et al. (1989) Proc. Nati. Acad. Sci. USA 86:2190-2194; Hyster, et al. (2012) Science 338:500-503; Klumb, et al. (1998) Biochemistry 37(21):7657-63; Kurzban, et al. (1991) J. Biol. Chem. 266(22):14470-14477; Matsumoto, et al. (2011) J. Biotechnology 152:37-42; Sano, et al. (1996) Annals of the New York Academy of Sciences 799 (Enzyme Engineering XIII) pp. 383-390; Schmidt, et al. (1994) Journal of Chromatography A 676:337-345; Srisawat, et al. (2001) RNA 7:632-641; Tahiri-Alaoui, et al. (2002) Nucleic Acids Res. 30(10): e45; Voss, et al. (1997) Protein Engineering 10(8):975-982; and Wilbur, et al. (2004) Bioconjugate Chem. 15:1454-1463, all of which are incorporated herein by reference in their entireties for all purposes. Although many of the compositions, methods, examples, and applications described herein comprise the use or inclusion of streptavidin, e.g., for binding to biotinylated reactants, it will be understood that other avidin proteins (e.g., nucleic acids or other molecules or molecular complexes) can also be used, including without limitations those listed above as well as avidin, deglycoslylated avidin (NeutrAvidin), traptavidin, and variants, mutants, or derivatives thereof. For example, U.S. Pat. No. 7,981,632 describes the "strep-tag" peptide, which binds to a modified version of streptavidin, streptactin. The present invention contemplates using the reagents provided herein in combination with streptactin and/or the strep-tag. For example, streptactin can be substituted for streptavidin in applications where bis-biotin moieties can be bound to streptactin instead of single biotin moieties; alternatively, one or more strep-tag peptides can be linked to a reactant which is subsequently bound to streptactin, or to streptavidin where binding is strong enough. Linking of strep-tags to reactants can be accomplished using conventional molecular biology techniques, cloning, chemical synthesis, and the like. Yet further, peptide and nucleic acid aptamers having an affinity for streptavidin have also been developed and described in the art, e.g., in Tahiri-Alaoui, et al. (2002) Nuc. Ac. Res. 30(10):e45; and Wilson, et al. (2001) Proc. Natl. Acad. Sci. USA 98:3750-3755, both of which are incorporated herein by reference in their entireties for all purposes. Such streptavidin-binding aptamers can be linked to reactants to facilitate binding to streptavidin in a manner similar to the biotin tags described herein. For example, two linked aptamers on a single reactant can operate in a manner similar to a bis-biotin tag and provide a means of linking the reactant to two binding sites on a streptavidin molecule. As such, recitation of streptavidin and biotin in various embodiments herein is merely exemplary and in no way excludes the use of other avidin proteins, either instead of or in combination with streptavidin and/or biotin, in the various aspects of the invention described herein, e.g., methods, compositions, and kits. As such, embodiments are contemplated that comprise different combinations of binding partners in the same complex, e.g., a reactant having a single biotin tag and a single streptavidin-binding aptamer, where the reactant binds to a streptavidin tetramer, with the aptamer bound to one binding site in one dimer of the tetramer, and the biotin bound to the other binding site in the same dimer.

In general, scaffolds discussed herein, including the scaffolds described in the sections below, are attached to polymerase enzymes. In certain embodiments, the scaffolds are attached to polymerase enzyme complexes that further include a template nucleic acid molecule. As described in more detail herein, the scaffold can be attached to a polymerase enzyme through any type of linkage capable of linking two molecules or complexes together. In certain embodiments, the attachment between the scaffold and the polymerase enzyme/polymerase enzyme complex is through a bis-biotin linkage. In certain further embodiments, the linkage is a cleavable linkage between the polymerase and the scaffold such that following the sequencing reaction, the polymerase complex can be removed while retaining the scaffold at the bottom of the ZMW. A second polymerase complex lacking the scaffold could then be introduced and would only have the one binding site in the reaction region (e.g., the location where the first polymerase was before the polymerase complex was removed). Such cleavable linkages are known in the art and can include photocleavable linkers, such as 2-nitrobenzyl linkers (See, e.g., Rodebaugh, R.; Fraser-Reid, B.; Geysen, H. M. Tetrahedron Lett. 1997, 38, 7653-7656), as well as a number of other known photocleavable linker types, see e.g., Org. Lett., 2 (15), 2315-2317, 2000. Such linker chemistries are also described for example in US Patent Pub. Nos. 20070238679 and 20140038178, each of which is hereby incorporated by reference in its entirety for all purposes and in particular for all teachings related to cleavable linkers.

The following exemplary embodiments of scaffolds can be altered without departing from the spirit or scope of the technology hereof, and the compositions discussed in the following sections can be used in any of the methods described in further detail herein.

II.A. Star-Shaped Scaffolds

In some aspects, the compositions of the present invention comprise polymerase molecules attached to a scaffold, where the scaffold comprises a core and multiple arms—the core and the arms together form a "star-shaped" scaffold.

Figure 2A:
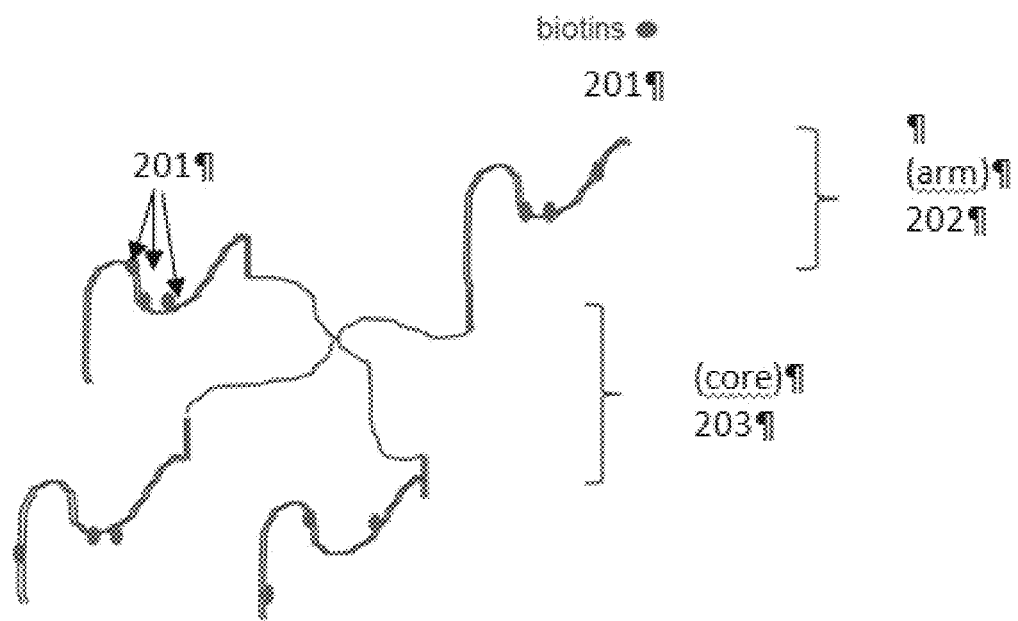
FIG. 2A-FIG. 2B provides schematic illustrations of exemplary scaffolds of the invention.

A schematic illustration of a star-shaped scaffold is provided in FIG. 2A. Generally, star-shaped scaffolds of the present invention comprise a core (203) and multiple arms (202). The multiple arms contain functional moieties (201) that can react with binding moieties (also referred to herein as capture moieties) in a reaction region. The functional moieties may be attached at various points along the arms, as illustrated in FIG. 2A, or in other embodiments, the functional moieties may be located at the ends of the arms. In still further embodiments, the functional moieties may be attached to the arms through any method known in the art, including without limitation through the use of a linker, through NHS ester chemistry, maleimide chemistry, or click chemistry. In yet further embodiments, the functional moieties are themselves part of an oligonucleotide and the arms comprise DNA, and attachment of the functional moieties to the arms is through hybridization between the oligonucleotide and the DNA of the arms.

As described in further detail herein, the reaction between the functional moieties on any of the scaffolds described herein, including star-shaped scaffolds, and binding moieties on the reaction region help to load single scaffolds into the reaction region (and anything attached to those scaffolds) and prevent other scaffolds from loading into the same reaction region. In accordance with any of the above, the functional moieties may comprise biotin moieties and the binding moieties may comprise avidin, or vice versa.

In certain non-limiting aspects, the core of the scaffold is any molecule or composition capable of supporting multiple arms. In some embodiments, the core of the scaffold is an organic molecule or a protein. In further embodiments, wherein the core comprises a member selected from the group consisting of: an organic molecule, a multi-binding site protein, a branched peptide, a branched carbohydrate (such as cyclodextrin) and a branched oligonucleotide. In further exemplary embodiments, the core of the scaffold is a multi-arm polyethylene glycol molecule. In certain embodiments, the core contains adaptors that can then be attached to arms. In the exemplary embodiment of a core comprising a multi-arm polyethylene glycol (PEG) molecule, the arms of the PEG further comprise adapters that can be used to attach the PEG molecule to other molecules, which, as is described below, form the "multiple arms" of the scaffold.

In further aspects, the multiple arms of star-shaped scaffolds of the invention comprise linkers attaching the functional moieties to the core. These linkers may comprise any type of molecule capable of joining the functional moieties to the core, including without limitation organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In some embodiments, alkyl, e.g., alkane, alkene, alkyne alkoxy or alkenyl, or ethylene glycol linkers are used. In certain exemplary embodiments, the arms of the star-shaped scaffold comprise a DNA molecule (for example an oligonucleotide) containing one or more functional moieties, and those DNA molecule arms may further be attached directly to the core or through an intermediate adapter.

As will be appreciated, the star-shaped scaffolds can contain any number of arms that is of use in the methods described herein. In some non-limiting embodiments, the star-shaped scaffolds of the invention comprise at least 2, 3, 4, 5, 6, 7, 8, 9, or 10 arms. In further embodiments, the star-shaped scaffolds comprise about 2-6, 3-10, 5-30, 7-25, 9-20, or 11-15 arms. As discussed above, the arms generally comprise functional moieties capable of reacting with binding moieties in reaction regions. In certain embodiments, the arms comprise biotin or avidin moieties. In further embodiments, each of the multiple arms of the star-shaped scaffolds comprise around 5-40 functional moieties. In still further embodiments, the arms individually comprise about 5-50, 10-45, 15-40, 20-35, or 25-30 functional moieties. In yet further embodiments, the star-shaped scaffolds of the invention comprise at least 10, 15, 20, 25, 30, 35, 40, 45, 50, 55, or 60 functional moieties on each of the multiple arms.

As will be appreciated, the star-shaped scaffolds can be of any size, depending on the design of the core and the multiple arms. In certain exemplary embodiments and as is discussed above, star-shaped scaffolds are generally of sufficient width to cover at least 90% of the area of the reaction region. In further embodiments in which the reaction regions include arrays of ZMWs, the scaffolds are about 50-200, 75-180, 100-170, 125-160 nm across their widest point—for star shaped scaffolds, the widest point will generally be from the end of one arm to the end of another arm located across the core from the first arm. In further embodiments, the scaffolds are generally at least 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 210, 220, 230, 240, 250, 260, 270, 280, 290, or 300 nm across at their widest point.

In some embodiments, the arms comprise oligonucleotides, and these oligonucleotides can be of any length to provide the desired final width for the scaffold. In some embodiments, each arm is about 500-2000 basepairs in length. In further embodiments, each arm is about 200-2500, 300-2400, 400-2300, 500-2200, 600-2100, 700-2000, 800-1900, 900-1800, 1000-1700, 1100-1600, 1200-1500, 1300-1400 basepairs in length. In still further embodiments, each arm is at least 450, 550, 650, 750, 850, 950, 1050, 1150, 1250, 1350, 1450, 1550, 1650, 1750, 1850, 1950, 2050 basepairs in length.

Figure 2B:
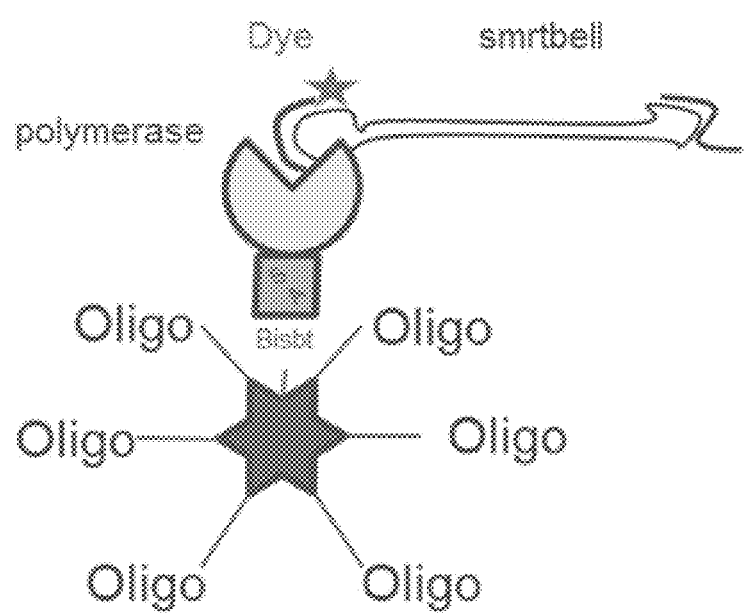

In general, the star-shaped scaffolds of the invention are attached to polymerase enzymes. In certain embodiments, the scaffolds are attached to polymerase enzyme complexes that further include a template nucleic acid molecule. In exemplary embodiments, the star-shaped scaffold is attached to a polymerase enzyme through a bis-biotin linkage between the core of the scaffold and the polymerase enzyme—an illustration of such an embodiment is provided in FIG. 2B. In further embodiments, the polymerase enzyme is further complexed to a template nucleic acid molecule (also referred to herein as a "template sequence"). As discussed in further detail herein, in some cases, the template sequence may be a linear single or double stranded nucleic acid sequence. In some embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, alternate functional circular constructs are also described in US Pat. App. Pub. No. 20090298075 the full disclosures of each of which are incorporated herein by reference in their entirety for all purposes and in particular for all teachings related to template nucleic acid constructs.

In certain exemplary aspects, the core of the scaffold is attached to multiple arms containing biotin moieties attached to DNA molecules, and in such examples the reaction regions on the surface contain binding elements comprising avidin moieties that are able to react with the biotin moieties on the scaffold attached to the polymerase enzymes to load the polymerase molecules into the reaction regions. In other examples, the multiple arms contain avidin moieties attached to DNA molecules, and the binding elements on the surface then contain biotin moieties that are able to react with the avidin moieties on the scaffold to load the attached polymerase molecules into the reaction regions.

In certain embodiments, star-shaped scaffolds of the invention are not dendrimers—in other words, the star-shaped scaffolds of the invention are not repetitively branched tree-like structures, but are instead discrete molecules that include a core and a set of multiple arms, where the core is comprised of a material that is different from that of the multiple arms.

Without being limited by mechanism, one advantage of the star-shaped scaffolds of the present invention is that the functional moieties are separated by a distance that makes depletion of the binding moieties within the reaction region more efficient than is the case if the functional moieties are located more closely to each other. This may be particularly possible in the case of the star-shaped scaffolds, because the functional moieties are generally located on flexible arms, allowing for increased mobility and rotational freedom to efficiently occupy and deplete binding moieties within the reaction region, thus preventing multiple scaffolds from occupying the same reaction region. Furthermore, the star-shaped scaffold enables coverage of a large reaction region with relatively short arm length. This speeds up binding kinetics and places the enzyme in closer proximity to the surface of the substrate, providing increased control over and intensity of signal strength for detection.

Another unexpected advantage of the star-shaped scaffolds of the present invention is that even the scaffolds comprising multiple proteinaceous functional moieties nevertheless do not show significant amounts of aggregation of the scaffolds in solution. This provides the advantage of efficient loading of single scaffolds into the reaction regions with minimal loss of reactants to aggregation.

II.B. Other Types of Scaffolds

In addition to the star-shaped scaffolds discussed above, other types of scaffolds are encompassed by the present invention.

In some aspects, the scaffolds are linear DNA molecules containing one or more functional moieties that are incorporated into the linear DNA molecule through attachment to a nucleobase or through attachment to a flexible linker. These one or more functional moieties and their attached linkers are also referred to herein as "branches" of the linear DNA molecule. In further embodiments, the functional moieties are biotin or avidin moieties. In still further embodiments, the linkers comprise polymeric structures, including without limitation polyethylene glycol, a peptide, an oligonucleotide, and an aliphatic carbon chain. In yet further embodiments, these linkers may be attached to the linear DNA structure through a modified base, and such modified bases can include without limitation aminoallyl-dT, aminopropargyl-dT, thiol-phosphate, thiol-modified base, azide modified base, and an alkyl-modified base.

In further embodiments, the linkers are increased in size and/or number to produce a highly "branched" linear DNA structure. These branched linear scaffolds are designed to enhance the flexibility of the scaffold and improve coverage of the reaction regions. DNA backbones are known to be rigid, with a persistence length of about 30-50 nm. By maintaining a distance between the functional moieties and the DNA backbone with a flexible linker (branch), the functional moieties are thereby more accessible to the binding sites on surface. Such linkers can include without limitation polymers, amino acids, and alkyl chains. In further embodiments, such linkers include polyethylene glycol, peptides, oligonucleotides, and aliphatic carbon chains. The linkers are in certain embodiments attached to the DNA via a modified base such as aminoallyl-dT, aminopropargyl-dT, thiol-phosphate, thiol-modified base, azide modified base, or alkyl-modified base.

In certain embodiments, the linear DNA scaffold is a DNA molecule with biotin or avidin moieties attached to the DNA chain. Such scaffolds can be produced using methods known in the art for attaching moieties to DNA molecules. As an example, biotin- or avidin-dUTP can be spiked into a PCR reaction with different percentages, and polymerase would incorporate the biotins to the DNA chain. Alternatively, amine-labeled base or thiol-labeled bases can be incorporated, and avidin or biotin can be attached though amine-NHS ester chemistry or thiol-maleimde reaction.

For linear DNA scaffolds, the DNA backbone length can be modified by primer design, and the number of functional moieties can be controlled by the ratio of UTP's bound to functional moieties relative to native TTPs that are included in the synthesis reaction. By selecting the sequence of template, one can also manipulate the density of functional moieties along the DNA chain. For example, one could make DNA with higher biotin density in the center region versus the ends of the DNA backbone, and vice versa.

In some embodiments, the branches of the linear DNA scaffolds (e.g., the linkers connecting the functional moieties to the DNA backbone) are from about 0.2-5 nm in length. In further embodiments, the branches are about 0.2-4.5, 0.4-4, 0.5-3, 0.6-3.5, 0.8-3.0, 1.0-2.5, or 1.2-2 nm in length. In yet further embodiments, the branches are less than 1 nm in length. In still further embodiments, the branches are at least 2 nm in length.

In other aspects, scaffolds of the invention comprise a DNA origami structure. In such aspects, functional moieties, including without limitation avidin and biotin moieties, are introduced as tags on an oligonucleotide, either at the end of an oligonucleotide or inserted through a modified base. In certain embodiments, structures are produced by hybridizing short DNA segments to form a predetermined structure. The size of the origami structure can be designed to fit a reaction region (including without limitation a ZMW) so that additional DNA origami scaffolds (and their attached polymerase complexes) cannot occupy a reaction region both through occupation of the binding moieties in the reaction region by the functional moieties of the scaffold as well as by steric hindrance. Any DNA origami structures known in the art are of use in the present invention, including triangle-shaped DNA origami structures as well as those for example described in Rothemund, Nature 440: 297-302 (2006), Douglas et al., Nature 459:414-418 (2009); Dietz, Science 325: 725-730 (2009), and U.S. Pat. No. 8,877,438, each of which is hereby incorporated by reference in its entirety for all purposes and in particular for all description, figures, and figure legends related to DNA structures, particularly those structures referred to as DNA origami. As is known in the art, if the proper nucleic acid components are mixed together, they self-assemble into structures (commonly referred to as "DNA origami") with a selected size and geometry. In certain embodiments, one could use the method of "scaffolded DNA origami" (Rothemund (2006) "Folding DNA to create nanoscale shapes and patterns" Nature 440: 16) to create arbitrary two-dimensional DNA origami shapes. Two such shapes, such as a flat circle and a rectangle that has been stapled together at each side to form a hollow cylinder, can be combined together to form a "cup and coaster" shape. This "cup and coaster" DNA origami can be designed to be approximately the same size as a ZMW or other array region of interest. Such structures can also be designed to have a binding site for a polymerase or other analyte, leading to delivery of a single analyte to an array site of interest (e.g., to a ZMW).

Additional DNA structures can also be adapted to the present invention for delivery of a single polymerase molecule to an array site of interest. Such self-assembling DNA structures include, e.g., DNA grids (Park et al. (2006) "Finite-Size, Fully Addressable DNA Tile Lattices Formed by Hierarchical Assembly Procedures" Angew. Chem. Int. Ed. 45:735-739), DNA Dodecahedrons (Zhang et al. (2008) "Conformational flexibility facilitates self-assembly of complex DNA nanostructures PNAS 105(31):10665-10669; Zimmermann et al. (2007) "Self-Assembly of a DNA Dodecahedron from 20 Trisoligonucleotides with C3h Linkers" Angewandte Chemie International Edition, doi: 10.1002/anie.200702682), icosahedra and nanocages (Zhang et al. (20080 "Conformational flexibility facilitates self-assembly of complex DNA nanostructures" PNAS 105 (31)10665-10669), Sierpinski triangles (Rothemund et al. (2004) "Algorithmic Self-Assembly of DNA Sierpinski Triangles", PLoS Biol 2(12): e424), DNA Octahedrons (Andersen et al., (2008) "Assembly and structural analysis of a covalently closed nanoscale DNA cage" Nucleic Acids Research 36(4): 1113-1119), DNA grids formed with gold particles (Zhang et al. (2006) "Periodic Square-Like Gold Nanoparticle Arrays Templated by Self-Assembled 2D DNA Nanogrids on a Surface" Nano Lett. 6(2): 248-251), and ladder-shaped polycatenanes (Weizmann et al. (2008) "A polycatenated DNA scaffold for the one-step assembly of hierarchical nanostructures" PNAS 105(14) 5289-5294), each of which is hereby incorporated by reference in its entirety for all purposes and in particular for any teachings related to building DNA structures that could be used as scaffolds in accordance with the present invention.

II.C. Template Molecules

Any of the methods and complexes described herein can utilize template nucleic acid molecules (also referred to herein as "template sequences"). In general, the template nucleic acid is the molecule for which the complimentary sequence is synthesized in the polymerase reaction. In some cases, the template nucleic acid is linear; in some cases, the template nucleic acid is circular. The template nucleic acid can be DNA, RNA, or can be a non-natural RNA analog or DNA analog. Any template nucleic acid that is suitable for replication by a polymerase enzyme can be used herein.

In some embodiments, the template nucleic acids used in methods and compositions of the present invention comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (i.e. in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In further embodiments, nucleic acid molecules are obtained from a sample and fragmented for use in methods of the invention as template nucleic acids. The fragments may be single or double stranded and may further be modified in accordance with any methods known in the art and described herein. Template nucleic acids may be generated by fragmenting source nucleic acids, such as genomic DNA, using any method known in the art. In one embodiment, shear forces during lysis and extraction of genomic DNA generate fragments in a desired range. Also encompassed by the invention are methods of fragmentation utilizing restriction endonucleases.

As will be appreciated, the template nucleic acids may be generated from a source nucleic acid, such as genomic DNA, by fragmentation to produce fragments of a specific size. The target nucleic acids can be, for example, from about 10 to about 50,000 nucleotides in length, or from about 10 to about 20,000 nucleotides in length. In one embodiment, the fragments are 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length.

In some aspects, the nucleic acids used in the compositions and methods of the present invention comprise nucleoside polyphosphates (also referred to herein as "nucleotides" "nucleotide analogs" or "nucleoside polyphosphate analogs") that have a three or more phosphate groups. In exemplary embodiments, nucleotide analogs of use in methods of the invention have at least 4, 5, 6, 7, 8, 9, 10, 11, 12, 13, 14, 15, 16, 17, 18, 19, 20, 21, 22, 23, 24, 25, 26, 27, 28, 29, 30 phosphate groups. In further exemplary embodiments, nucleotide analogs of use in methods of the invention have about 4, 5, 6, 7, 8, 9, 10, 11, 12, 13, 14, 15, 16, 17, 18, 19, 20, 21, 22, 23, 24, 25, 26, 27, 28, 29, 30 phosphate groups. In still further exemplary embodiments, nucleotide analogs of the invention have from about 4-60, 5-55, 6-50, 7-45, 8-40, 9-35, 10-30, 11-25, 12-20, 13-15, 4-20, 4-12, 5-19, 6-18, 7-17, 8-16, 9-15, 10-14, 11-13 phosphate groups.

In some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, alternate functional circular constructs are also described in US Pat. App. Pub. No. 20090298075 the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In further aspects, the template nucleic acid used in the compositions of the present invention includes: a double stranded nucleic acid segment having a first and second end; a first hairpin oligonucleotide connecting each strand of the single template nucleic acid at the first end; a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In further embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In other embodiments, the capture adapter comprises at least one methoxy residue. In further embodiments, the capture adapter is complementary to an oligonucleotide attached to a bead, which can in further embodiments be a magnetic bead that can be used to enrich a population for template nucleic acids containing the capture adapter.

In still further embodiments, the first or second hairpin comprises a self-primed adapter sequence in which the primer is part of the adapter. In such embodiments, an additional oligonucleotide primer is not needed to allow a polymerase molecule to begin replicating the template.

In further embodiments and in accordance with any of the above, the nucleotide analogs of use in the present invention include 4 or more phosphate groups as discussed above and in addition include a terminal protecting group (also referred to herein as a "terminal blocking group") to protect the nucleotide analog from degradation until the nucleotide analog is incorporated and the polyphosphate chain is released, for example in one or more of the template-directed polymerization reactions in the stepwise and single molecule sequencing reactions discussed herein. The protecting group will in general be on the terminal phosphate of the polyphosphate chain of the nucleotide analog and can be any type of protecting group that prevent a hydrolysis reaction, such as a reaction by a phosphatase. In some embodiments, the nucleoside polyphosphate is protected by another nucleoside of the same base (e.g., a symmetric dinucleoside polyphosphate). In one non-limiting embodiment, the protecting group includes any group that takes the place of one or more of the oxygen atoms of the terminal phosphate group to prevent degradation. In further exemplary embodiments, the protecting group comprises a linker, an alkyl group (including without limitation a methyl, ethyl, propyl or butyl group), a dye, any other adduct (including without limitation a fluorophore, a carbohydrate, and an aromatic group) that is attached either to the P or an O in the terminal phosphate. In embodiments in which the protecting group is a linker, the linker can be any molecular structure, including without limitation organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In some embodiments, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes and in particular for all teachings related to linkers. The protecting groups may in further embodiments be alkyl, aryl, or ester linkers. The protecting groups may also be amino-alkyl linkers, e.g., amino-hexyl linkers. In some cases, the linkers can be rigid linkers such as disclosed in U.S. patent application Ser. No. 12/403,090, which is incorporated herein by reference in its entirety for all purposes and in particular for all teachings related to linkers.

In addition to the naturally occurring "nucleobases," adenine, cytosine, guanine and thymine (A, C, G, T), nucleic acid components of the compounds of the invention optionally include modified bases. These components can also include modified sugars. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine. The dye of the invention or another probe component can be attached to the modified base.

In further embodiments, the nucleotide analogs of the present invention may further include labels, such as fluorescent labeling groups. These labeling groups may also be such that the different types of nucleotide analogs may be distinguished from one another. In such embodiments, typically, each of the different types of nucleotide analogs will be labeled with a detectably different fluorescent labeling group, e.g., that possesses a detectably distinct fluorescent emission and/or excitation spectrum, such that it may be identified and distinguished from different nucleotides upon incorporation. For example, each of the different types of nucleotides, e.g., A, T, G and C, will be labeled with a fluorophore having a different emission spectrum. For certain embodiments, the nucleotide may include a fluorescent labeling group coupled to a portion of the nucleotide that is incorporated into the nascent nucleic acid strand being produced during synthesis, e.g., the nucleobase or sugar moiety. Nucleotide compositions having fluorophores coupled to these portions have been previously described (See, e.g., U.S. Pat. Nos. 5,476,928 and 4,711,955 to Ward et al.). As a result of the label group being coupled to the base or sugar portion of the nucleotide, upon incorporation, the nascent strand will include the labeling group. This labeling group may then remain or be removed, e.g., through the use of cleavable linkages joining the label to the nucleotide (See, e.g., U.S. Pat. No. 7,057,026). A variety of different fluorophore types, including both organic and inorganic fluorescent materials, have been described for biological applications and are likewise applicable in the instant invention.

In further embodiments, nucleotide analogs of the present invention may include nucleoside polyphosphates having the structure:

B-S-P-G, wherein B is a natural or non-natural nucleobase, S is selected from a sugar moiety, an acyclic moiety or a carbocyclic moiety, P is a modified or unmodified polyphosphate, and G is a protecting group.

The base moiety, B, incorporated into the nucleotide analogs of the invention is generally selected from any of the natural or non-natural nucleobases or nucleobase analogs, including, e.g., purine or pyrimidine bases that are routinely found in nucleic acids and nucleic acid analogs, including adenine, thymine, guanine, cytidine, uracil, and in some cases, inosine. For purposes of the present description, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes and in particular for all teachings related to nucleobases and labeling nucleobases.

In some embodiments, for the nucleotide analogs used in the invention, the S group is generally a sugar moiety that provides a suitable backbone for a synthesizing nucleic acid strand. In it most preferred aspect, the sugar moiety is selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties may be incorporated as the "S" group in place of a sugar moiety, including, e.g., those described in published U.S. Patent Application No. 2003/0124576, incorporated herein by reference in its entirety for all purposes and in particular for all teachings related to sugar moieties of nucleotides and nucleotide analogs.

The P groups in the nucleotides of the invention are modified or unmodified polyphosphate groups. As discussed above, the number of phosphates in the polyphosphate can have 4, 5, 6, 7, 8, 9, 10, 11, 12, 13, 14, 15, 16, 17, 18, 19, 20, 21, 22, 23, 24, 25, 26, 27, 28, 29, 30 phosphate groups or more modified or unmodified phosphates. The unmodified phosphates have linearly linked —O—P(O)$_2$— units, for example a tetraphosphate, pentaphosphate, hexaphosphate, heptaphosphate, or octaphosphate. The P groups also include modified polyphosphates, for example by virtue of the inclusion of one or more phosphonate groups, effectively substituting a non-ester linkage in the phosphorous containing chain of the analog, with a more stable linkage. Examples of preferred linkages include, e.g., $CH_2$, methylene derivatives (e.g., substituted independently at one or more hydrogens with F, Cl, OH, $NH_2$, alkyl, alkenyl, alkynyl, etc.), $CCl_2$, $CF_2$, NH, S, $CH_2CH_2$, $C(OH)(CH_3)$, $C(NH_2)[(CH_2)_6CH_3]$, CH(NHR) (R is H or alkyl, alkenyl, alkynyl, aryl, $C(OH)[(CH_2)_nNH_2]$ (n is 2 or 3), and $CNH_2$. In particularly preferred aspects, methylene, amide or their derivatives are used as the linkages.

Other P groups of the invention have phosphate or modified phosphates in which one or more non-bridging oxygen is substituted, for example with S, or $BH_3$. In one aspect of the invention, one or more, two or more, three or more, or four or more non-bridging oxygen atoms in the P group has an S substituted for an O. The substitution of, sulfur atoms for oxygen can change the polymerase reaction kinetics such that a system having two slow steps can be selected. While not being bound by theory, it is believed that the properties of the nucleotide, such as the metal chelation properties, electronegativity, or steric properties are the nucleotide can be altered by the substitution of non-bridging oxygen for sulfur in P. In some cases, it is believed that the substitution of two or more non-bridging oxygen atoms with sulfur can affect the metal chelation properties so as to lead to a change in the kinetics of incorporation, which can be used to modulate the signals generated from the incorporation events discussed herein.

Suitable nucleotide analogs include analogs in which sulfur is substituted for one of the non-bridging oxygens. In some embodiments, the single sulfur substitution is made such that substantially only one stereoisomer is present. The nucleotide can have multiple phosphates in which one or more of the phosphates has a non-bridging sulfur in place of oxygen. The substituted phosphate in the nucleotide can be the R or the S stereoisomer.

G generally refers to a protecting group that is coupled to the terminal phosphorus atom via the $R_4$ (or $R_{10}$ or $R_{12}$) group. As discussed above, the protecting groups employed in the analogs of the invention may comprise any of a variety of molecules, including a linker, an alkyl group (including without limitation a methyl, ethyl, propyl or butyl group), any other adduct (including without limitation a fluorophore, a carbohydrate, and an aromatic group) or a label e.g., optical labels, e.g., labels that impart a detectable optical property to the analog, electrochemical labels, e.g., labels that impart a detectable electrical or electrochemical property to the analog, physical labels, e.g., labels that impart a different physical or spatial property to the analog, e.g., a mass tag or molecular volume tag. In some cases individual labels or combinations may be used that impart more than one of the aforementioned properties to the nucleotide analogs of the invention.

The protecting group may be directly coupled to the terminal phosphorus atom of the analog structure, in alternative aspects, it may additionally include a linker molecule to provide the coupling through, e.g., an alkylphosphonate linkage. A wide variety of linkers and linker chemistries are known in the art of synthetic chemistry may be employed in coupling the labeling group to the analogs of the invention. For example, such linkers may include organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes. Additionally, such linkers may be selectively cleavable linkers, e.g., photo- or chemically cleavable linkers or the like. The linkers can be alkyl, aryl, or ester linkers. The linkers can be, amino-alkyl linkers, e.g., amino-hexyl linkers. In some cases, the linkers can be rigid linkers such as disclosed in U.S. patent application Ser. No. 12/403,090.

The B, S, P, and G groups can be connected directly, or can be connected using an linking unit such as an —O—, —S—, —NH—, or —$CH_2$— unit.

II.D. Polymerases

The methods and compositions of the present invention utilize polymerase enzymes (also referred to herein as "polymerases"). As discussed above, polymerase enzymes are often part of or complexed with the scaffolds of the invention. Any suitable polymerase enzyme can be used in the systems and methods disclosed herein. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions of the present invention are strand-displacing polymerases.

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of φ29, a preferred type of parental enzyme to be modified according to the invention, is available.

In addition to wild-type polymerases, chimeric polymerases made from a mosaic of different sources can be used. For example, φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the methods known in the art to decrease branching fraction formation, improve stability of the closed polymerase-DNA complex, and/or alter reaction rate constants. In some cases, the polymerase is modified in order to more effectively incorporate the nucleotide analogs of the invention, e.g. analogs having four or more phosphates in their polyphosphate chain, and/or nucleotide analogs having terminal groups to prevent phosphate cleavage by phosphatase enzymes. Enzymes mutated to more readily accept nucleotide analogs having such properties are described, for example in the applications described above and in US 20120034602—Recombinant Polymerases for Improved Single Molecule Sequencing; US 20100093555—Enzymes Resistant to Photodamage; US 20110189659—Generation of Modified Polymerases for Improved Accuracy in Single Molecule Sequencing; US 20100112645—Generation of Modified Polymerases for Improved Accuracy in Single Molecule Sequencing; US 2008/0108082—Polymerase enzymes and reagents for enhanced nucleic acid sequencing; and US 20110059505—Polymerases for Nucleotide Analogue Incorporation which are incorporated herein by reference in their entirety for all purposes.

Many polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, φ29-related polymerases including wild type φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified φ29-type DNA polymerase. For example, the modified recombinant DNA polymerase can be homologous to a wild-type or exonuclease deficient φ29 DNA polymerase, e.g., as described in U.S. Pat. No. 5,001,050, 5,198,543, or 5,576,204. Alternately, the modified recombinant DNA polymerase can be homologous to other φ29-type DNA polymerases, such as B103, GA-1, PZA, φ15, BS32, M2Y, Nf, G1, Cp-1, PRD1, PZE, SF5, Cp-5, Cp-7, PR4, PR5, PR722, L17, φ21, or the like. For nomenclature, see also, Meijer et al. (2001) "φ29 Family of Phages" Microbiology and Molecular Biology Reviews, 65(2):261-287. Suitable polymerases are described, for example, in U.S. patent application Ser. No. 12/924,701, filed Sep. 30, 2010; and Ser. No. 12/384,112, filed Mar. 30, 2009.

In further embodiments, the polymerase enzyme used in the methods of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

The polymerase enzymes of use in the present invention generally require a primer, which is usually a short oligonucleotide that is complementary to a portion of the template nucleic acid. The primers can comprise naturally occurring RNA or DNA oligonucleotides. The primers may also be synthetic analogs. The primers may have alternative backbones as described above for the nucleic acids of the invention. The primer may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. The primer can also be selected to influence the kinetics of the polymerase reaction.

III. Methods of Distributing Single Polymerase Molecules into Reaction Regions In certain aspects, the compositions described herein are used in methods of loading polymerase molecules into reaction regions (also referred to herein as "array regions"). In particular aspects, these methods result in a plurality of the reaction regions containing only a single polymerase molecule. In further embodiments, the percentage of reaction regions containing only a single polymerase molecule as a result of methods of the invention is higher than what would be expected from a Poisson distribution when simply relying on a passive diffusion-based mechanism. Passive diffusion-based mechanisms of loading have a theoretical limit of 37% of the array regions being loaded with a single polymerase molecule under the Poisson distribution. The methods and compositions described herein allow for an increased percentage of single-loaded reaction regions over the theoretical limit governed by the Poisson distribution.

As will be appreciated, the reaction regions can comprise any space delimited region on the surface of a substrate into which the compositions described herein can be distributed. In some embodiments, the reaction regions are wells on a planar surface. In further embodiments, the reaction regions comprise an array of ZMWs.

In certain non-limiting embodiments, methods of loading compositions in accordance with the present invention result in about 40-90%, 45-80%, 50-75% or 55-70% of the reaction regions occupied by only a single polymerase molecule. In further embodiments, more than 37%, 40%, 45%, 50%, 55%, 60%, 65%, 70%, 75%, 80%, 85%, 90%, or 95% of the array regions are occupied by only a single polymerase molecule. As has been described in further detail herein, the single polymerase molecule is generally attached to a scaffold of the invention, and that scaffold aids in the distribution of the single polymerase molecules of the invention into reaction regions by depleting binding moieties within the reaction regions, thereby preventing additional molecules from occupying the same reaction region.

In general, methods of the present invention utilize compositions comprising a polymerase molecule complexed with and/or attached to a scaffold that includes functional moieties. These functional moieties are generally capable of reacting to binding moieties in the array regions, and by occupying enough of those binding moieties, the compositions are able to effectively block other polymerase molecules and their scaffolds from loading into the same array region. As discussed in further detail above, these scaffolds can comprise any shape or size, and in some non-limiting examples are star-shaped structures, linear DNA structures, and DNA origami structures. In still further embodiments, the functional moieties on the scaffold comprise biotin moieties and the binding moieties in the array regions comprise avidin. In other embodiments, the functional moieties on the scaffold comprise avidin moieties and the binding moieties in the array regions comprise biotin. In still other embodiments, the functional moieties and binding moieties comprise any pair that can react with each other, including without limitation antigen-antibody binding pairs, receptor-ligand binding pairs, aptamer-epitope binding pairs, GST/glutathione pairs, nucleic acid hybridization pairs, and the like.

In some aspects, the compositions of the invention are applied in a solution to a surface comprising array regions and the array regions are loaded with single compositions through simple diffusion. In further embodiments, the array regions are loaded with single compositions with the use of beads. Such beads may be attached to or complexed with any part of the compositions described herein, including the polymerase, the scaffold, or the template nucleic acid. Depositing with beads can lead to a more even distribution of deposited compositions by size than can be the case when relying on diffusion of the compositions alone, allowing for a more comprehensive representation of the larger size fragments in the data in any subsequent single molecule analyses. In some embodiments, the beads aid in the distribution of single compositions into the array regions by improving the kinetics of moving the compositions from solution to the surface of the substrate at which point gravity and diffusion further aid in the disposition of the compositions into the array regions themselves. Additional compositions are generally prevented from entering the same array regions because the functional moieties on the scaffold deplete the available binding moieties in the array regions, leaving no further binding moieties for occupation by a second scaffold.

In further aspects, the scaffolds and their attached polymerase-nucleic acid complexes are attached to a magnetic bead, and that magnetic bead is used to aid in loading of the scaffolds into the reaction regions through application of a magnetic field. In some embodiments, the magnetic bead is attached via hybridization between an oligonucleotide attached to the magnetic bead and a sequence on the template nucleic acid. In further embodiments the magnetic bead is attached to a hook oligonucleotide comprising a retrieval sequence that is complimentary to an oligonucleotide attached to the magnetic bead and a capture sequence that is complementary to the template nucleic acid. Methods of making and using such hook oligonucleotides are described in for example, in U.S. Pat. No. 8,715,930, which is hereby incorporated by reference in their entirety for all purposes, and in particular for all written description, figures and figure legends related to hook oligonucleotides and any other methods related to capture of selected molecules and complexes. In still further embodiments, the oligonucleotide attached to the magnetic bead comprises a poly(dA), poly (A), poly(dT) or poly(T) sequence.

In still further aspects, the invention provides methods for depositing molecules of interest onto a substrate, where those methods include the steps of: providing a solution of beads wherein each bead is linked to a polymerase composition comprising a scaffold attached to a complex containing a polymerase enzyme and a template nucleic acid; exposing the solution of beads to a substrate, the surface of the substrate comprising binding moieties for binding the functional moieties on the scaffold; using a contacting force to bring the beads into proximity or into physical contact with the substrate and optionally using a distributing force to move the beads across the surface of the substrate; and removing the beads from the substrate, thereby producing a substrate having the polymerase compositions bound to its surface through the binding molecules. In certain embodiments, the functional moieties are biotin moieties and the binding moieties are avidin moieties; in other embodiments, the functional moieties are avidin moieties and the binding moieties are biotin moieties. In further embodiments, the contacting force used to bring the beads to the substrate is a magnetic force. In yet further embodiments, the functional moieties on the scaffold deplete at least some of the binding moieties on the substrate, thereby preventing additional scaffolds (and their attached complexes) from entering the same substrate region. In still further embodiments, the substrate comprises an array of ZMWs.

In yet further aspects and in accordance with any of the above, distribution of the polymerase compositions of the invention, which generally include at least a scaffold attached to a polymerase enzyme, is aided through design of the solution used during the loading step. In some embodiments, a density gradient is used during loading in which a high density solution is added to the buffer in which the polymerase compositions are held. This high density solution assists in the movement of the polymerase compositions to the surface of the substrate, and then diffusion and/or use of a distributing force (such as the magnetic beads plus magnetic field described above) further distributes the compositions into the array regions.

In yet further aspects and in accordance with any of the above, distribution of the polymerase compositions of the invention is conducted in the presence of a divalent cation to improve loading of the polymerase enzyme compositions into the array regions as compared to loading in the absence of the divalent cation. In some embodiments, the divalent cation is a member selected from the group consisting of $Ca^{2+}$, $Sr^{2+}$, and $Ba^{2+}$. In further embodiments, the divalent cation is present in a concentration of about 0.2-about 5 mM. In yet further embodiments, the divalent cation is present in a concentration of about 0.1-10, 0.3-9.5, 0.4-9.0, 0.5-8.5, 0.6-8.0, 0.7-7.5, 0.8-7.0, 0.9-6.5, 1.0 6.5, 1.1-6.0, 1.2-5.5, 1.3-5.0, 1.4-4.5, 1.5-4.0, 1.6-3.5, 1.7-3.0, and 1.8-2.5 mM.

In further aspects and in accordance with any of the methods of distributing enzyme compositions at a super-Poisson level described herein, the methods may include a "clean up" step to boost a higher productive fraction of loaded reaction regions. Such clean up steps generally involve removing components of the compositions that are not bound together in a complex, thus ensuring that the compositions loaded into the reaction regions are active and contain all elements needed for subsequent reactions, such as sequencing reactions (e.g., the reaction regions are loaded with compositions comprising an enzyme attached to a scaffold and further attached to a nucleic acid template and in some embodiments a primer sequence attached to the template). In exemplary clean-up methods, enzymes that are not attached to scaffolds are removed from the population generally using beads comprising a random sequence. Further clean-up steps may include removal of excess scaffolds and/or scaffold arms that are not attached to or complexed with an enzyme. In further embodiments, methods known in the art are used to ensure that a large fraction of the polymerase molecule complexes loaded into the reaction regions are active. Such methods are described, for example, in U.S. Pat. No. 8,715,930, which is hereby incorporated by reference in its entirety for all purposes, and in particular for all written description, figures and figure legends related to loading molecules of interest onto a substrate.

In further aspects and in accordance with any of the above, the methods of the present invention are used to distribute single polymerase compositions into a plurality of ZMWs. For a description of ZMW arrays and their application to single molecule analyses, and particularly to nucleic acid sequencing, see, e.g., "Selective aluminum passivation for targeted immobilization of single DNA polymerase molecules in zero-mode waveguide nanostructures" (2008) Korlach et al. *Proceedings of the National Academy of Sciences U.S.A.* 105(4): 1176-1181; "Improved fabrication of zero-mode waveguides for single-molecule detection" (2008) Foquet et al. *Journal of Applied Physics* 103, 034301; "Zero-Mode Waveguides for Single-Molecule Analysis at High Concentrations" Levene et al. *Science* 299:682-686; published U.S. patent application No. 2003/0044781; Eid et al. (2008) "Real-Time DNA Sequencing from Single Polymerase Molecules" *Science* DOI: 10.1126/science.322.5905.1263b; and U.S. Pat. No. 6,917,726, each of which is incorporated herein by reference in its entirety for all purposes. Further descriptions of using methods and compositions of the invention in sequencing applications are provided in the following sections.

In further aspects and in accordance with any of the above, methods of distributing single polymerase compositions into a plurality of array regions include the steps of: (a) providing a surface comprising a plurality of array regions, wherein each array region comprises several binding elements; (b) exposing the surface to a solution comprising polymerase enzyme compositions, wherein each polymerase enzyme composition comprises a polymerase bound to a scaffold—in general, the scaffold includes a core comprising conjugation adaptors, and multiple arms comprising functional moieties attached to DNA molecules. The exposing is generally conducted under conditions such that the functional moieties of the DNA scaffold react with the binding elements of the array regions—in other words, the functional moieties deplete some to all of the binding elements in the array regions. In at least some of the array regions, the functional moieties react with available binding sites in a given array region and thus prevents other polymerase enzyme compositions from loading in that given array region, thereby distributing single polymerase molecules into a plurality of array regions. In some embodiments, the polymerase enzyme compositions are about 100 to about 200 nm in diameter at the widest point. In further embodiments, the scaffold is at least 150 nm in length at its widest point. In yet further embodiments, the scaffold is large enough to cover at least 90% of the array region. In some embodiments, the functional moieties comprise biotin moieties and the binding elements comprise avidin moieties. In other embodiments, the functional moieties comprise avidin moieties and the binding elements comprise biotin moieties. In certain embodiments, the scaffold is a star-shaped scaffold. In further embodiments, the scaffold is not a dendrimer.

In some embodiments and in accordance with any of the above, the multiple arms of the scaffold each comprise around 20-30 functional moieties. In further embodiments, the multiple arms of the scaffold comprise about 10-100, 20-90, 30-80, 40-70, 50-60 functional moieties. In further embodiments, each scaffold comprises about 3-5, 5-20, 7-18, 9-16, 11-14 arms. In yet further embodiments, the scaffold comprises a member selected from about 2, 3, 4, 5, 6, 7, 8, 9 and 10 arms.

In further embodiments and in accordance with any of the above, prior to the step of exposing the surface to a solution containing the polymerase enzyme compositions, the surface may in some embodiments be treated to add or modify the surface. In one non-limiting example in which the polymerase enzyme composition comprises a scaffold comprising biotin moieties as the functional moieties, the surface may be treated to add avidin moieties to the reaction regions as binding moieties. In other words, in some embodiments, the surface is first modified to add the appropriate binding moieties capable of reacting with the functional moieties on the scaffold of the polymerase enzyme composition.

In further aspects and in accordance with any of the above, methods of the invention include methods of distributing single polymerase molecules into a plurality of array regions, where the single polymerase molecules are attached to both a template nucleic acid and a scaffold comprising multiple functional moieties. In further embodiments, such methods include a step of forming a plurality of complexes comprising a template nucleic acid molecule, a single polymerase molecule, and a scaffold comprising multiple functional moieties. In some exemplary embodiments, the template nucleic acid may comprise a double stranded nucleic acid segment having a first and second end; a first hairpin oligonucleotide connecting each strand of the single template nucleic acid at the first end, wherein the first hairpin oligonucleotide comprises a primer binding site; and a second hairpin oligonucleotide connecting each strand of the single template nucleic acid at the second end, wherein the second hairpin oligonucleotide comprises a capture adapter. By "capture adapter" as used herein is meant a nucleotide sequence that is complementary to a capture sequence. Such a capture sequence can be used to enrich a population of these template nucleic acid sequences during synthesis to isolate those containing the capture adapter and/or prior to or subsequent to forming of the complexes to enrich the population for complexes containing the proper template nucleic acid sequences.

The above distribution method may in further embodiments include the step of disposing the plurality of complexes to a surface of array regions comprising binding elements, where the disposing is conducted under conditions such that the functional moieties of the scaffold react with the binding elements of the array regions. This disposing results in at least some of the array regions having the multiple functional moieties react with available binding sites and thus preventing other complexes from loading into that given array region, thereby distributing single polymerase molecules into those array regions. In further embodiments, prior to disposing the complexes to the surface, the plurality of complexes is first enriched for complexes containing active polymerases. In still further embodiments, the complexes further comprise magnetic beads, and the disposing step further comprises applying a magnetic field to direct the complexes to the array regions.

In some aspects, methods of super-Poisson loading in accordance with the present invention are particle-based methods utilizing a particle that has two regions: a more hydrophobic region and a less hydrophobic region. These regions are oriented such that when the particle comes into contact with a reaction region, the mutual attraction between the hydrophobic region of the particle and a hydrophobic region in the reaction region minimizes the free energy rotation of the particle, thus maximizing the overlap of contact between the particle and the reaction region. FIG. 19 provides a schematic illustration of an exemplary embodiment of this aspect of the invention. As will be appreciated, the particles do not need to be spherical—they can be cylindrical or an approximation of any rotatable shape that allows the polymer coating to establish hydrophobic interactions.

In further embodiments, these particle-based methods include the steps of: (a) providing a surface comprising a plurality of array regions, each array region comprising a hydrophobic area; (b) exposing the surface to a composition comprising polymerase enzyme complexes such that a portion of the plurality of array regions are occupied by a single polymerase enzyme complex, wherein each polymerase enzyme complex comprises: (i) a particle comprising a first region and a second region, wherein the second region is relatively more hydrophobic than the first region, and (ii) a polymerase enzyme attached to the second region of the particle, and wherein the polymerase enzyme complexes occupy the array regions such that the second region of the particle preferentially associates with the hydrophobic area of the array region. In further embodiments, the particle is oriented to maximize the overlap of contact between the second region of the particle and the hydrophobic area of the array region. In still further embodiments, the particle is spherical or cylindrical. In yet further embodiments, the second region of the particle has a pattern that produces a global energy minimum when associated with the hydrophobic area of the array region.

In yet further embodiments, methods of distributing enzyme compositions into reaction regions at super-Poisson levels involve the use of beads. Such methods can be used with or without the scaffolds described in further detail herein. In exemplary embodiments, small beads of a size that only one bead can fit in a reaction region are used—this "tethered loading" approach involves attaching an enzyme (including without limitation a polymerase, helicase or exonuclease) and a template nucleic acid to a single bead. The bead/complex is loaded onto a surface comprising array regions. Due to the ballast of the bead, only one bead/complex can be loaded into the reaction region. In further embodiments, the reaction regions are of a nanometer scale of around 50-200, 60-190, 70-180, 80-170, 90-160, 100-150, 110-140 nm. In further embodiments, the reaction regions are of about 100, 110, 120, 130, 140, 150, 160, 170, 180, 190, 200 nm in diameter. In still further embodiments, the reaction regions are ZMWs of about 150 nm in diameter. In yet further embodiments, the beads have a diameter of at least about 50%, 55%, 60%, 65%, 70%, 75%, 80%, 85%, 90%, 95% of the diameter of the reaction regions into which they are being distributed. In yet further embodiments, the beads have a diameter of about 50-190, 60-180, 70-170, 80-160, 90-150, 80-140, 90-130, 100-120 nm. In still further embodiments, the bead is about 55, 65, 75, 85, 95, 105, 115, 125, 135, 145, 155 nm in diameter. The beads can be attached to the complex in any method known in the art, including without limitation through complementary oligonucleotides or though nickel-NTA functionalized beads binding to a his-tag on the complex.

In further exemplary embodiments of the tethered-loading method, the bead/complexes may be directly loaded into the reaction regions. In further embodiments, the bead/complexes may in turn be tethered to larger beads—these larger beads are then loaded into the reaction regions. As will be appreciated, these larger beads may contain a single smaller bead/enzyme complex or may be attached to multiple bead/complexes. In yet further embodiments, the beads (either the single small beads or the larger beads attached to one or more small bead/enzyme complexes) may fit wholly within a reaction region or plug the opening of a reaction region, thus preventing other bead/complexes from loading into the same reaction region.

In further exemplary embodiments of the tethered loading method, the beads may be magnetic or non-magnetic. Magnetic beads tethered to the complex can be loaded into the reaction regions with the aid of a magnet. Non-magnetic beads can be loaded through gravity and diffusion or magnetically if tethered to a second (generally larger) magnetic bead.

In further embodiments and in accordance with any of the above description regarding tethered-loading methods, after loading of the bead/complexes into the reaction regions, the beads can be removed from the complexes. In embodiments utilizing magnetic beads, the beads can be removed through the aid of a magnetic. In embodiments in which the complex is attached to the bead through a Ni-histadine connection, exposing the complexes to histadine would release the beads. In embodiments in which the connection between the bead and the complex is through hybridization of complementary oligonucleotide segments, methods for "unzipping" the strands, including the use of denaturing agents and/or temperature, will also serve to release the beads, which can then be washed out of the system, leaving behind super-Poisson loaded reaction regions each containing a single enzyme complex.

In further aspects and in accordance with any of the super-Poisson loading methods described above, the distributing of the single polymerase molecules results in more than 37%, 45%, 50%, 55%, 60%, 65%, 70%, 75%, 80%, 85%, 90%, 91%, 92%, 93%, 94%, 95%, 96%, 97%, 98%, 99% of the array regions containing a single polymerase molecule. In yet further aspects, the distributing of the single polymerase molecules results in about 40-70%, 50-60%, 20-95%, 30-90%, 40-85%, 50-80%, 60-75% of the array regions containing a single polymerase molecule.

IV. Applications for Methods and Compositions of the Invention: Sequencing

The methods, devices, and compositions of the invention are particularly useful for single molecule sequencing methods, and specifically single molecule sequencing by incorporation in real time, because the present invention provides a way to establish a high density array of reaction regions occupied by a single polymerase composition. In general, the high density single molecule loading achieved by methods and compositions of the present invention is larger than what would be expected by a Poisson distribution based on a simple disposition of a dilute solution of polymerase compositions. Thus, sequencing methods relying on single molecule analysis can be conducted more efficiently and with greater speed, because there will be fewer "unusable" regions on a substrate surface for the sequencing reaction (i.e., regions that have no or multiple polymerase compositions loaded, which provide either no information (for the empty regions) or sequencing information that must be deconvoluted to account for the multiply loaded molecules).

In some aspects, the present invention includes methods of analyzing the sequence of template nucleic acids associated with the polymerase compositions and scaffolds discussed herein. In such aspects, the sequence analysis employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in embodiments utilizing sequence by synthesis processes, individual nucleotides or nucleotide analogs are identified iteratively as they are added to the growing primer extension product.

For sequencing processes that rely upon monitoring of the incorporation of nucleotides into growing nascent strands being synthesized by the complex, the progress of the reaction through these steps can of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product. By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

In further aspects, the methods of the present invention include steps from any single molecule sequencing methods known in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

In further embodiments, methods of single molecule sequencing known in the art include detecting individual nucleotides as they are incorporated into a primed template, i.e., sequencing by synthesis. Such methods often utilize exonucleases to sequentially release individual fluorescently labeled bases as a second step after DNA polymerase has formed a complete complementary strand. See Goodwin et al., "Application of Single Molecule Detection to DNA Sequencing," Nucleos. Nucleot. 16: 543-550 (1997).

In general, for sequencing methods utilizing compositions of the present invention, individual polymerase compositions are provided within separate discrete regions of a support. For example, in some cases, individual complexes may be provided within individual confinement structures, including nanoscale structures. In further examples, zero-mode waveguide cores or any of the reaction chambers discussed above in the stepwise sequencing section serve as the reaction regions for sequencing methods utilizing compositions of the present invention. Examples of waveguides and processes for immobilizing individual complexes therein are described in, e.g., Published International Patent Application No. WO 2007/123763, the full disclosure of which is incorporated herein by reference in its entirety for all purposes and in particular for all teachings related to providing individual complexes into individual confinement structures.

The sequencing processes, e.g., using the substrates described above and the compositions of the invention, are generally exploited in the context of a fluorescence microscope system that is capable of illuminating the various complexes on the substrate, and obtaining detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purpose.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse that carries a distinguishable spectral profile or color.

In further embodiments, compositions of the present invention are utilized in sequencing methods utilizing nanopores. In exemplary embodiments, enzymes are attached to the scaffold and then loaded into a nanopore—the nanopore comprises binding moieties complementary to reaction moieties on the scaffold. In this way, a single enzyme is loaded into each nanopore. In certain embodiments, the scaffolds and their attached enzymes are attached proximal to the nanopore. As will be appreciated, helicases and exonucleases as well as polymerases can be used in nanopore sequencing. Methods of nanopore sequencing are known in the art and disclosed for example in US Published App. Nos. 2013/0327644 and 2014/0051068, which are hereby incorporated by reference for all purposes and in particular for all teachings, written description, figures and figure legends related to nanopore sequencing.

The present invention can further include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C #, NET, Visual Basic, Python, JAVA, CGI, and the like.

In some cases, the compositions, methods, and systems of the invention can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof which are incorporated herein by reference in their entirety for all purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents that provide the catalytic and non-catalytic metal co-factors employed in the processes described herein. The kits will also optionally include other components for carrying out sequencing applications in accordance with those methods described herein. In particular, such kits may include ZMW array substrates for use in observing individual reaction complexes as described herein.

In addition to the various components set forth above, the kits will typically include instructions for combining the various components in the amounts and/or ratios set forth herein, to carry out the desired processes, as also described or referenced herein, e.g., for performing sequence by incorporation reactions.

In one aspect, the present invention provides methods and compositions for sequencing in which the sequence of a plurality of template nucleic acids is identified. "Primed nucleic acids" as discussed herein refer to nucleic acids that are in a condition to be replicated and/or extended in a template-directed manner, including without limitation nucleic acids hybridized to a primer that can be extended through the action of a polymerase as well as double stranded nucleic acids comprising a gap or a nick from which sequence-dependent replication can occur.

Different types of nucleotide analogs of use in the present invention may in some embodiments each have a different number of phosphate groups in the polyphosphate chain, such that each type may be identified from each other type upon incorporation. For example, the different types of nucleotide analogs may each correspond to a nucleobase independently selected from A, G, C, or T (or to one or more modified nucleobases), and each type may be distinguished from the other types based on characteristics such as the signal generated when the nucleotide analog is incorporated during a polymerase reaction. For example, each type of nucleotide analog can in some embodiments have a different number of phosphate groups in the polyphosphate chain, such that, upon incorporation of a particular nucleotide analog type during a polymerization reaction, the signal associated with the resultant cleavage of the phosphate bonds of the polyphosphate chain will identify the incorporated nucleotide analog as having a nucleobase A, C, G, or T. In further embodiments, sequencing reactions discussed herein may utilize 1, 2, 3, 4, 5, 6, 7, 8, 9, 10, 11, 12 or more different types of nucleotide analogs, and in further exemplary embodiments each of the different types of nucleotide analogs has a different number of phosphate groups in their polyphosphate chains.

Although in general the sequencing methods of the invention utilize one type of nucleoside polyphosphate for each round of incorporation and detection, it will be appreciated that such sequencing methods may also be conducted with multiple (1, 2, 3, 4, 5, 6, 7, 8, 9, 10, 11, 12 or more different types of nucleotide analogs) during each round of incorporation and detection. In further exemplary embodiments, each of the different types nucleotide analogs of use in the sequencing methods discussed herein have a number of phosphate groups independently selected from 3, 4, 5, 6, 7, 8, 9, 10, 11, 12, 13, 14, 15, 16, 17, 18, 19, 20, 21, 22, 23, 24, 25, 26, 27, 28, 29, or 30 phosphate groups.

In still further aspects, the exposing and detecting steps are repeated with a second, third and fourth type of nucleoside polyphosphates enough times to identify the sequence of the plurality of template nucleic acids

V. Substrates and Surfaces

Substrates of use in particular sequencing methods of the invention are known in the art and discussed herein, and as will be appreciated, any of the substrates discussed herein can be used in any combination for any embodiment of the sequencing reaction. In exemplary embodiments, methods of sequencing of the invention utilize substrates that include reaction regions comprising one or more reaction chambers arranged in the form of an array on an inert substrate material, also referred to herein as a "solid support", that allows for combination of the reactants in a sequencing reaction in a defined space and for detection of the sequencing reaction event. A reaction chamber can be a localized area on the substrate material that facilitates interaction of reactants, e.g., in a nucleic acid sequencing reaction—such an area is also referred to herein as an "array region". As discussed more fully below, the sequencing reactions contemplated by the invention can in some embodiments occur on numerous individual nucleic acid samples in tandem, in particular simultaneously sequencing numerous nucleic acid samples derived from genomic and chromosomal DNA. The apparatus of the invention can therefore include an array having a sufficient number of array regions/reaction chambers to carry out such numerous individual sequencing reactions. In one embodiment, the array comprises at least 1,000 reaction chambers. In another embodiment, the array comprises greater than 400,000 reaction chambers, preferably between 400,000 and 20,000,000 reaction chambers. In a more preferred embodiment, the array comprises between 1,000,000 and 16,000,000 reaction chambers.

The reaction chambers on the array may take the form of a cavity or well in the substrate material, having a width and depth, into which reactants can be deposited. One or more of the reactants typically are bound to the substrate material in the reaction chamber and the remainder of the reactants are in a medium which facilitates the reaction and which flows through the reaction chamber. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have a planar bottom or a concave bottom. The reaction chambers can be spaced between 5 µm and 200 µm apart. Spacing is determined by measuring the center-to-center distance between two adjacent reaction chambers. Typically, the reaction chambers can be spaced between 10 µm and 150 µm apart, preferably between 50 µm and 100 µm apart. In one embodiment, the reaction chambers have a width in one dimension of between 0.3 µm and 100 µm. The reaction chambers can have a width in one dimension of between 0.3 µm and 20 µm, preferably between 0.3 µm and 10 µm, and most preferably about 6 µm. In another embodiment, the reaction chambers have a width of between 20 µm and 70 µm. Ultimately the width of the chamber may be dependent on whether the nucleic acid samples require amplification. If no amplification is necessary, then smaller, e.g., 0.3 µm is preferred. If amplification is necessary, then larger, e.g., 6 µm is preferred. The depth of the reaction chambers are preferably between 10 µm and 100 µm. Alternatively, the reaction chambers may have a depth that is between 0.25 and 5 times the width in one dimension of the reaction chamber or, in another embodiment, between 0.3 and 1 times the width in one dimension of the reaction chamber.

Any material can be used as the solid support material, as long as the surface allows for stable attachment of the primers and detection of nucleic acid sequences. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

In certain aspects, reaction chambers, such as ZMWs, can be formed such that the chamber's fluidic volume is restricted while maintaining optical properties. In some cases, the process can involve first producing a structure having a lower transparent layer and an upper a cladding layer with holes or apertures extending through the cladding to the transparent layer; and subsequently depositing a layer of non-reflective material onto the walls. In some cases, the deposition of the non-reflective material can be carried out specifically, such that deposition only occurs on the cladding layer and not on the transparent substrate. In other cases, a conformal coating can be applied to the whole surface non-selectively. In some cases the non-selectively coated substrate can have the portions of the non-reflective material over the transparent substrate selectively removed. It can be advantageous to have some or all of the transparent substrate substantially free of non-reflective material, which can allow, for example, for the selective reaction of a functionalizing agent or coupling agent to the surface of the transparent substrate. Such a selectively functionalized transparent substrate can be used to selectively bind a molecule of interest, such as a polymerase enzyme selectively to the base of the reaction chamber structure. Such selective functionalization is described, for example in U.S. patent application Ser. No. 11/731,748, filed Mar. 29, 2007, which is hereby incorporated by reference for all purposes and in particular for all teachings related to selective functionalization.

In some embodiments, forming the non-reflective layer comprises forming an oxide layer by controlled oxidation of material that constitutes the cladding layer. The oxide layer can be formed, for example by thermal oxidation of the cladding layer in the presence of oxygen and heat, or by electrochemical oxidation whereby the cladding layer comprises an electrode. For example, where the cladding layer comprises aluminum, a layer of alumina can be formed on the surface of the aluminum by subjecting it to oxidizing conditions, either thermally or electrochemistry. In some cases, an oxygen plasma is used to produce the oxide layer. Forming an oxide layer on the cladding has the benefit that the non-reflective layer is formed selectively on the cladding, and is not formed on the transparent substrate.

Figure 22:
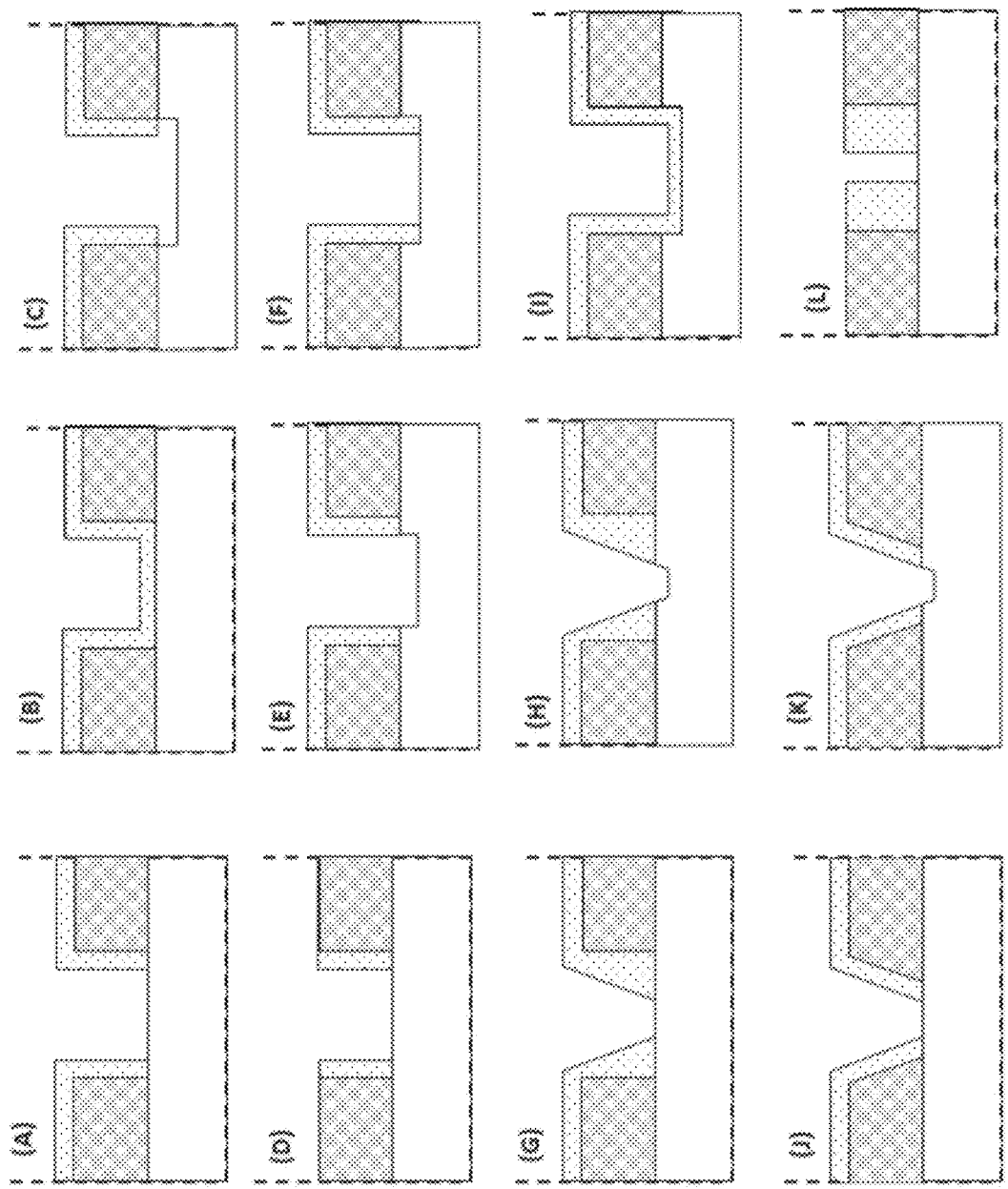
FIG. 22 shows cross-sections of exemplary ZMWs having non-reflective layers on their walls.

FIG. 22 shows cross-sections of some specific embodiments of ZMW structures having non-reflective layers on their walls. The ZMW shown in FIG. 22(A) has a layer of non-reflective material on the walls of the ZMW aperture and also on the top of the cladding layer. In some cases, the cross sections represent an aperture with a circular profile. The cross-sections can also represent profiles with other shapes including a slit, ellipse, rectangle, star, or any other suitable shape. This type of structure can result, for example, where the non-reflective layer comprises an oxide that is specifically grown onto a metal cladding layer, e.g. by thermal or electrochemical oxidation. The structure can also be produced by selective deposition onto the cladding layer or by first conformally coating the non-reflective material and second, removing the portion of the non-reflective material on the transparent substrate. In the ZMW shown in FIG. 22(B), the non-reflective layer covers the walls of the ZMW, the top of the cladding, and the top of the transparent substrate within the ZMW. This type of structure can be created, for example, by conformally coating a ZMW structure with a non-reflective material. In some cases, as shown in FIG. 22(C), the ZMW aperture will extend into the transparent substrate, and the non-reflective layer will be specifically on the opaque cladding layer, in some cases extending over the a portion of the aperture that extends into the transparent substrate. FIG. 22(D) shows a ZMW in which the non-reflective layer is only on the inside walls of the ZMW, and not on the top of the surface of the cladding. In FIG. 22(E) the portion of the aperture that can hold the solution extends into the transparent substrate and the non-reflective layer does not extend over the portion that extends into the transparent substrate.

FIG. 22(F) shows a ZMW in which the ZMW aperture extends into the transparent substrate and the non-reflective layer extends into the portion of the aperture that extends into the transparent substrate. In FIG. 22(G) the ZMW aperture has straight side walls (which for a ZMW with a spherical cross section would constitute a cylinder), and the non-reflective layer is applied so as to have angled sidewalls (which, for a solution volume with a spherical cross section would constitute a conical structure). FIG. 22(H) is similar to FIG. 22(G), but in which the solution containing portion extends into the transparent layer. In FIG. 22(I), the ZMW aperture extends into the transparent substrate, and the non-reflective layer coats the inside walls of the ZMW, the base of the ZMW, and the top surface of the cladding layer. In FIG. 22(J), the ZMW has angled sidewalls (which for a ZMW with a cylindrical cross section would constitute a conical structure), and the non-reflective layer also has angled sidewalls. FIG. 22(K) shows a ZMW similar to that in FIG. 22(J), but with the solution containing portion extending into the transparent layer. The ZMW of FIG. 22(L) is similar to that of FIG. 22(D), but having a non-reflective layer which is thicker. FIG. 22(L) illustrates that the methods of the invention can be used to lower the solution volume significantly and also to position a luminescent species at or near the center of the ZMW. It will be appreciated by those skilled in the art that the ZMW of the invention can be comprise a combination of two or more of the structures shown in FIG. 22.

The thickness of the non-reflective layer will generally be greater than about 5 nm. It is known, for example, that the native oxide layer on the surface of an aluminum metal can have a thickness of between about 3 to 4 microns. The thickness of the non-reflective layer will generally be greater than the thickness of this native oxide coating. It will be understood that the best thickness can depend on the diameter of the ZMW that is used and the use to which the ZMW is put. In some cases, for example, while a greater thickness of the non-reflective layer may be useful for improved optical properties, the greater thickness may result in a solution volume which is too small to accommodate the species to be analyzed, for example, the enzyme and/or its substrate. The structures and methods of the invention allow for adjusting the thickness of the non-reflective layer and the dimensions of the ZMW in order to improve the overall performance of the system which incorporates the ZMW, for example the analysis of biomolecules and nucleic acid sequencing.

In some cases, the non-reflective coating has a thickness of between about 5 nm and about 50 nm, between about 8 nm and 40 nm, and between about 10 nm and about 30 nm. In some cases, a ZMW having a cross-sectional dimension of about 50 nm to about 105 nm has a non-reflective coating of about 10 nm to about 30 nm of thickness. The thickness of the non-reflective layer is generally maintained such that a solution volume is maintained inside of the ZMW.

The non-reflective layer will generally result in a cross-sectional dimension within the non-reflective layer being less than the corresponding cross-sectional dimension of the ZMW. For the ZMW's of the invention, the solution volume within the non-reflective area of the ZMW will have a cross-sectional dimension that is about 10% to about 95%, from about 20% to about 80%, or between about 25% to about 50% of the corresponding cross-sectional dimension of the ZMW. Where the ZMW and the solution volume within the non-reflective layer in the ZMW each comprise cylindrical structures with circular cross sections, for example, the cross-sectional dimension would be the diameter of the circular cross-section. In some cases the cross-sectional dimensions will vary with height, in which case the average or median cross-sectional dimension can be used. In other cases, the cross-sectional dimension at a given height, such as at the base of the ZMW can be used.

The non-reflective coating will take up a portion of the cross-sectional area which would be available to a solution if the non-reflective layer was not present, thus lowering the solution volume within the ZMW. In some cases, the ZMW of the invention will have a cross-sectional area inside the non-reflective layer (the solution volume) that comprises from about 10% to about 90%, from about 30% to about 80%, or between about 30% to about 50% of the corresponding cross-sectional area of the ZMW. The cross-sectional area of a ZMW may vary with height. In some cases, the average or median cross sectional area of the ZMW is used to determine the relative amount of the non-reflective layer. In some cases, the relative cross sectional areas at a given height, such as at the base of the ZMW can be used.

The cladding is typically made of materials that prevent any significant penetration of the electric and the magnetic fields of an electromagnetic radiation that is opaque and/or reflective materials. Suitable materials for fabricating the cladding include but are not limited to metals, metal oxides, alloys, conducting materials and semi-conducting materials, and any combination thereof. The cladding layer can comprise a metal such as aluminum, copper, gold, silver, chromium, titanium or mixtures thereof.

The transparent substrate can comprise inorganic materials, organic materials, or composite materials with both organic and inorganic materials. The transparent material is typically a rigid material which can keep the reactive regions in fixed positions during observation. Silica based materials, such fused silica are preferred materials, for example, where semiconductor or MEMS processing methods are used to produce the micromirror arrays. The transparent substrate may also comprise inorganic oxide materials and glasses. The transparent substrate material may be a heterogeneous material, such as a material having multiple layers. In some cases, for example, the transparent substrate may comprise a dielectric stack. Transparent polymeric materials can also be used. It is typically desired that the transparent material exhibit low levels of autofluorecence. Suitable transparent polymers comprise, for example, methacrylate polymers such as PMMA, polycarbonates, cyclic olefin polymers, sytrenic polymers, fluorine-containing polymers, polyesters, polyetherketones, polyethersulfones, polyimides or mixtures thereof.

The non-reflective layer on the walls of the ZMW is generally transparent to the light at the wavelength at which the ZMWs are used, so can also be referred to as non-opaque materials. While generally transparent, the non-reflective layers need not be completely transparent, and could be, for instance translucent. The non-reflective layer can be made of any suitable material that is generally transparent to the light used with the ZMW. The non-reflective layer material can be inorganic or organic. In some cases, the non-reflective layer comprises an oxide or a nitride. Suitable oxides include oxides of aluminum, titanium, zinc, chromium, nickel, molybdenum, silver, magnesium, cesium, hafnium, zirconium, and silicon. In some cases, oxides of aluminum are used. As described in more detail below, in some cases the non-reflective layer comprises an oxide of a metal which comprises the opaque cladding layer. Sol-gel materials can be used to form the non-reflective layer, often composed largely of silicon oxides with smaller amounts of other oxides. Polymeric materials can comprise the non-reflective layer. Such polymers can be either largely carbon based or silicon based. Suitable polymers include acrylates, methacrylates, polyimides, polyamides, polyketones, polysulfones, polyesters, cellulose based polymers, polycarbonates, cyclic olefin polymers, sytrenic polymers, fluorine-containing polymers, polyetherketones, polyethersulfones, polydimethylsiloxane (PDMS), poly(methyl methacrylate) (PMMA), and the like. Mixtures and copolymers of the above polymers can also be used.

Figure 23:
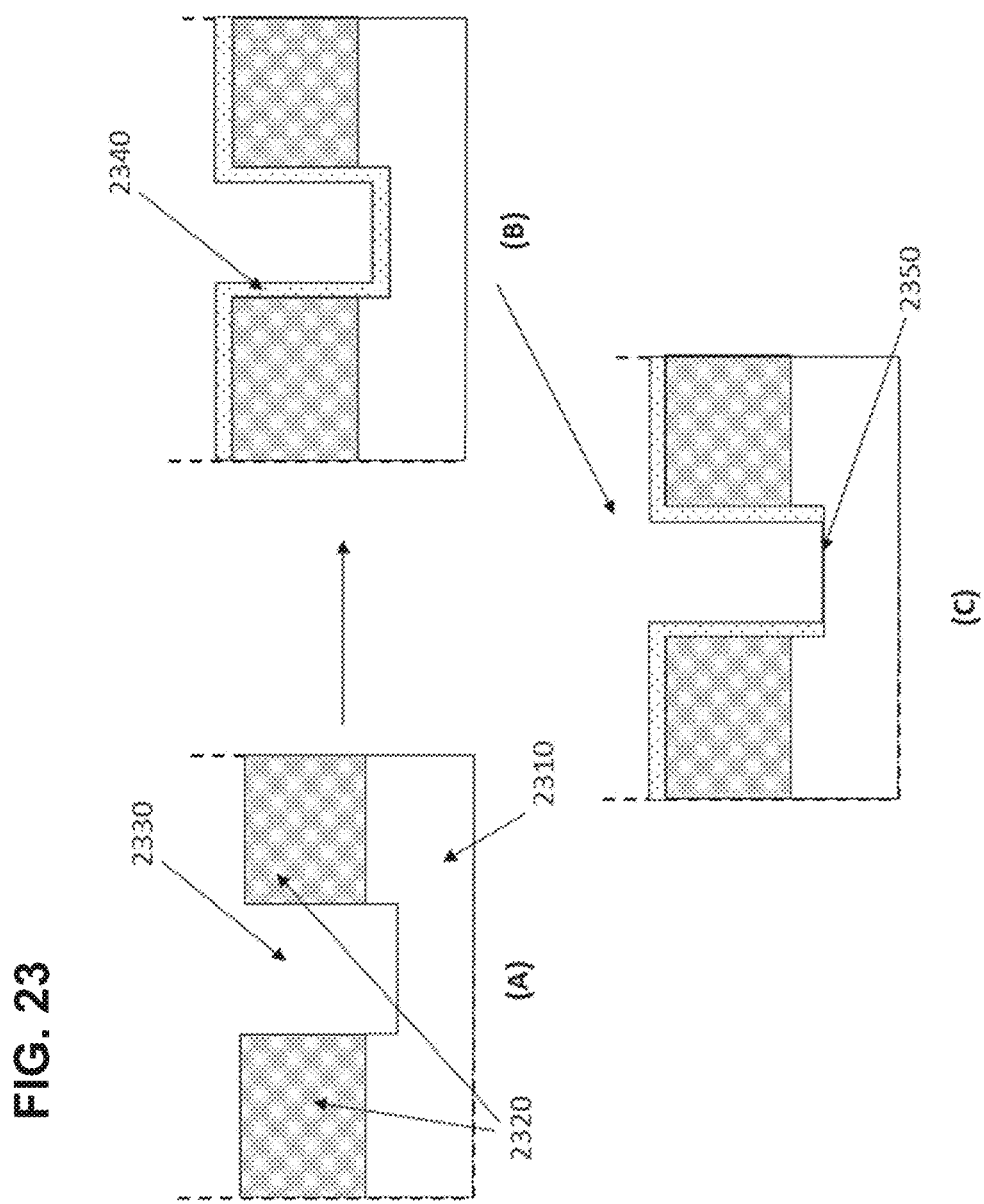
FIG. 23 illustrates a process for producing the non-reflective layer of the invention for a ZMW having an aperture that extends into the transparent substrate by depositing a conformal coating.

FIG. 23 illustrates an exemplary process for producing non-reflective layers on the ZMW walls where the ZMW aperture extends through the cladding layer and into the transparent substrate. The structure in FIG. 23(A) has a transparent substrate 2310 upon which a cladding layer 2320 is disposed. The cladding layer 2320 has apertures 2330 extending through the cladding layer and extending into the transparent substrate. The structure of FIG. 23(A) is coated with the non-reflective layer material in a conformal manner such that the ZMW walls, the bases of the ZMWs, and the top surface of the cladding layer is coated relatively uniformly. Since the aperture extends into the transparent substrate, the coating on the top of the transparent substrate does not necessarily raise the base up into the ZMW. In some cases, subsequent to conformal coating, the portion of the non-reflective layer over the transparent substrate at the ZMW base can be selectively removed, or etched back, exposing the transparent substrate at the ZMW base 2350, and allowing specific functionalization of the surface, for example, using silanes. The etch-back step can be performed, for example, by using photolithography to define the region for etch-back.

As discussed above, as the non-reflective layer increases, the region inside the ZMW (the solution volume) will generally become smaller. These dimensional changes can be taken into account using any of the methods described herein and known in the art to result in a ZMW having both the desired ZMW dimensions and the desired solution volume dimensions. In certain exemplary embodiments, the solution volumes range from $1\times10^{-21}$ liters to $1\times10^{-16}$ liters, $1\times10^{-19}$ liters to $1\times10^{-17}$ liters, or $1\times10^{-18}$ liters to $1\times10^{-17}$ liters. In further exemplary embodiments, the diameter of the ZMWs range from about 10-250, 20-240, 30-230, 40-220, 50-210, 60-200, 70-190, 80-180, 90-170, 100-160, 110-150, 120-140 nm. In still further exemplary embodiments, the diameter of the ZMW is about 10, 50, 100, 110, 120, 130, 140, 150, 160, 170, 180, 190, 200, 210, 220, 230, 240, 250, 260, 270, 280, 290, 300 nm. In yet further embodiments, the height of the ZMW ranges from about 10-500, 50-475, 100-450, 150-425, 200-400, 250-375, 300-350 nm.

Additional methods for forming layers on reaction chambers are described for example in US Patent Publication No. 20140175052, which is hereby incorporated by reference for all purposes and in particular for all teachings directed to forming reaction chambers and coating layers in such chambers.

EXAMPLES

Example 1: Assessments of Loading Distributions

Figure 4:
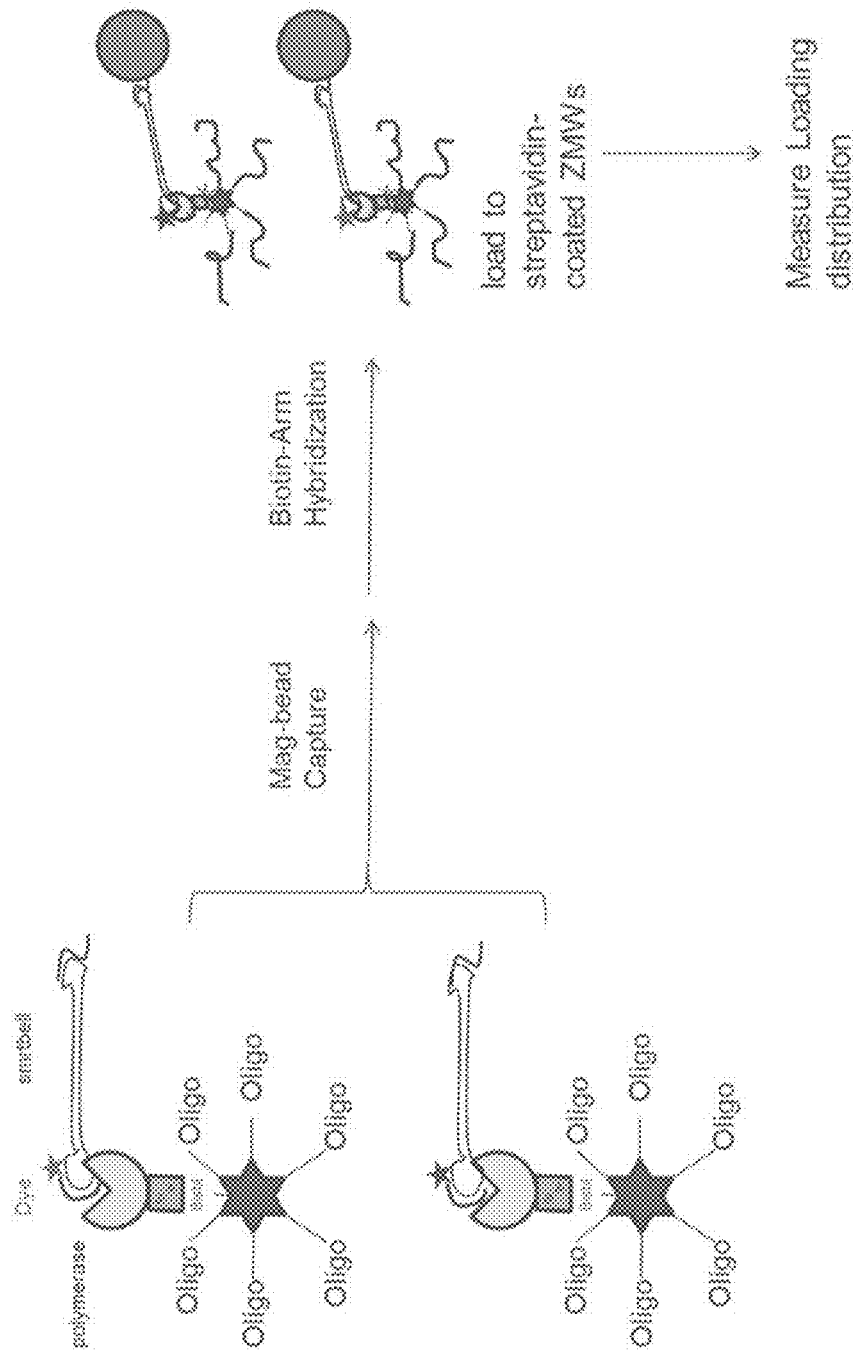
FIG. 4 is a schematic illustration of one embodiment of the invention in which scaffolds are attached to polymerase-template complexes.

One way to compute loading distribution is through a 2-color Loading Assay. As shown in FIG. 4, scaffolds were attached to polymerase-template complexes, which were pre-labeled with 1:1 mixture of green fluorescence dye or a red fluorescence dye. The label can be attached to either the primer, the DNA template, or the enzyme for these purposes. The complexes were loaded to Pacific Biosciences SmrtCell and the loading distribution was measured by counting the number of ZMWs with no fluorescence signal, green fluorescence signal, red fluorescence signal, and both colors. ZMW loading results were classified as empty, red color only, green color only, and 2-color, and the results were compared with Poisson statistics. The factions of each loading class was treated as approximation of probability, as determined by Poisson distribution.

To measure super-Poisson loading calculation:

Total % grn=% grn single color+% colo     i.

Total Red=% red single color+% colo     ii.

If loading follows Poisson distribution, then % 2-color=% Total grn*% Total red     iii.

Figure 5:
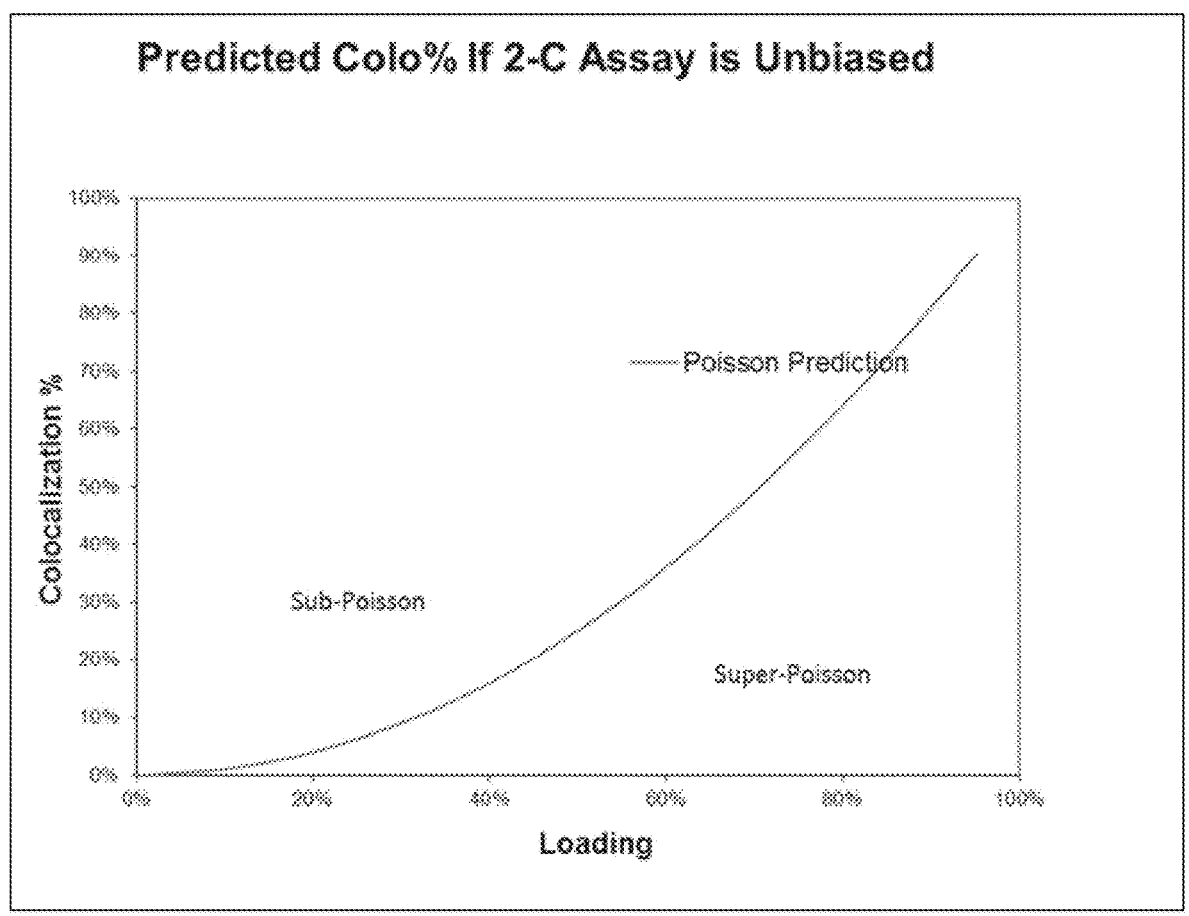
FIG. 5 provides simulated data for predicted values from a 2-color assay.

P(total colo)=P(Total grn)*P(Total Red) formula can be proved based on Poisson statistics, and was verified by control data. See FIG. 5.

The percentage difference of experiment % 2-color and Poisson-predicted % 2-color is defined as % SP (percent super-Poisson). This is a metric that tracks super-Poisson activity. % SP=100% is complete super-Poisson loading, while % SP=0% is Poisson loading:

% SP=−(% colo−% colo_Poisson)/% colo_Poisson     iv.

Figure 6:
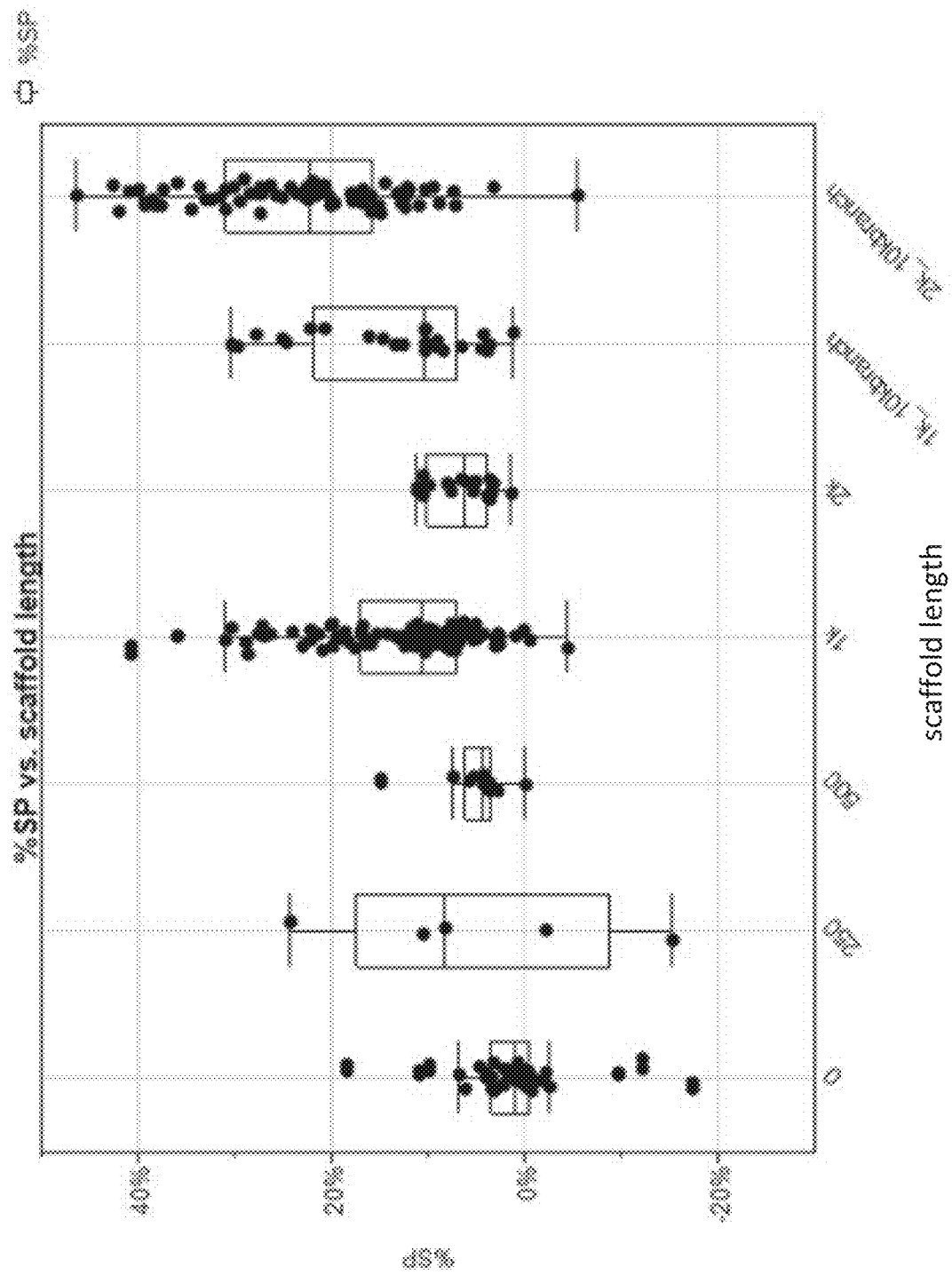
FIG. 6 shows data from a 2-color loading assay for linear scaffolds of varying length and branches.

FIG. 6 shows the % SP number from linear and branched DNA scaffold measured by the two color (2C) loading assay. 0 represents control loading without any scaffold, while 250, 500, 1 k, and 2 k represents linear DNA scaffold length, and 2 branched DNA scaffolds are 1k_10 kbranch and 2k_10 k branch. One can see that control data follows Poisson loading closely (% SP close to 0); short (250 AND 500) linear DNA scaffold gave small deviation from Poisson; while average % SP increase to 10% for 1 k scaffold and then over 20% for 2k_10 k branch scaffold. In one non-limiting mechanism, the scaffold is of a size large enough to cover multiple to all the biotins in the ZMW well to show effective loading. In addition, scaffolds with branches were more effective in biotin depletion. One non-limiting mechanism to explain the effect of the branched scaffolds is that the biotins are more accessible on such molecules.

Figure 7:
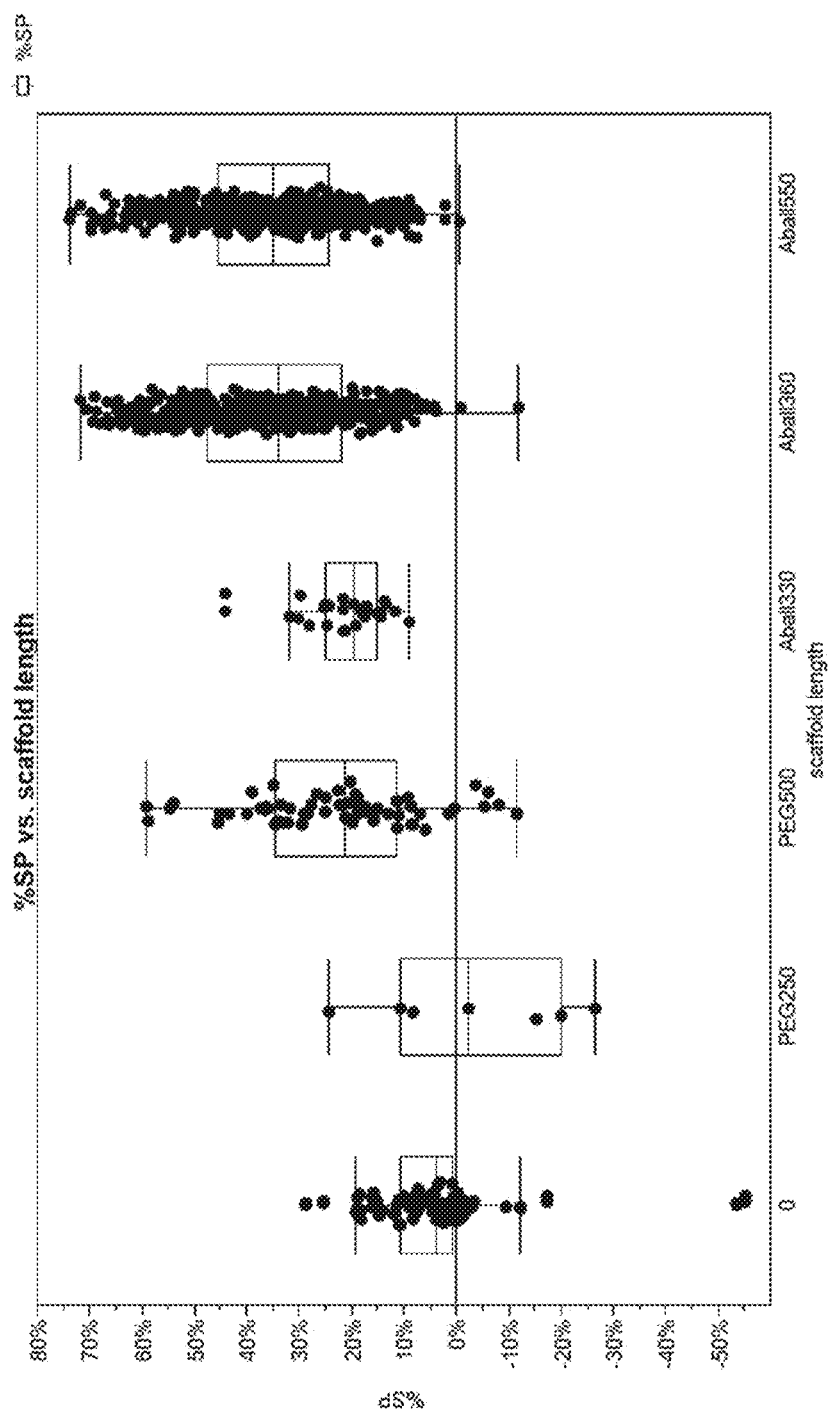
FIG. 7 shows data from a 2-color loading assay for star-shaped scaffolds.
Figure 8B:
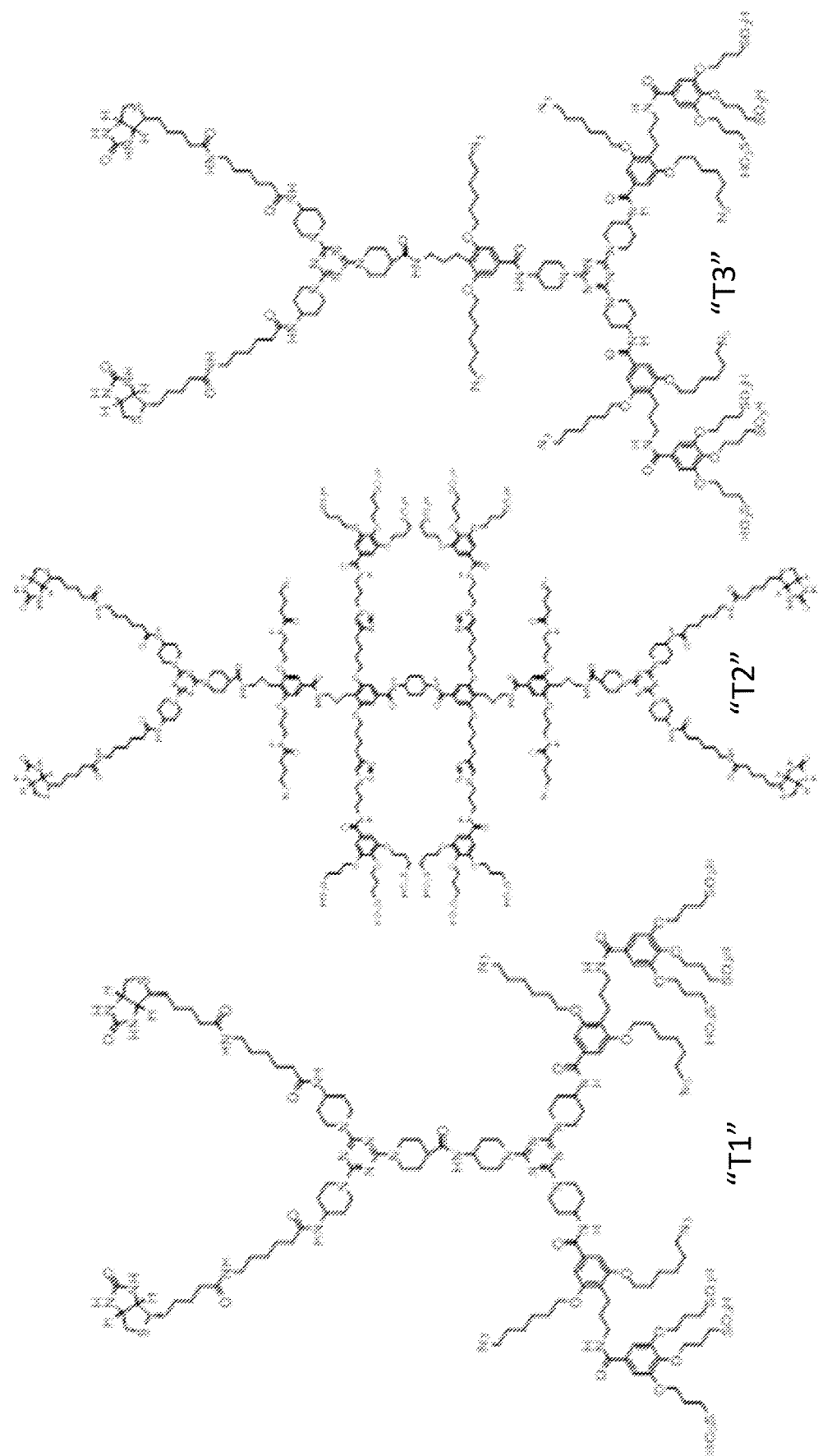

FIG. 7 show the % SP data from star-shaped scaffolds—as above, the measurements are by the 2C loading assay. 0 represents control loading without any scaffold, while PEG250, PEG500, Aba11330, Aba11360, and Aba11550 represent different star-shaped scaffolds with different arm lengths. "PEG" has a 4-arm PEG molecule as the core, while "Aba11" have 4-arm or 6-arm Aba11. The show that the Aba11 scaffolds show better results than PEG as the core molecule for the scaffold. In addition, both 360-mer DNA arm and 550-mer DNA arm yielded super-Poisson loading results. Structures of these star-shaped scaffolds are shown in FIG. 8A-C. Note that although the structures shown in FIG. 8C show T1 as the core, it will be appreciated that any of the T1, T2 and T3 cores pictured in FIG. 8B can be used in the structures in FIG. 8C.

Figure 9:
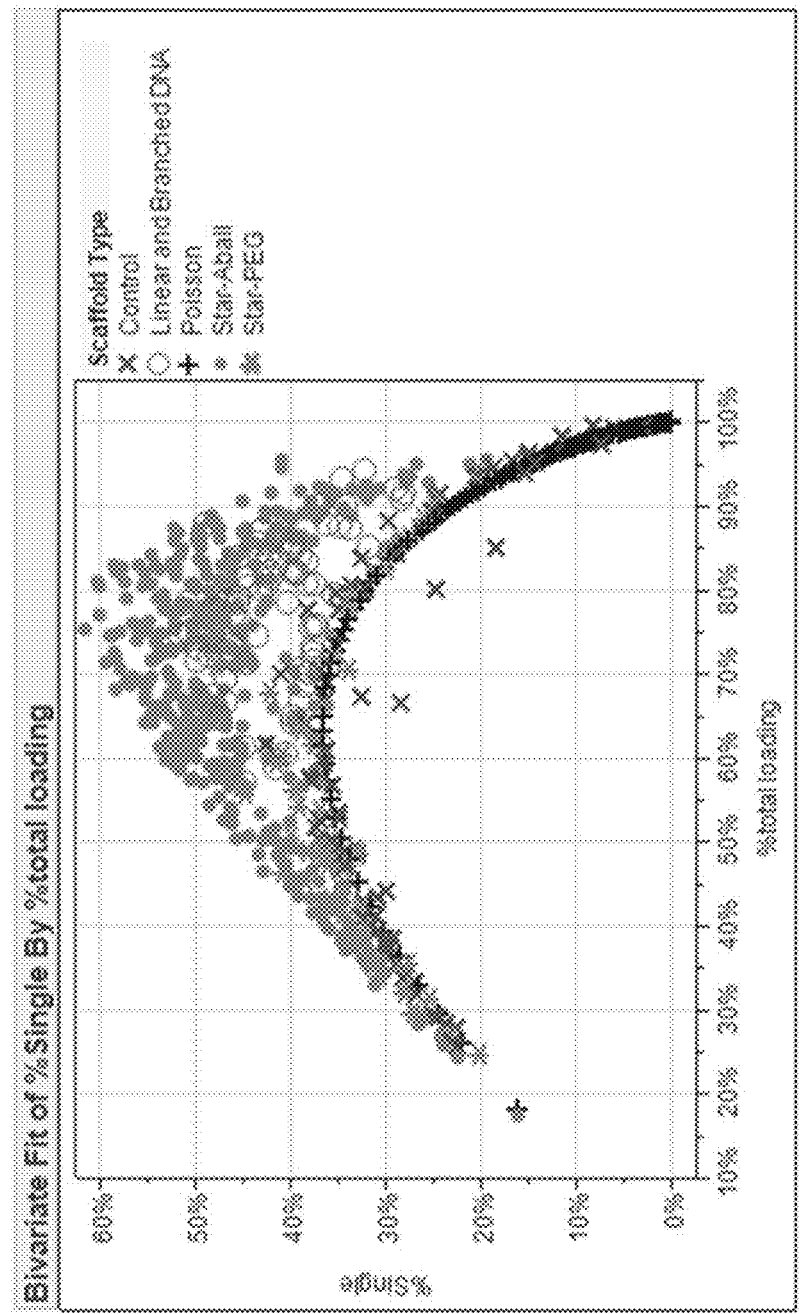
FIG. 9 shows data on single-loaded array regions for different scaffold types.

Alternatively, super-Poisson loading effect can be measured from sequencing data directly. The number of singly-loaded ZMWs was determined by counting the number of sequencing traces with one active polymerase. Such traces can be distinguished by pulse rate (close to the incorporation rate of one polymerase) and alignment accuracy. The multiple-loaded ZMWs, on the other hand, produce sequencing traces with many extra pulses and poor reference alignment; the empty ZMWs produce only few non-specific pulses. Chart VI plots the super-Poisson effect measured with sequencing experiment, in which the "+" marked data points are theoretical Poisson prediction of % single−% Loading numbers, "x" are control data without the use of scaffold, and the other data points are from the 3 types of DNA scaffolds. The "Star-Aba11" scaffolds gave the highest % single loading. (FIG. 9)

Figure 10:
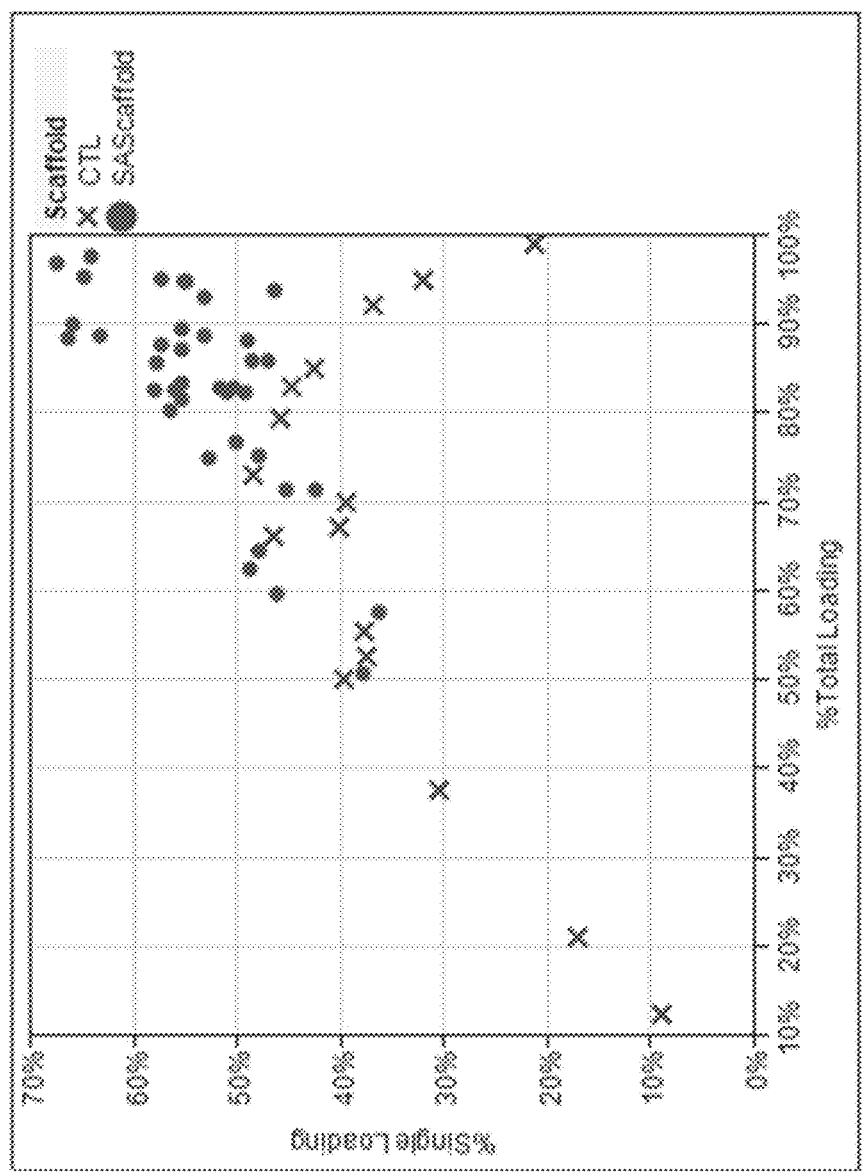
FIG. 10 shows loading distribution data from a scaffold containing avidin moieties as functional moieties (also referred to herein as "avidin scaffold").

FIG. 10 shows loading distribution data from avidin scaffold measured though sequencing. % single loading number from avidin scaffold surpassed control data when loading is above 70%. The stronger super-Poisson loading effect here seems to be, without being limited to any particular mechanism, the result of better depletion power, as each avidin scaffold can theoretically bind the 4 biotins on the surface.

Example 2: Use of Divalent Cations to Improve Loading of DNA Complex

Figure 24:
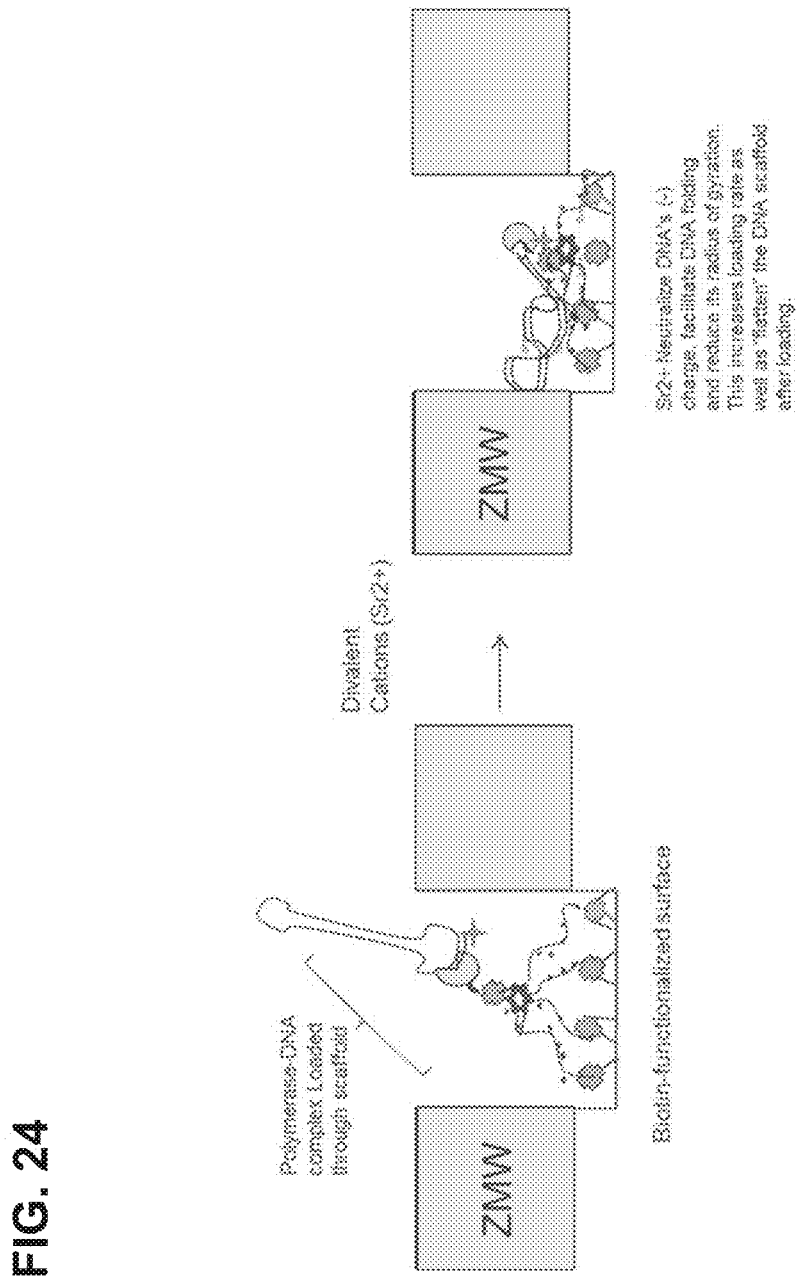
FIG. 24 illustrates an exemplary process of the invention.

When the polymerase-DNA template-biotin scaffold complex is loaded in a buffer without any divalent cations, the loading kinetics can be slow due to the slow diffusion of the large complex. In some embodiments, divalent cations are applied at concentration above 0.1 mM to facilitate DNA folding, which reduces the radius of gyration of the complex and increases its diffusion rate (Scheme VI (FIG. 24)). The cations used can be $Ca^{2+}$, $Sr^{2+}$, $Ba^{2+}$, $Co^{3+}$, etc for this purpose.

Figure 11:
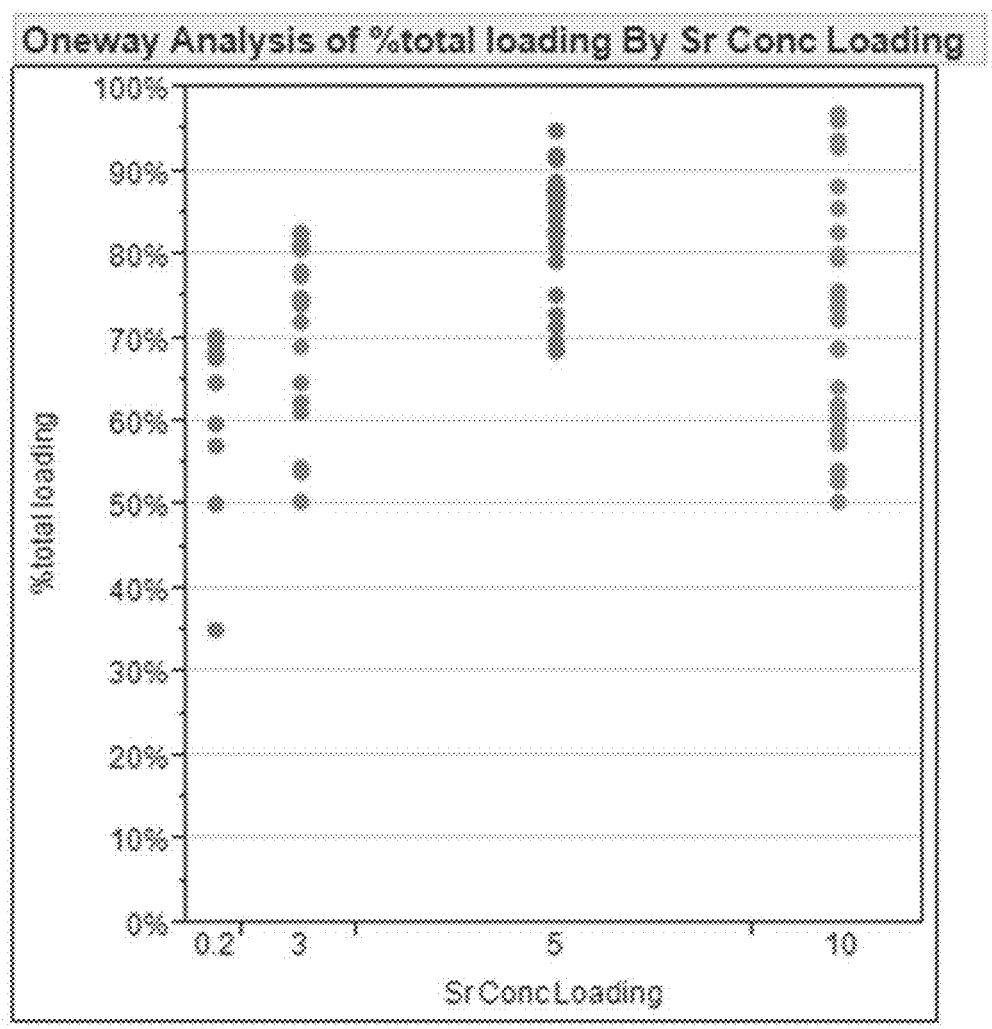
FIG. 11 shows data on single molecule loading at different strontium ($Sr^{2+}$) concentrations.

$Sr^{2+}$ concentration was titrated into the loading mixture and total loading of the polymerase-DNA template-biotin scaffold complex was observed. Total complex loading improvement was observed at $Sr^{2+}$ concentration of 0.2-5 mM (FIG. 11).

Example 3: Preparing the Biotin DNA Arm for Star-Shaped Scaffold

As discussed herein, compositions of the present invention include star-shaped scaffolds comprising a core and multiple arms, where the multiple arms comprise biotin moieties.

Figure 25:
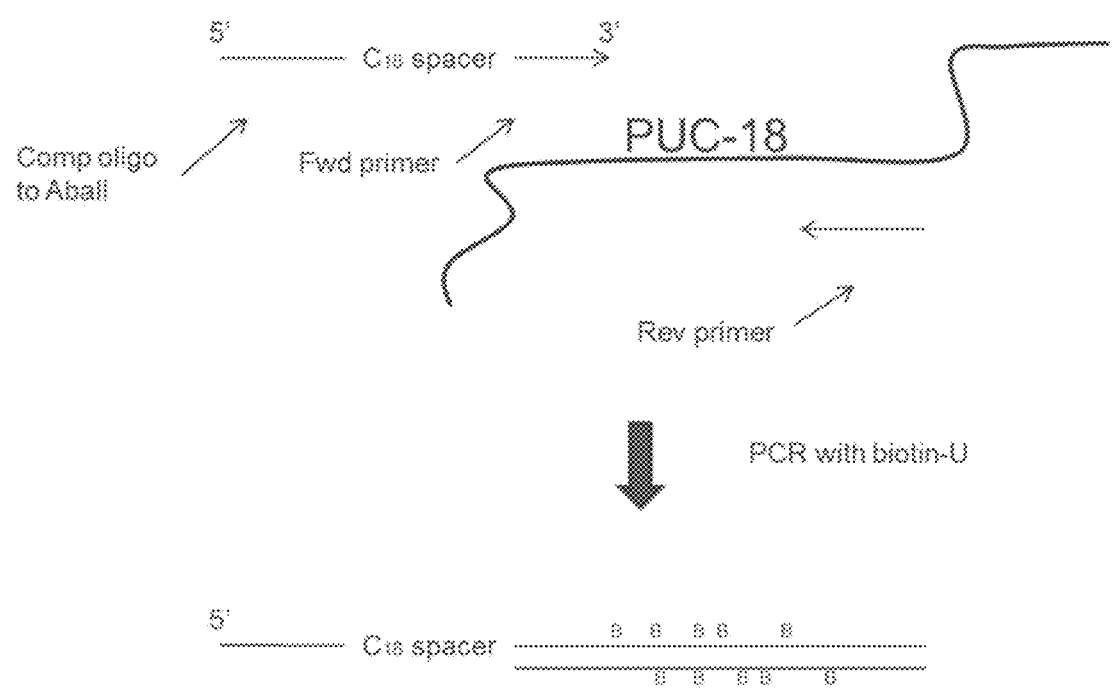
FIG. 25 shows an embodiment of an exemplary preparation scheme for a Biotin-DNA arm of a scaffold of the invention.

In one exemplary embodiment, the Biotin-DNA arm was prepared via PCR as illustrated in Scheme I (FIG. 25).

A PCR primer with a spacer was applied to produce a PCR amplicon with a ssDNA overhang, and biotin-labeled dUTP was introduced at 10-80% of standard dTTP concentration to incorporate biotin functional group to the resultant PCR product. The product was characterized by gel electrophoresis as well as DNAase digestion to ensure the biotin incorporation. For example, FIG. 12 shows gel electrophoresis data for biotin arms made with 0, 40%, and 60% biotin-UTP. Gel-shifts due to biotin incorporation are evident in this figure.

Alternatively, amino, thiol, azide, or alkyne functional groups can be introduced to DNA by a similar method as described above, and biotin moieties can then be added via NHS ester chemistry, maleimide chemistry, or click chemistry.

Example 4: Preparing the Avidin DNA Arm for Star-Shaped Scaffold

Star-shaped scaffolds comprising a core and multiple arms may also have arms comprising avidin moieties.

Figure 13:
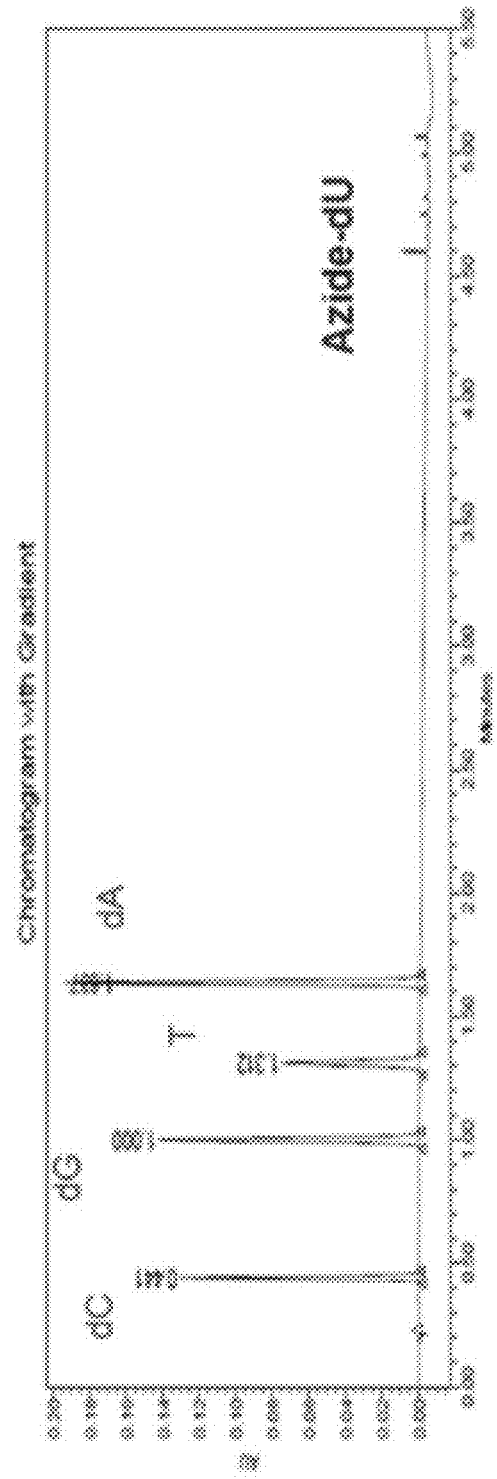
FIG. 13 shows the level of azide incorporation during an embodiment of a DNA arm synthesis method of the present invention.
Figure 26:
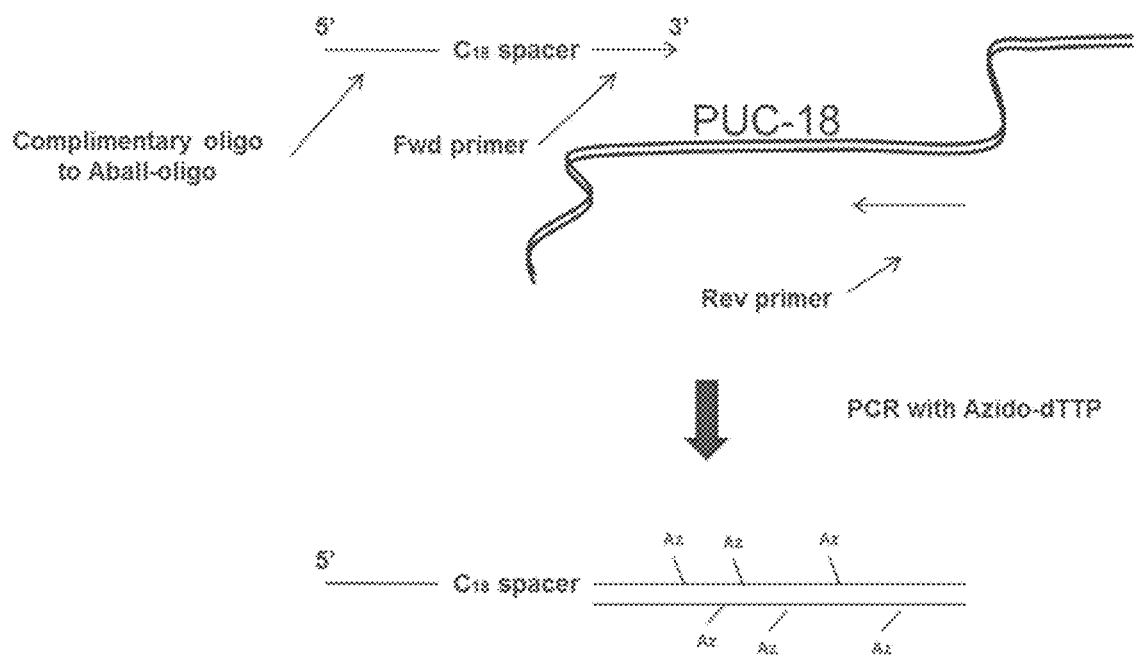
FIG. 26 shows an embodiment of an exemplary preparation scheme of a scaffold of the invention.
Figure 27:
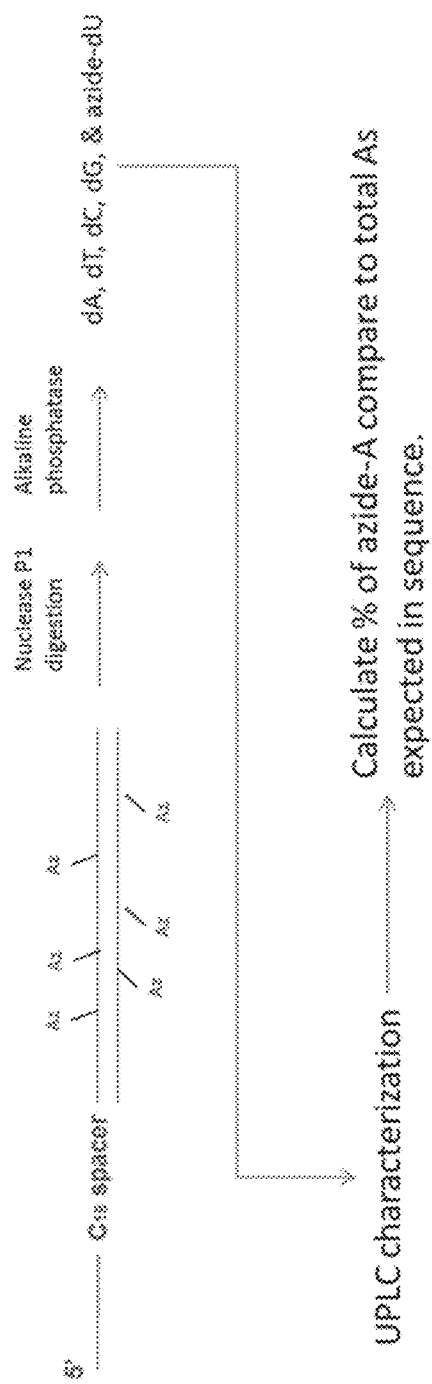
FIG. 27 shows an embodiment of an exemplary preparation scheme of a scaffold of the invention.

To construct SAv scaffold, a DNA arm was first prepared via PCR using a method similar to the biotin-DNA method described above. A PCR primer with a spacer was applied to produce the PCR amplicon with a ssDNA overhang, and azide-labeled dUTP was introduced at 10-40% of standard dTTP concentration to incorporate azide functional group to the resulted PCR product, as pictured in Scheme II (FIG. 26):

The product was characterized by gel electrophoresis as well as DNAase digestion (Scheme III (FIG. 27)) to ensure the azide incorporation:

UPLC (Ultra Performance Liquid Chromatography) analysis of the digested DNA confirms azide incorporation and provides the average number of azide groups per DNA molecule (FIG. 13).

The PCR conditions for making the azide-DNA with ssDNA overhang were as follows:

| PCR conditions: | |
| --- | --- |
| Step 1: | 94° C. for 2 minutes |
| Step 2: | Start of cycle |
| | 94° C. for 30 seconds |
| Annealing temperature | 55° C. for 30 seconds |
| | 72° C. for 1 minute |
| | 35 Cycles total |
| Step 3: | 72° C. for 5 minutes |
| Step 4: | 4° C. |

Example 5: DBCO Modified Avidin Arm Preparation

Figure 28:
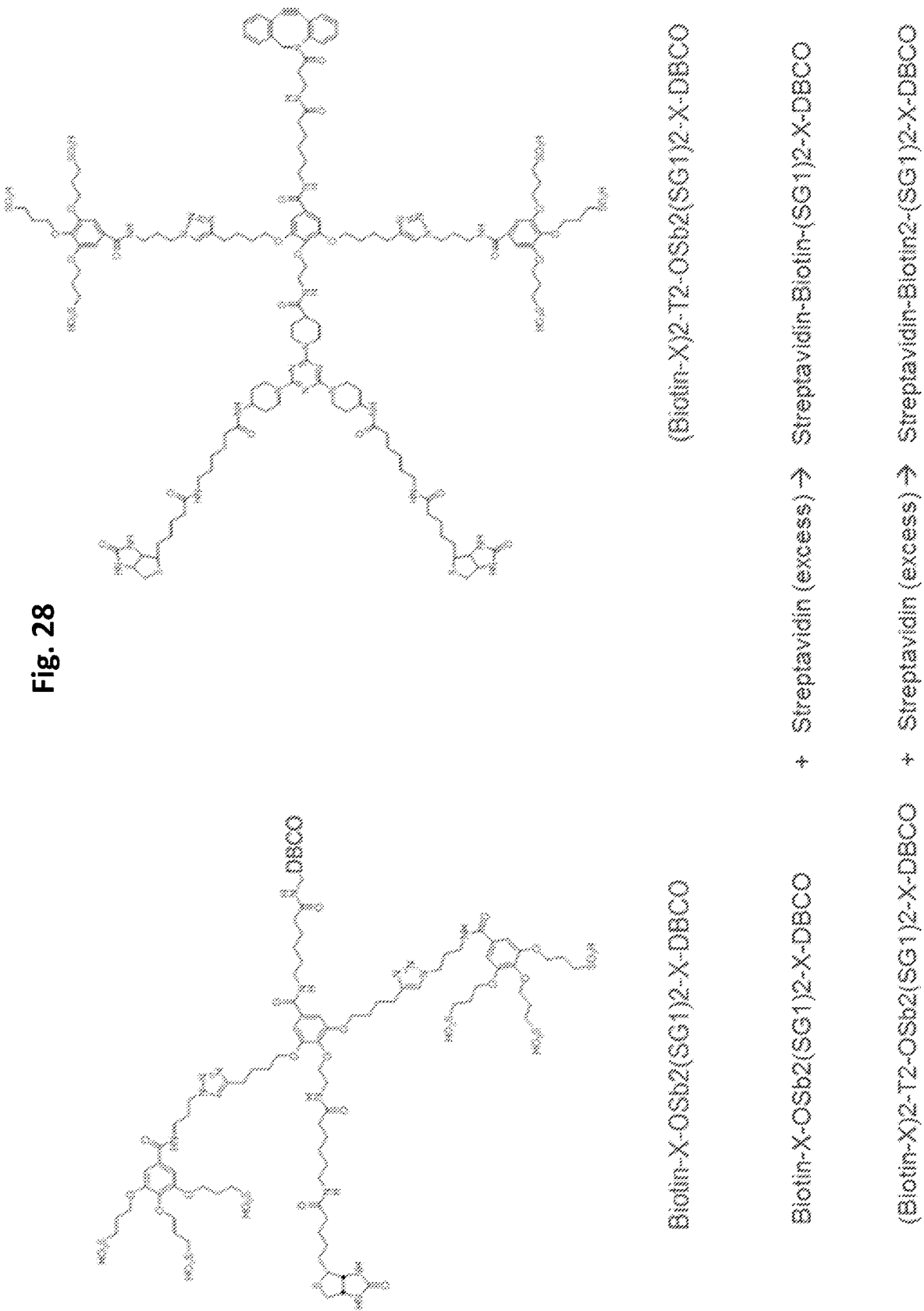
FIG. 28 shows an embodiment of an exemplary preparation scheme of a scaffold of the invention.

An alternative version of the avidin arm prepared was an arm modified with Dibenzocyclooctyl (DBCO). The beginning molecule for this modified avidin scaffold was made in accordance with Scheme IV (FIG. 28) in which a biotin conjugate with DBCO was synthesized first, and then was reacted with excess avidin to form a mixture of single DBCO-SA adduct and 2:1, 3:1, 4:1 adducts. Both Biotin-X-OSb2(SG1)2-X-DBCO and (Biotin-X)2-T2-OSb2(SG1)2-X-DBCO can be applied for this reaction. The mixture was then purified with ion exchange chromatography, and the single DBCO-SA conjugate isolated.

Figure 29A:
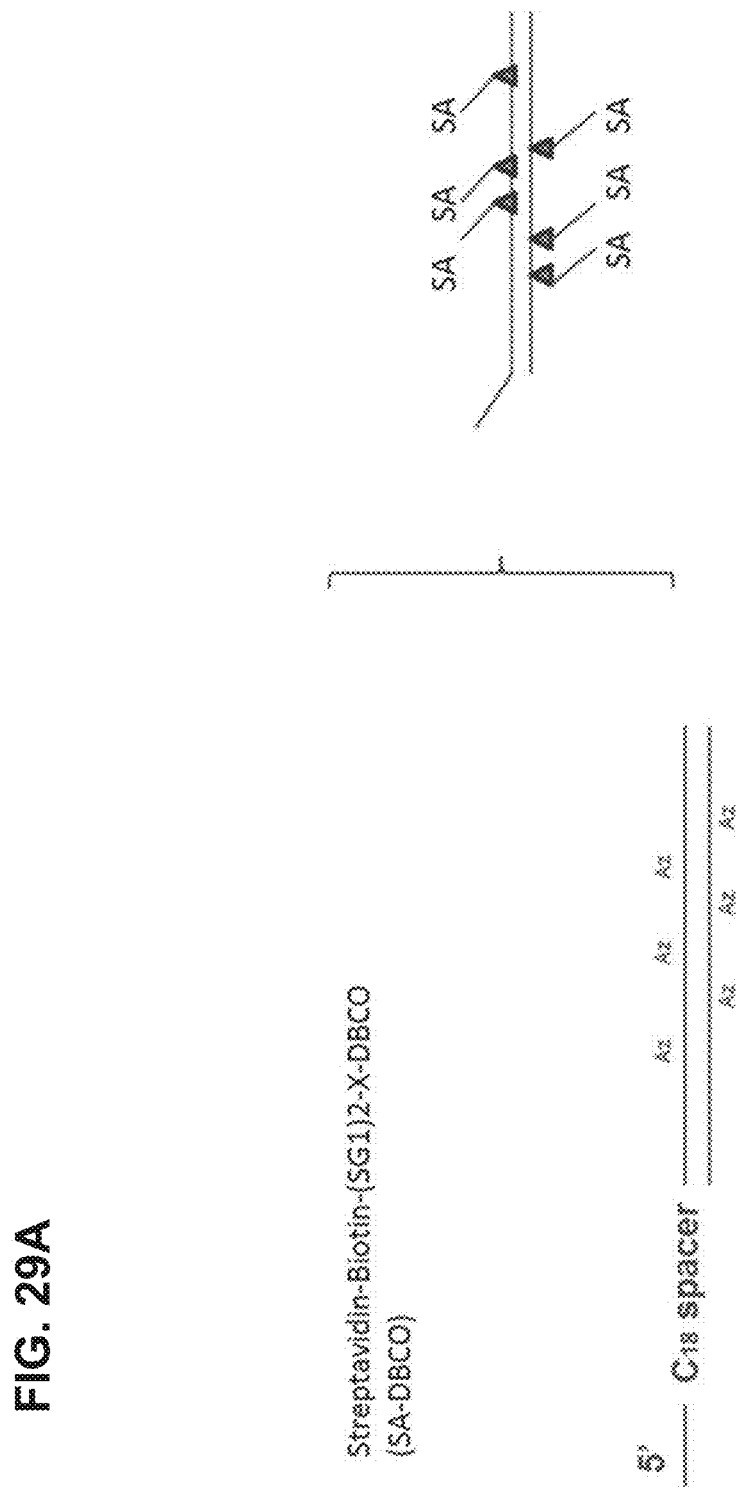
FIG. 29A-FIG. 29B shows an embodiment of an exemplary preparation scheme of a scaffold of the invention.
Figure 29B:
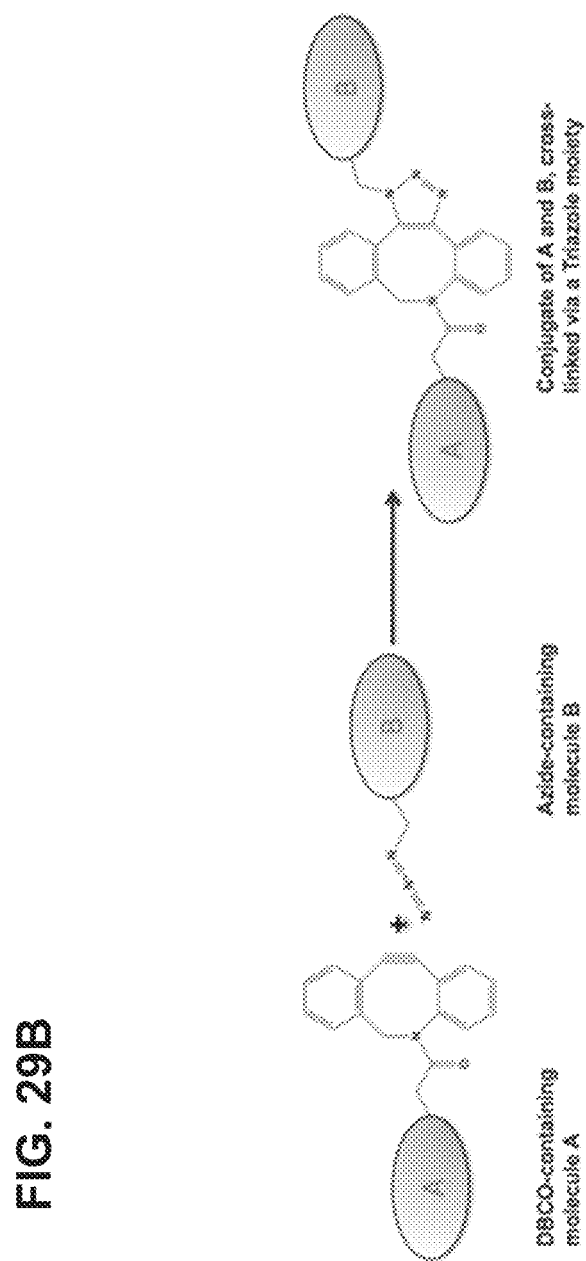

The DBCO-Avidin was then reacted with azide-DNA through "click" chemistry (Scheme V (FIG. 29A-FIG. 29B)). The product was then characterized with gel electrophoresis.

Example 6: Preparation of Linear DNA Scaffolds with One or More Branched Linkers Linear DNA scaffolds according to the present invention comprise DNA chains attached to the DNA chain at one or more points through a linker.

Figure 14:
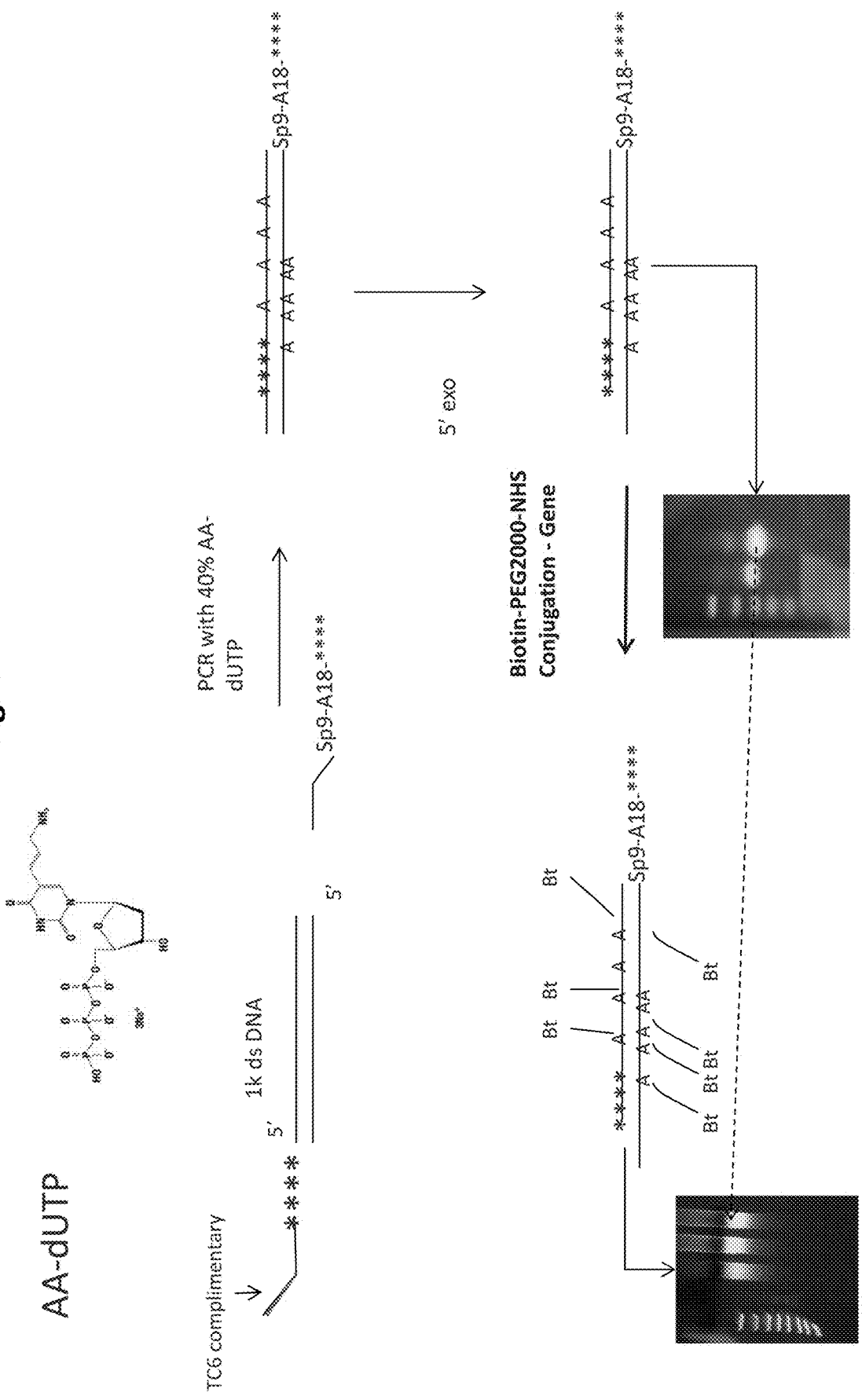
FIG. 14 is a schematic illustration of an embodiment of a scaffold synthesis scheme.

In an exemplary embodiment, aminopropargyl-dT was incorporated through PCR with aminopropargyl-dUTP at 40% of other dNTP concentration. The 1 kbp PCR product was purified and analyzed by gel electrophoresis. Then the PCR product was reacted with biotin-PEG2000-NHS ester. This conjugation product was characterized by nuclease digesting assay and gel electrophoresis. Final product was a 1 kbp DNA chain with 2000-MW PEG-biotin braches. (Scheme illustrated in FIG. 14).

Example 7: Preparation of Biotin-PEG Acrylamide Scaffold

Figure 15:
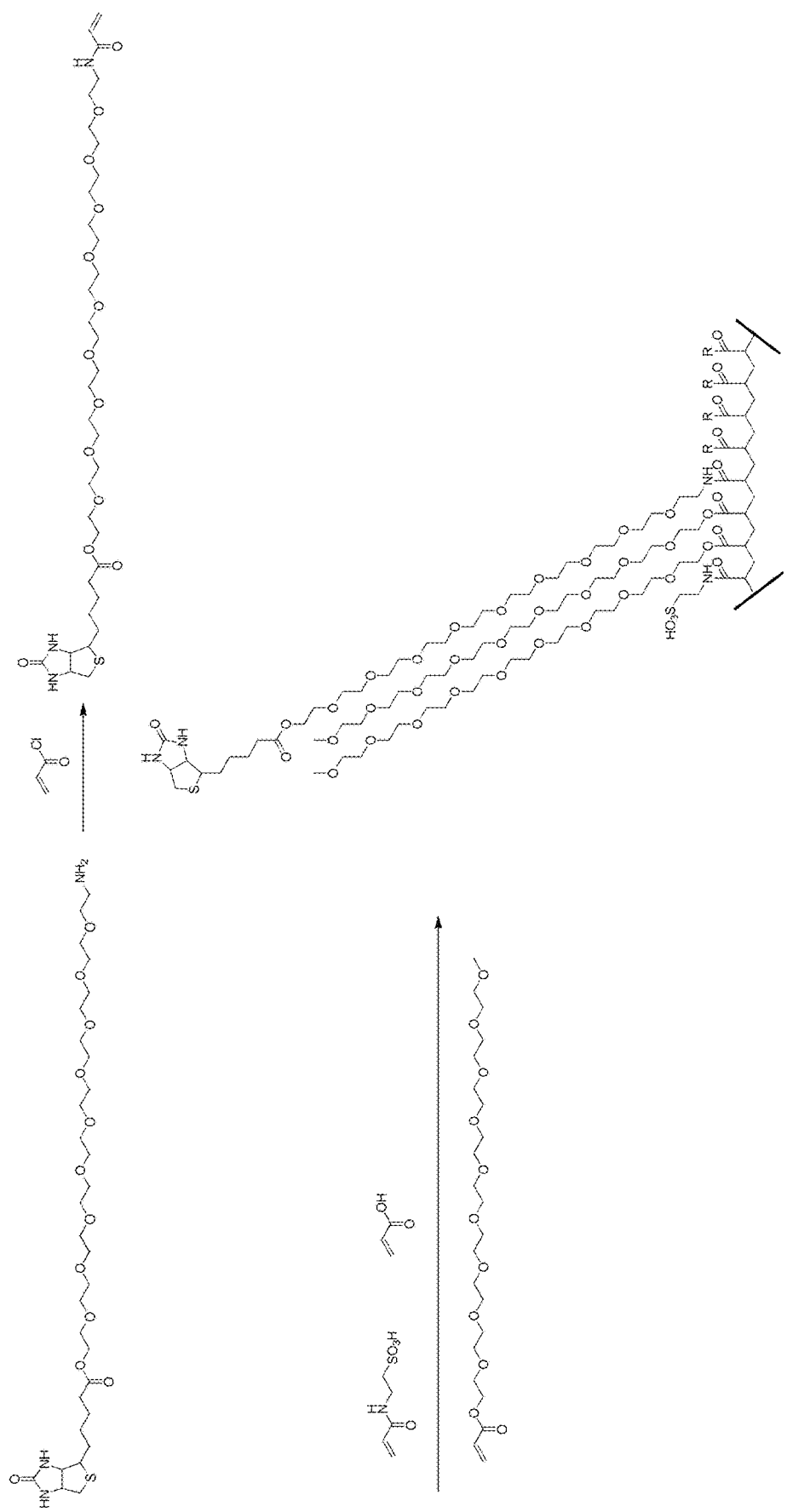
FIG. 15 is a schematic illustration of an embodiment of a scaffold synthesis scheme.

In another exemplary embodiment, scaffolds of the invention include a polymeric scaffold with a hydrophilic main chain and biotin-linker side chain. An example is biotin-PEG acrylamide is shown in FIG. 15.

To produce Biotin-PEG Acrylamide: To a solution of biotin-PEG (2 kD)-amine (100 mg, 0.064 mmol) and triethyl amine (26.7 uL) in DMF (3 mL) was added a solution of acrylic chloride (17.3 uL, 0.192 mmol) at room temperature under nitrogen atmosphere. The reaction solution was stirred for 2 h and then subjected to reverse-phase column chromatography purification (gradient 0.1 M TEAB/acetonitrile). The product fractions were combined and concentrated to dryness. Further drying under high vacuum drying gave 82.6 mg (80% yield) of a white solid product.

To produce Biotin-PEG (480) Acrylamide: To a solution of biotin-PEG (480)-amine (100 mg, 0.146 mmol) and triethyl amine (26.7 uL) in DMF (3 mL) was added a solution of acrylic chloride (39.6 uL, 0.439 mmol) at room temperature under nitrogen atmosphere. The reaction solution was stirred for 2 h and then subjected to reverse-phase column chromatography purification (gradient 0.1 M TEAB/acetonitrile). The product fractions were combined and concentrated to dryness. Further drying under high vacuum drying gave 80 mg (74% yield) of a white solid product.

To a solution of PEG-acrylamide (500 mg), biotin-PEG (480) acrylamide (50 mg) and sulfoethyl acrylamide (350 mg) in water (1000 uL) was added APS (30 mg) and TEMED (30 mg). The resultant solution was stirred in a vial overnight. The resultant polymer solution was dialyzed in a dialysis bag and stirred in a beaker with water (200 mL) for 16 h. The dialysis process was carried out three times with fresh water to ensure the complete removal of the unreacted monomers and small molecules. The resultant biotinylated polymer was stored in a water solution.

Example 8: Preparation of Aba11 Core Scaffolds

Figure 16A:
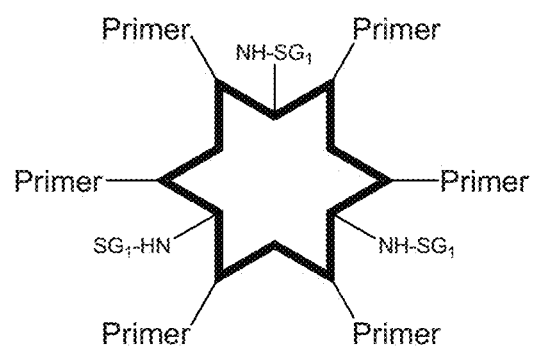
FIG. 16A-FIG. 16B shows an embodiment of a star-shaped scaffold. An exemplary preparation scheme of such a scaffold is shown in FIG. 16B.
Figure 16B:
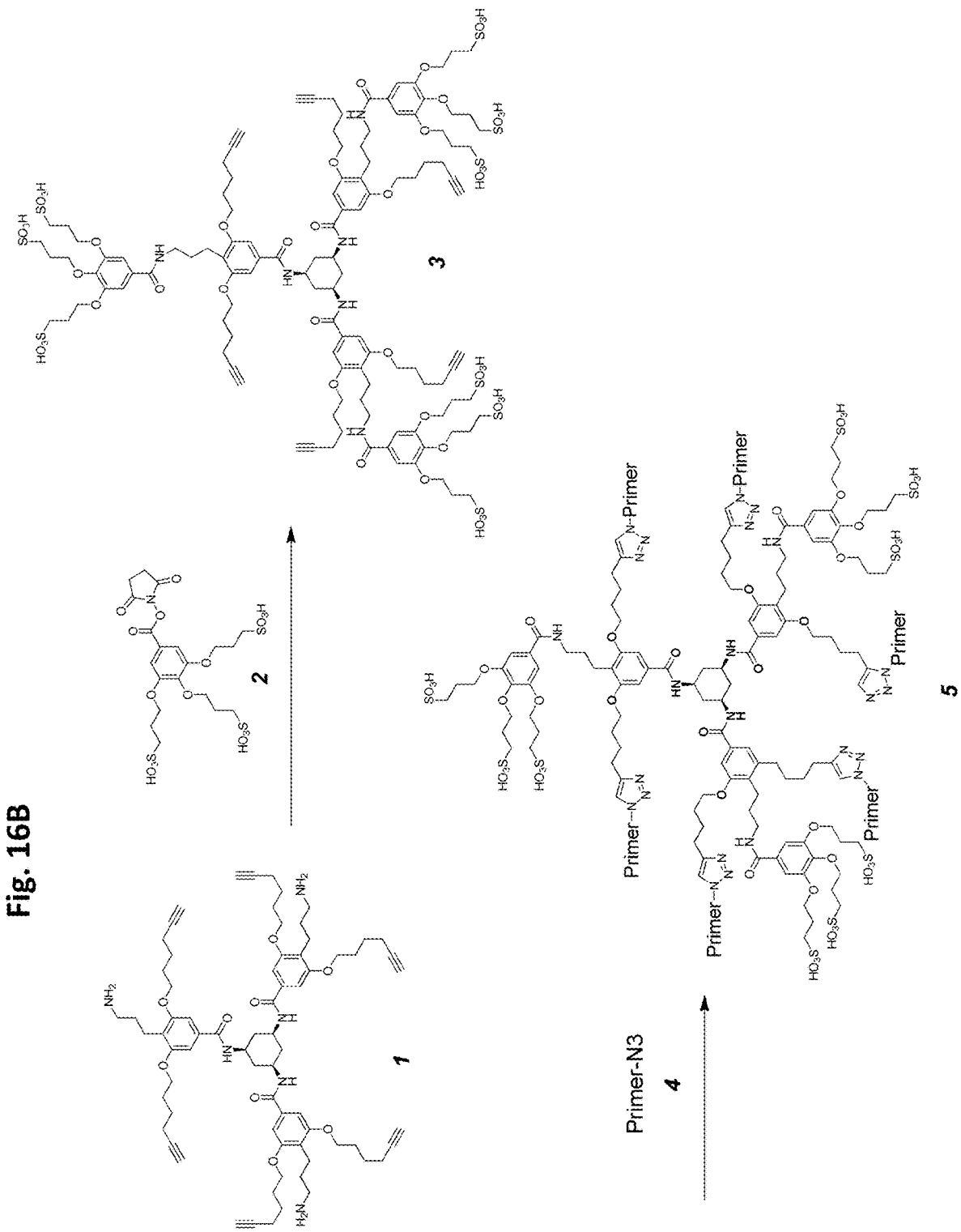

FIG. 16A shows an exemplary embodiment of an Aba11 Core star-shaped scaffold. An exemplary preparation scheme of such a scaffold is shown in FIG. 16B.

To a solution of the CS2 core scaffold (1, 87.2 nmole), prepared from coupling of triaminocyclohexane and derivative of amino protected benzoate NHS ester of the corresponding moiety, in DMF (80 uL) was added a solution of the SG1 NHS ester (2, 910 nmole) in DMF (1 uL) and DIPEA (2 uL). Additional 2 was added (2×1 uL) every two hours. The reaction solution was vortexed and stood at room temperature for a total of 18 h. The crude reaction solution was then subjected to reverse-phase HPLC purification (gradient 0.1 M TEAB/acetonitrile). The resultant fractions were combined and concentrated to dryness and re-dissolved in water (50 uL). There was obtained a solution (1147 µM×50 µL) of the desired product 3 (66% yield).

To a solution of the hexaacetylene 2 (3 nmole) in water (2.61 µL), was added azido oligonucleotide (80 nmol) in water (40 µL), TEAA buffer (200 mM, 20 µL), DPSA ligand (200 mM, 1 µL), CuSO$_4$ hydrate (100 mM, 2 µL), sodium ascorbate (200 mM, 2.5 µL) in a vial. The solution was vortexed and stood for 18 h without exposure to the light. The crude solution was then subjected to reverse-phase HPLC purification (gradient 0.1 M TEAB/acetonitrile). The resultant fractions were combined and concentrated to dryness and re-dissolved in water (100 µL). There was obtained a solution of the desired product, 31.5 µM×100 µL.

Figure 17A:
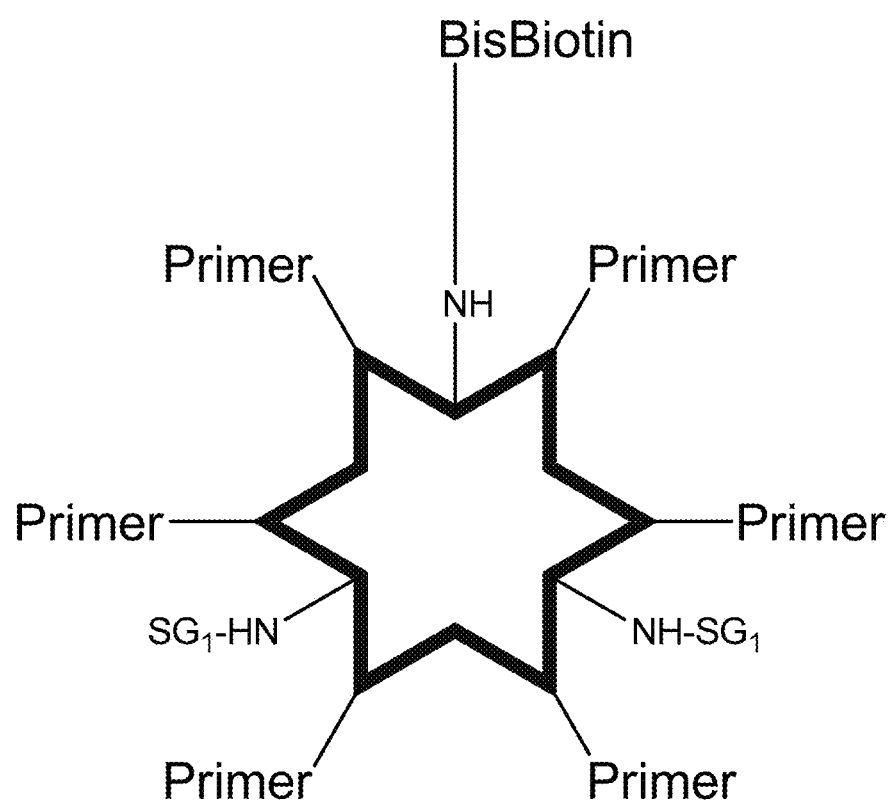
FIG. 17A-FIG. 17B shows an embodiment of a star-shaped scaffold. An exemplary preparation scheme of such a scaffold is shown in FIG. 17B.
Figure 17B:
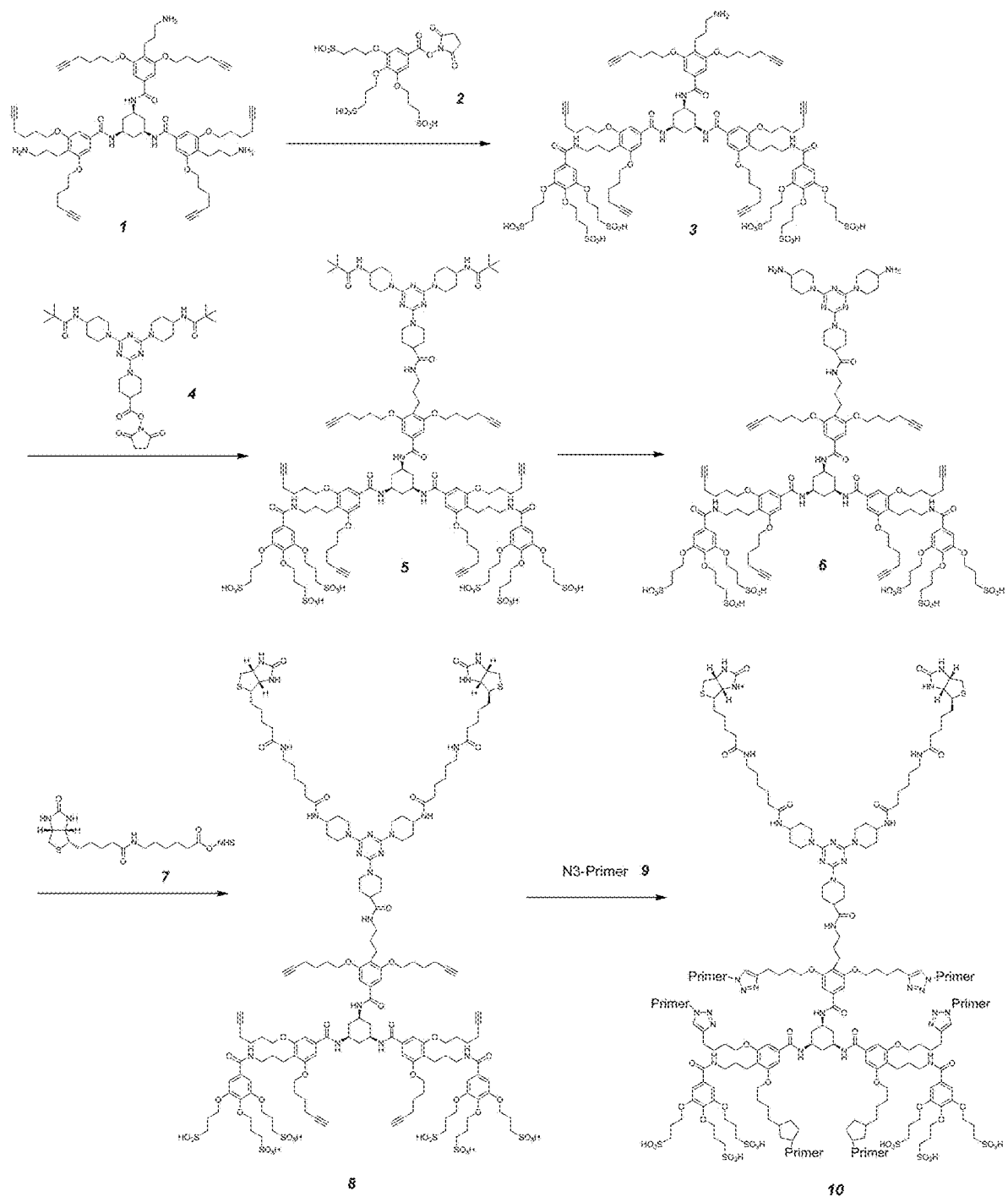

FIG. 17A shows an example of another Aba11 core star shaped scaffold. An exemplary preparation method is shown in FIG. 17B.

Preparation of (SG1)2-CS2 (3). To a solution of the CS2 core scaffold (1, 8.19 µmop in DMF (310 µL) was added a solution of the SG1 NHS ester (2, 19.0 µmole) in DMF (38 µL) and DIPEA (30 µL). The reaction solution was votexed and stood at room temperature for a total of 18 h. From analytical HPLC there were three major products, namely, the mono-coupled, di-coupled and tri-coupled products. The crude reaction solution was then subjected to reverse-phase HPLC separation (gradient 0.1 M TEAB/acetonitrile). The resultant fractions for three products were combined separately and concentrated to dryness to give the three products. Each of the three products was confirmed by LC/MS.

Preparation of (SG1)2-CS2-T2-(NH2)2 (6). To a solution of the bis-SG1-CS2-amine (3, 3 µmop in DMF (400 uL) was added a solution of the new triazine scaffold derivative, T2-(NHTFA)2-COONHS (4, 19.7 mg, 28.4 µmop and DIPEA (10 µL). The reaction solution was stirred overnight at room temperature. After concentrating the solvent to dryness the residual crude product 5 was dissolved in 1N KOH (4 mL) and stirred overnight at room temperature. The crude reaction solution was then subjected to reverse-phase HPLC separation (gradient 0.1 M TEAB/acetonitrile). The resultant fractions were combined and concentrated to dryness to give the desired product 6.

Preparation of (SG1)2-CS2-T2-(Biotin-X)2 (8). To a solution of the diamine (6, ~1.5 µmop in DMF (100 µL) was added DIPEA (10 µL) and biotin-X-NHS (7, 6.8 mg, 15 µmop. The resultant solution was vortexed and then stood for 18 h. The crude reaction solution was then subjected to reverse-phase HPLC purification (gradient 0.1 M TEAB/acetonitrile). The resultant product fractions were combined and concentrated to dryness to give the desired product 8 (1.8 mg, 0.55 µmop. The solid was dissolved in water (109.2 µL) to give a stock solution of 5 mM×109.2 µL.

Preparation of Bisbiotin-6-Arm-Primer [(SG1)2-CS2 core scaffold] (10). To a solution of the bis-biotin hexaacetylene 8 (10 nmole) in water (2 uL), was added azido oligonucleotide (120 nmol) in water (60 uL), TEAA buffer (200 mM, 60 uL), DPSA ligand (200 mM, 1 uL), CuSO4 hydrate (100 mM, 2 uL), sodium ascorbate (200 mM, 2.5 uL) in a vial. The solution was vortexed and stood for 18 h without exposure to the light. The crude solution was then subjected to reverse-phase HPLC purification (gradient 0.1 M TEAB/acetonitrile). The resultant fractions were combined and concentrated to dryness and re-dissolved in water (100 uL). There was obtained a solution (101.8 µM×100 µL) of the desired product 10.

Figure 18A:
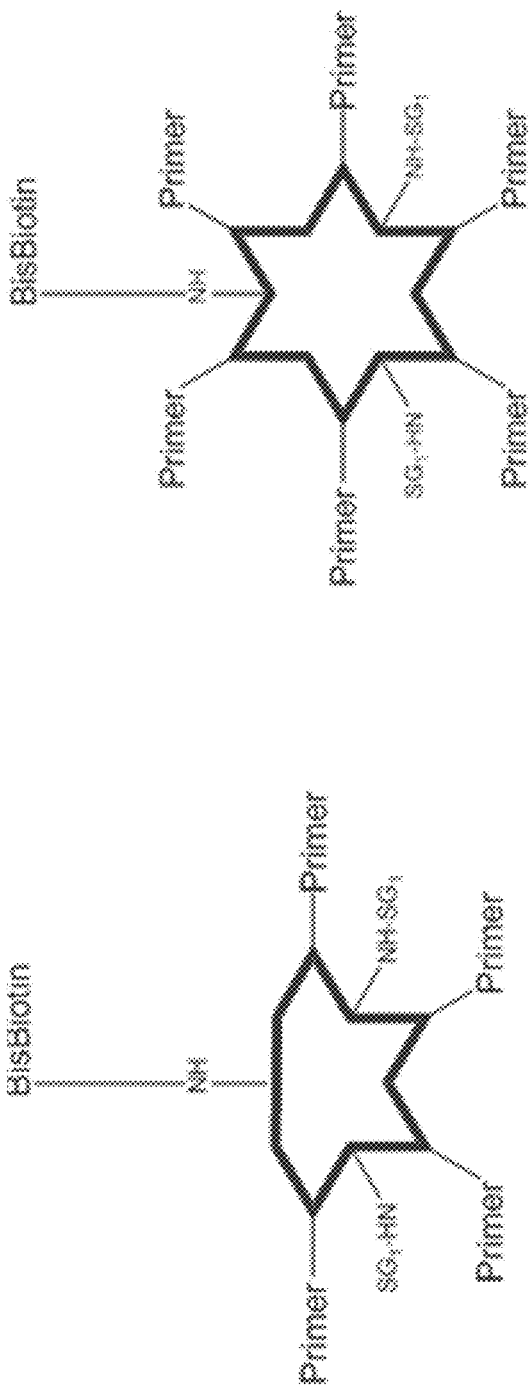
FIG. 18A-FIG. 18B shows an embodiment of a star-shaped scaffold. An exemplary preparation scheme of such a scaffold is shown in FIG. 18B.
Figure 18B:
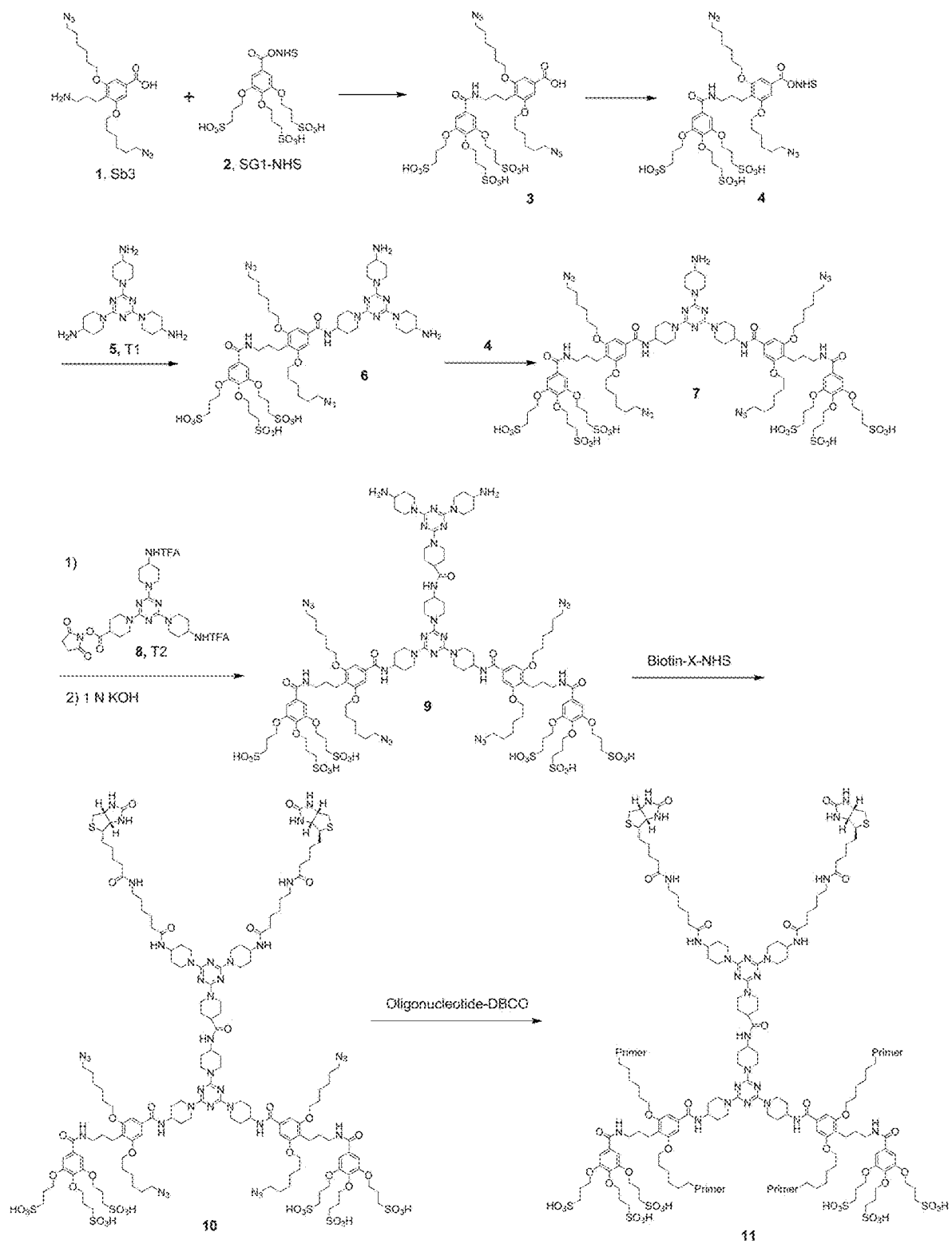

FIG. 18A shows another exemplary embodiment of Aba11 core star shaped scaffolds, exemplary preparation methods for which are shown in FIG. 18.

Preparation of Sb3-SG1 (3). To a solution of the Sb3 core scaffold (1, 23.1 mg, 50 µmole), prepared from 3,5-dihydroxy benzoic acid in four steps, in DMF (80 µL) was added a solution of the SG1 NHS ester (2, 61 µmole) in DMF (71 uL) and DIPEA (20 µL). The reaction solution was votexed and stood at room temperature for 18 h. The crude reaction solution was then subjected to reverse-phase HPLC purification (gradient 0.1 M TEAB/acetonitrile). The resultant fractions were combined and concentrated to dryness. Further drying in a desiccator under high vacuum gave 20.4 mg (42% yield) of the desired product.

Preparation of Sb3-SG1-NHS Ester (4). To a solution of Sb3-SG1 (3, 20.4 mg, 20.8 µmop in DMF (1 mL) was added carbonyldiimidazole (CDI, 34 mg, 208 µmop and N-hydroxysuccinimide (NHS, 12 mg, 104 µmop and stirred at room temperature for 18 h. To the solution was added ethyl ether (40 mL) in a polypropylene centrifuge tube. The resultant mixture was centrifuged at high speed (4000 RPM) for 3 min. The solvent was decanted. The resultant solid was dissolved in DMF (1 mL) and repeated the precipitation step with ethyl ether one more time. The resultant solid was dried under high vacuum for 4 h, dissolved in DMF (1 mL) to give a stock solution of 20 mM.

Preparation of Sb3-SG1-T1 (6). To a solution of Sb3-SG1-NHS (4, 5 µmol) in DMF (250 uL) was added a solution of T1 (5, 19.4 mg, 40 µmole) in 0.2 M NaHCO3 aqueous solution (50 µL). The reaction was stirred at room temperature for 18 h. The crude solution was then subjected to reverse-phase HPLC purification (gradient 0.1 M TEAB/acetonitrile). The resultant fractions were combined and concentrated to dryness and dissolved in 0.2 M NaHCO3 aqueous solution (100 µL).

Preparation of (Sb3-SG1)2-T1 (7). To a solution of Sb3-SG1-NHS (4, 5 µmol) in DMF (250 µL) was added a solution of Sb3-SG1-T1 (6) in 0.2 M NaHCO3 aqueous solution (100 µL). After stirring for 18 h the crude reaction solution was then subjected to reverse-phase HPLC purification (gradient 0.1 M TEAB/acetonitrile). The resultant fractions were combined and concentrated to dryness. A 1.6 mg (0.7 µmol) of solid product was obtained. Dissolved the solid in DMF (200 µL) to give the product stock solution.

Preparation of (Sb3-SG1)2-T1-T2-(NH2)2 (9). To a solution of (Sb3-SG1)2-T1 (7, 0.4 mg, 0.175 µmol) in DMF (50 uL) was added T2-(NHTFA)2-NHS (8, 4.0 mg, 5.7 µmol) in DMF (200 µL) followed by addition of 0.2 M NaHCO3 aqueous solution (100 µL). The reaction was stirred overnight and progress of reaction was monitored using UPLC for the formation of product. To the solution was then added 1 N KOH (200 µL) and stirred another 18 hours. The crude reaction solution was then subjected to reverse-phase HPLC purification (gradient 0.1 M TEAB/acetonitrile). The resultant fractions were combined and concentrated to dryness to give the product.

Preparation of (Sb3-SG1)2-T1-T2-(X-Biotin)$_2$ (10). To a solution of (Sb3-SG1)2-T1-(NH$_2$)$_2$ (9) in 0.2 M NaHCO3 aqueous solution (50 µL) was added a solution of biotin-X-NHS (4.6 mg, excess) in DMF (500 µL). The solution was stirred overnight at room temperature. The crude reaction solution was then subjected to reverse-phase HPLC purification (gradient 0.1 M TEAB/acetonitrile). The resultant fractions were combined and concentrated to dryness to give the product. Quantification of the product solution using UV absorbance with extinction coefficient of 84,800 (max absorbance of 260 nm) gave a solution of the product, 89.8 µM×100 µL (8.98 nmol).

Preparation of Bisbiotin-4-Arm-Primer (11). To a solution of (Sb3-SG1)2-T1-T2-(X-Biotin)2 (10, 4.5 nmol) in water (50 µL) was added a solution of the oligonucleotide-DBCO (72 nmol) in water (72 µL) and 2 M TEAA (10 µL). The solution was votexed and stood in a rack for 2 days. The crude reaction solution was then subjected to reverse-phase HPLC purification (gradient 0.1 M TEAB/acetonitrile). The resultant fractions were combined and concentrated to dryness. The product was again subjected to ion exchange column chromatography purification (0.05 M TEAB/20% ACN, 1.5 M TEAB/20% ACN). The product was quantified using the oligonucleotide's extinction coefficient to give 8.48 µM×95 µL of the stock product solution.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method of distributing single polymerase molecules into array regions, the method comprising;
   (a) providing a surface comprising a plurality of array regions, wherein each array region comprises several binding elements; and
   (b) exposing the surface to a solution comprising polymerase enzyme compositions, wherein each polymerase enzyme composition comprises a polymerase bound to a linear DNA structure comprising multiple functional moieties, wherein the multiple functional moieties comprise biotin moieties or avidin moieties, and wherein the multiple functional moieties are attached to the linear DNA structure through flexible linkers comprising a polymeric structure selected from the group consisting of polyethylene glycol, a peptide, and an aliphatic carbon chain,
   wherein the exposing is conducted under conditions such that the multiple functional moieties of the linear DNA structure react with available binding elements in a given array region and prevent other polymerase enzyme compositions from loading in that given array region,
   thereby distributing single polymerase molecules into array regions.

2. The method of claim 1, wherein the flexible linkers are attached to the linear DNA structure via a modified base.

3. The method of claim 2, wherein the modified base is a member selected from the group consisting of aminoallyl-dT, aminopropargyl-dT, a thiol-modified base, an azide modified base, and an alkyl-modified base.

4. The method of claim 1, wherein the flexible linkers have a length of about 0.5 nm to about 3 nm.

5. The method of claim 1, wherein the flexible linkers have a length of about 1 nm.

6. The method of claim 1, wherein the flexible linkers have a length of about 2 nm.

7. The method of claim 1, wherein the array regions comprise zero mode waveguides (ZMWs).

8. The method of claim 1, wherein the exposing step (b) is conducted in the presence of a divalent cation to improve loading of the polymerase enzyme compositions into the array regions as compared to loading in the absence of divalent cation.

9. The method of claim 1, wherein the distributing of the single polymerase molecules results in more than 37% of the array regions containing a single polymerase molecule.

10. The method of claim 1, wherein the functional moieties comprise biotin moieties.

11. The method of claim 10, wherein the binding elements comprise avidin moieties.

12. The method of claim 1, wherein the functional moieties comprise avidin moieties.

13. The method of claim 12, wherein the binding elements comprise biotin moieties.

14. The method of claim 1, wherein the polymerase enzyme is bound to a single nucleic acid template.

15. The method of claim 14, wherein the single nucleic acid template comprises:
    (i) a double stranded nucleic acid segment having a first and second end;
    (ii) a first hairpin oligonucleotide connecting each strand of the single template nucleic acid at the first end; and
    (iii) a second hairpin oligonucleotide connecting each strand of the single template nucleic acid at the second end.

16. The method of claim 14, wherein the single nucleic acid template comprises a single stranded nucleic acid molecule hybridized to a primer.

17. The method of claim 1, wherein the avidin moieties comprise tetrameric avidin proteins.

18. The method of claim 1, wherein the avidin moieties comprise avidin, streptavidin, tamavidin, traptavidin, xenavidin, or bradavidin.

* * * * *